(12) United States Patent
Chan et al.

(10) Patent No.: US 7,402,728 B2
(45) Date of Patent: Jul. 22, 2008

(54) TRANSGENIC MICE EXPRESSING HUMAN CD20 AND/OR CD16

(75) Inventors: Andrew Chee-Yuen Chan, Menlo Park, CA (US); Qian Gong, Foster City, CA (US); Flavius Martin, Hayward, CA (US)

(73) Assignee: Genentech, Inc., South San Francisco, CA (US)

( * ) Notice: Subject to any disclaimer, the term of this patent is extended or adjusted under 35 U.S.C. 154(b) by 23 days.

(21) Appl. No.: 10/537,963

(22) PCT Filed: Dec. 11, 2003

(86) PCT No.: PCT/US03/39686

§ 371 (c)(1), (2), (4) Date: Mar. 9, 2006

(87) PCT Pub. No.: WO2004/060052

PCT Pub. Date: Jul. 22, 2004

(65) Prior Publication Data

US 2006/0218655 A1    Sep. 28, 2006

Related U.S. Application Data

(60) Provisional application No. 60/434,115, filed on Dec. 16, 2002, provisional application No. 60/476,481, filed on Jun. 5, 2003.

(51) Int. Cl.
A01K 67/033    (2006.01)
C12N 15/00    (2006.01)

(52) U.S. Cl. .............................. 800/13; 800/9; 800/10; 800/21

(58) Field of Classification Search ........................ None
See application file for complete search history.

(56) References Cited

U.S. PATENT DOCUMENTS

| 5,859,312 A | 1/1999 | Littman et al. |
| 2002/0064823 A1 | 5/2002 | Welcher et al. |
| 2002/0128448 A1 | 9/2002 | Reff |

FOREIGN PATENT DOCUMENTS

| EP | 1 452 093 | 9/1994 |
| WO | 95/15376 A | 6/1995 |
| WO | 95/28959 A | 11/1995 |
| WO | 99/00010 | 1/1999 |
| WO | WO 02/062946 A2 | 8/2002 |

OTHER PUBLICATIONS

Moreadith et al, J. Mol. Med., Mar. 1997;75(3):208-16.*
Pera et al, Journal of Cell Science 2000;113: 5-10.*
Logan et al, Clin Exp Pharmacol Physiol 1999;26:1020-5.*
Denning, Nat Biotech 2001;19:559-562.*
Smith and Murphy, Cloning Stem Cells 2004;6:126-32.*
Polejaeva et al, Nature 2000;407:86-90.*
Simerly et al, Science 2003;300:297.*
Serfini et al. Characterization of CD20-transduced T lymphocytes as an alternative suicide gene therapy approach for the treatment of graft-versus-host disease. *Human Gene Therapy*. Jan. 2004, vol. 15, pp. 63-76.
Kawanaka et al. Expression of Fc gamma receptor III (CD16 on monocytes during hemodialysis in patients with chronic renal failure. *Nephron*. Jan. 2002, vol. 90, No. 1, pp. 64-71.
Heijnen, I. et al. "Antigen targeting to myeloid-specific human Fc-gamma-RJ-CD64 triggers enhanced antibody responses in transgenic mice cd," Journal of Clinical Investigation, 97(2):331-338, Jan. 1996.
Guyre, P. et al. "Increased potency Fc-receptor-targeted antigens," Cancer Immunology Immunotherapy, 45(3-4):146-148, 1997.
Flamad, V. "Delayed maturation of CD4-CD8-Fc-Gamma-R11-I11+ T and natural killer cell precursors in Fc-Epsilon-R1-Gamma transgenic mice," Journal of Experimental Medicine, 184(5):1725-1734, Nov. 1996.
Scharenberg, A. et al. "The FcRbeta subunit functions as an amplifier of Fc Rgamma mediated cell activation signal," The Journal of Allergy and Clinical Immunology, 99(1, part 2):s406, Jan. 1997.
European Search Report mailed Apr. 3, 2006.
International Search Report mailed Aug. 6, 2004.
International Search Report mailed Feb. 23, 1999.
Arzoo et al., "Treatment of refractory antibody mediated autoimmune disorders with an anti-CD20 monoclonal antibody (rituximab)", Ann. Rheum. Dis., 61:922-924 (2002).
Butler, "The Amplified ELISA: Principles of and Applications for the Comparative Quantitation of Class and Subclass Antibodies and the Distribution of Antibodies and Antigens in Biochemical Separates", *Methods in Enzymology*. 73:482-523 (1981).
Capecchi, "Altering the Genome by Homologous Recombination", *Science*, 244:1288-1292 (1989).
Capecchi, "The New Mouse Genetics: Altering the Genome by Gene Targeting", *TIG*, 5(3):70-76 (1989).

(Continued)

*Primary Examiner*—Q. Janice Li
(74) *Attorney, Agent, or Firm*—Morrison & Foerster LLP

(57) ABSTRACT

The present invention generally relates to non-human transgenic animals expressing human cellular markers, including CD20 and/or preferably CD16.

23 Claims, 42 Drawing Sheets

OTHER PUBLICATIONS

Davis et al., "Single-Agent Monoclonal Antibody Efficacy in Bulky Non-Hodgkin's Lymphoma: Results of a Phase II Trail of Rituximab", *Journal of Clinical Oncology*, 17(6):1851-1857 (1999).

Fleit et al., "A Soluble Form of FcγRIII is Present in Human Serum and Other Body Fluids and is Elevated at Sites of Inflammation", *Blood*, 79(10):2721-2728 (1992).

Foran et al., "European Phase II Study of Rituximab (Chimeric Anti-CD20 Monoclonal Antibody) for Patients with Newly Diagnosed Mantle-Cell Lymphoma and Previously Treated Mantle-Cell Lymphoma. Immunocytoma. and Small B-Cell Lymphocytic Lymphoma", *Journal of Clinical Oncology*, 18(2):317-324 (2000).

Gong et al., "Importance of cellular microenvironment and circulatory dynamics in B cell immunotherapy", *Journal of Immunology*, 174(2):817-826 (2005).

Gopal et al., "Clinical applications of anti-CD20 antibodies", *J. Lab. Clin. Med.*, 134:445-450 (1999).

Kim et al., "Construction and Characterization of a Human Bacterial Artificial Chromosome Library". *Genomics*, 34:213-218 (1996).

Mansour et al., "Disruption of the proto-oncogene *int-2* in mouse embryo-derived stem cells: a general strategy for targeting mutations to non-selectable genes", *Nature*, 336:348-352 (1988).

Mathiot et al., "Correlation Between Soluble Serum CD16 (sCD16) Levels and Disease Stage in Patients with Multiple Myeloma", *Journal of Clinical Immunology*, 13(1):41-48 (1993).

Polyak et al., "Alanine-170 and Proline-172 are critical determinants for extracellular CD20 epitopes; heterogeneity in the fine specificity of CD20 monoclonal antibodies is defined by additional requirements imposed by both amino acid sequence and quatemary structure", *Blood*, 99(9):3256-3262 (2002).

Protheroe et al., "Remission of inflammatory arthropathy in association with anti-CD20 therapy for non-Hodgkin's lymphoma", *Rheumatology*. 38:1150-1152 (1999).

Shizuya et al., "Cloning and stable maintenance of 300-kilobase-pair fragments of human DNA in *Escherichia coli* using an F-factor-based vector", *Proc. Natl. Acad. Sci. USA*, 89:8794-8797 (1992).

Solal-Celigny et al., "Rituximab as First-Line Treatment of Patients with Follicular Lymphoma (FL) and a Low-Burden Tumor: Clinical and Molecular Evaluation", *Blood.* 94(10):631a, Abstract #2802 (1999).

Swiatek et al., "Perinatal lethality and defects in hindbrain development in mice homozygous for a targeted mutation of the zinc finger gene *Krox20*", *Genes & Development*, 7:2071-2084 (1993).

Trape, "Rituximab chimeric anti-CD20 monoclonal antibody treatment for refractory hemolytic anemia in patients with lymphoproliferative disorders", *Haematologica*, 88:223-225 (2003).

Van de Winkel et al., "Human IgG Fc receptor heterogeneity: molecular aspects and clinical implications", *Immunology Today*, 14(5):215-221 (1993).

Weiner, "Monoclonal Antibody Therapy of Cancer", *Seminars in Oncology*, 26(5)(Suppl. 14):43-51 (1999).

White et al., "Anti-CD20 monoclonal antibodies as novel treatments for non-Hodgkin's lymphoma", *Pharm. Sci. Technol. Today*, 2(3):95-101 (1999).

Zelenetz et al., "Iodine I 131 Tositumomab for Patients with Transformed Low-Grade Non-Hodgkin's Lymphoma (NHL): Overall Clinical Trial Experience", *Blood*, 94(10):632a. Abstract 2806 (1999).

GenBank Accession No. AH003353 dated Feb. 22, 1996.
GenBank Accession No. BC002807 dated Jul. 15, 2006.
GenBank Accession No. M62541 dated Jul. 26, 1993.
GenBank Accession No. P30273 dated Jun. 13, 2006.
GenBank Accession No. M27394 dated Jul. 15, 1993.
GenBank Accession No. M27395 datd Feb. 22, 1996.
GenBank Accession No. NM_010188 dated Jun. 12, 2006.
GenBank Accession No. NM_000569 dated Jul. 16, 2006.
GenBank Accession No. NM_000570 dated Jul. 2, 2006.
GenBank Accession No. Z46222 dated Apr. 18, 2005.
GenBank Accession No. Z46223 dated Mar. 20, 1997.

Supplementary Partial European Search Report dated May 22, 2006.

Cameron, 1997, *Molecular* Biology 7:253-265 "Recent Advances in Transgenic Technology".

Hammer et al., 1986, *Journal of Animal Science* 63:269-278 "Genetic Engineering of Mammalian Embryos".

Houdebine, 1994, *J. Biotech*. 34:269-287 "Production of pharmaceutical proteins from transgenic animals".

Kappell et al., 1992, *Current Opinion in Biotechnology* 3:548-553 "Regulating gene expression in transgenic animals".

Mullins et al., 1993, *Hypertension* 22:630-633 "Transgenesis in nonmurine species".

Mullins et al., 1996, *Journal of Clinical Investment* 98:S37-S40 "Perspectives Series: Molecular Medicine in Genetically Engineered Animals: Transgenesis in the Rat and Larger Mammals".

Niemann, 1998, *Transgenic Research* 7:73-75 "Transgenic farm animals get off the ground".

Sigmund, 2000, *Arterioscler Thromb. Vasc. Boil.* 20:1425-1429 "Viewpoint: Are Studies in Genetically Altered Mice Out of Control?".

Wall, 1996, *Theriogenology* 45:57-68 "Transgenic Livestock: Progress and Prospects for the Future".

Wall, 1997, *Journal of Dairy* Science 80(9):2213-2224 "Transgenic Dairy Cattle: Genetic Engineering on a Large Scale".

Wilmut, 2003, *Cloning Stem Cell* 5(2):99-100 "Editorial: Dolly—Her Life and Legacy".

International Search Report for PCT/US03/40426, mailed Apr. 7, 2005, 4 pages.

Liu et al., "Production of a Mouse-Human Chimeric Monoclonal Antibody to CD20 with Potent Fc-Dependent Biological Activity", The Journal of Immunology (1987) 139(10):3521-3526.

\* cited by examiner

Expression of Human CD20 and CD16 Transgenes

FIGURE 22A

MGGGAGERLFTSSCLVGLVPLGLRISLVTCPLQCGIMWQLLLPT
ALLLLVSAGMRTEDLPKAVVFLEPQWYRVLEKDSVTLKCQGAYS
PEDNSTQWFHNESL ISSQASSYFIDAATVDDSGEYRCQTNLSTL
SDPVQLEVHIGWLLLQAPRWVFKEEDPIHLRCHSWKNTALHKVT
YLQNGKGRKYFHHNSDFYIPKATLKDSGSYFCRGLVGSKNVSSE
TVNITITQGLAVSTISSFFPPGYQVSFCLVMVLLFAVDTGLYFSVKT
NIRSSTRDWKDHKFKWRKDPQDK

FIGURE 22B

```
   1 gattctgtgt gtgtcctcag atgctcagcc acagaccttt gagggagtaa aggggggcaga
  61 cccacccacc ttgcctccag gctctttcct tcctggtcct gttctatggt ggggctccct
 121 tgccagactt cagactgaga agtcagatga agtttcaaga aaaggaaatt ggtgggtgac
 181 agagatgggt ggaggggctg gggaaaggct gtttacttcc tcctgtctag tcggtttggt
 241 cccttaggg ctccggatat ctttggtgac ttgtcctctc cagtgtggca tcatgtggca
 301 gctgctcctc ccaactgctc tgctacttct agtttcagct ggcatgcgga ctgaagatct
 361 cccaaaggct gtggtgttcc tggagcctca atggtacagg gtgctcgaga aggacagtgt
 421 gactctgaag tgccagggag cctactcccc tgaggacaat tccacacagt ggtttcacaa
 481 tgagagcctc atctcaagcc aggcctcgag ctacttcatt gacgctgcca cagtcgacga
 541 cagtggagag tacaggtgcc agacaaacct ctccaccctc agtgacccgg tgcagctaga
 601 agtccatatc ggctggctgt tgctccaggc ccctcggtgg gtgttcaagg aggaagaccc
 661 tattcacctg aggtgtcaca gctggaagaa cactgctctg cataaggtca catatttaca
 721 gaatggcaaa ggcaggaagt attttcatca taattctgac ttctacattc caaaagccac
 781 actcaaagac agcggctcct acttctgcag ggggcttgtt gggagtaaaa atgtgtcttc
 841 agagactgtg aacatcacca tcactcaagg ttttggcagtg tcaaccatct catcattctt
 901 tccacctggg taccaagtct ctttctgctt ggtgatggta ctcctttttg cagtggacac
 961 aggactatat ttctctgtga agacaaacat tcgaagctca acaagagact ggaaggacca
1021 taaattaaa tggagaaagg accctcaaga caaatgaccc ccatcccatg ggggtaataa
1081 gagcagtagc agcagcatct ctgaacattt ctctggattt gcaaccctat catcctcagg
1141 cctctctaca agcagcagga aacatagaac tcagagccag atcccttatc caactctcga
1201 cttttccttg gtctccagtg gaagggaaaa gcccatgatc ttcaagcagg gaagccccag
1261 tgagtagctg cattcctaga aattgaagtt tcagagctac acaaacactt tttctgtccc
1321 aaccgttccc tcacagcaaa gcaacaatac aggctaggga tggtaatcct ttaaacatac
1381 aaaaattgct cgtgttataa attcccagt ttagagggga aaaaaaaaca attattccta
1441 aataaatgga taagtagaat taatggttga ggcaggacca tacagagtgt gggaactgct
1501 ggggatctag ggaattcagt gggaccaatg aaagcatggc tgagaaatag caggtagtcc
1561 aggatagtct aagggaggtg ttcccatctg agcccagaga taagggtgtc ttcctagaac
1621 attagccgta gtggaattaa caggaaatca tgagggtgac gtagaattga gtcttccagg
1681 ggactctatc agaactggac catctccaag tatataacga tgagtcctct taatgctagg
1741 agtagaaaat ggtcctagga aggggactga ggattgcggt ggggggtggg gtggaaaaga
1801 aagtacagaa caaaccctgt gtcactgtcc caagttgcta agtgaacaga actatctcag
1861 catcagaatg agaaagcctg agaagaaaga accaaccaca agcacacagg aaggaaagcg
1921 caggaggtga aaatgctttc ttggccaggg tagtaagaat tagaggttaa tgcagggact
1981 gtaaaaccac cttttctgct tcaatatcta attcctgtgt agctttgttc attgcattta
2041 ttaaacaaat gttgtataac caatactaaa tgtactactg agcttcgctg agttaagtta
```

FIGURE 22B
(CONT'D)

2101 tgaaactttc aaatccttca tcatgtcagt tccaatgagg tggggatgga gaagacaatt 2161 gttgcttatg aaagaaagct ttagctgtct ctgttttgta agctttaagc gcaacatttc 2221 ttggttccaa taaagcattt tacaagatct tgcatgctac tcttagatag aagatgggaa 2281 aaccatggta ataaaatatg aatgataaaa aaaaaaaaa aaaaaaaaa aaaaaaaaa 2341 a

FIGURE 22C

```
   1 aagcttccca tcctgttgca gtcccttact ctcctcctgt gctctctcct cttcttccta
  61 tctagcccac ccttttggta gctaagaatt cctccctcca ttggagagcc acagaccaaa
 121 gaggagtcaa ataagaaaat aagacctcaa agaaggaaaa caaagtgaag gccttgcatc
 181 agaagtcacg tggcagaaag ccacctggat atctgaaaag aagaaagaat tgagggatat
 241 ccgcttttg cctcagagac catccttagc cctgaaggct ttgtttctgc tttaggtttc
 301 ccagataagc atccgaagtg ctacagcaag gaactttaag tttccagata cttgtctgga
 361 ttttgcaagg cgtagatgag tcacttgaga aggagaactg gaatggctgc ctaggttcat
 421 ttccattgtg caatccaagg gcctgtggag aaggggctgc tgcaagactc tgtgtgtggc
 481 gggggaggg gtgggtacgt ggatggcaat gggaggatca attaactcca cccaggagcc
 541 aaatgaaaca cacaaataaa aaacaaaacc tgagtagtgg ttttaggtc attctggagt
 601 agaaagagca ttcatttata gcaaaggttg gcgggcacct gtgtcagccc ctgcctccac
 661 tccacccta acaagtatca ggtgcccaca cgggcctgct gctcgcctcc tgggcttttc
 721 taagccaggt gagacctgtc ccagatgtcc acgaatccac tggggagtg gcactatcaa
 781 gcagagtcat ctgattttct gcctgggacc tggaccattg tgagagtaac caacgtgggg
 841 ttacggggga gaatctggag agaagagaag aggttaacaa ccctcccact tcctggccac
 901 cccctccac cttttctggt aaggagccct ggagccccgg ctcctaggct gacagaccag
 961 cccagatcca gtggcccgga ggggcctgag ctaaatccgc aggacctggg taacacgagg
1021 aaggtaaaga gttcctgtcc tcgccctcc ccacccccac cttttctgtg atcttttcag
1081 cctttcgctg gtgacttgtt cttccagggc ccatttctct accctacctg ggtttcttct
1141 aacctggaaa tctaatgatc aaatcacact aaaaagtcag tagctcctgt ggattacata
1201 tcccaggagc atatagattt tgaattttga attttgaaag aaattctgcg tggagataat
1261 attgaggcag agacactgct agtggtctga agatttgaaa ggaccacttt ctgtgtgcag
1321 gcagggcctc agctggagat agatgggtct gggcgaggca ggagagtgac aagttctgag
1381 gtgaaatgaa ggaagccctc agagaatgct cctcccacct tgaatctcat ccccagggtc
1441 tcactgtccc attcttggtg ctgggtggat ccaaatccag gagatggggc aagcatcctg
1501 ggatggctga gggcacactc tggcagattc tgtgtgtgtc ctcagatgct cagccacaga
1561 cctttgaggg agtaaagggg gcagacccac ccaccttgcc tccaggctct ttccttcctg
1621 gtcctgttct atggtgggc tcccttgcca gacttcagac tgagaagtca gatgaagttt
1681 caagaaaagg aaattggtgg gtgacagaga tgggtggagg ggctggggaa aggctgttta
1741 cttcctcctg tctagtcggt ttggtcccct tagggctccg gatatctttg gtgacttgtc
1801 cactccagtg tggcatcatg tggcagctgc tcctcccaac tgctctgcta cttctaggta
1861 agtcagggtc tccctggttg agggagaagt ttgagatgcc ttgggttcag cagagacccc
1921 ttttcaggct acgaatgaga ctcccacgaa gggatgggac ccctcaccac atctatagct
1981 gtggattgag ctcctaggac aagccaagat ggggctagaa atgaggagaa tgctggttcc
2041 aattgggca tactcatgag tgaggccagt cacttcaccc ctctgggtcc cagaatcact
```

FIGURE 22C
(CONT'D)

```
2101 ctgtggaacc aaagagcttc gactagatgg tccctagggt ctgtctcttt cagtttgaca
2161 ttccagggtt ctcctctatg attttcaatt tctacccttt cttgtgggga tatgggttga
2221 ggctctttct gtagcttggt tcagggaaat tcaacctgta cccttaattt gtgagtttgc
2281 acagggagca aggggtaagg gagcagtgtt gaaaataggg atttgtgttg acagtggcgc
2341 aagaggcatg aacagtggag accagagagc aggtagcaag gtttccacca gaaacatcct
2401 gattcttggg aaaattgggc tcctggggca gaggagggca ggggagtttt aaactcactc
2461 tatgttctaa tcactctgat ctctgcccct actcaatatt tgatttactc tttttcttg
2521 cagtttcagc tggcatgcgg actggtgagt cagcttcatg gtcttggatt gacccagtgg
2581 ggcacatatg gggacaaagg ccataagata ttgggaaatg cttgttgaat gggaaaatgc
2641 tgatgtgggg ttagcaggga tagttcctcc aacacagcag aacttggccc tgtgcttctc
2701 tggccagctt tccttaagat actgaacagg ccaaaaatgg ggccaagatg ctctaagact
2761 gagccaccaa gcatgggttt gcaatgagct cattctggct ttgaggctcc ctgggaatgg
2821 cagtgtagag cctgctcctc tccctgtcct caccccacat tatcttggct cctcagaaga
2881 tctcccaaag gctgtggtgt tcctggagcc tcaatggtac agggtgctcg ag
```

Figure 22D
Mouse CD16 alpha chain

```
  1 gtagttcatc tcctgaacct catcagactc tgatccagtt cttgaatgac tttggacacc
 61 cagatgtttc agaatgcaca ctctggaagc caatggctac ttccaccact gacaattctg
121 ctgctgtttg cttttgcaga caggcagagt gcagctcttc cgaaggctgt ggtgaaactg
181 gaccccccat ggatccaggt gctcaaggaa gacatggtga cactgatgtg cgaagggacc
241 cacaaccctg ggaactcttc tacccagtgg ttccacaacg ggaggtccat ccggagccag
301 gtccaagcca gttacacgtt taaggccaca gtcaatgaca gtggagaata tcggtgtcaa
361 atggagcaga cccgcctcag cgaccctgta gatctgggag tgatttctga ctggctgctg
421 ctccagaccc tcagcgggt gtttctggaa ggggaaacca tcacgctaag gtgccatagc
481 tggaggaaca aactactgaa caggatctca ttcttccata tgaaaaatc cgtgaggtat
541 catcactaca aaagtaattt ctctatccca aaagccaacc acagtcacag tggggactac
601 tactgcaaag gaagtctagg aagtacacag caccagtcca gcctgtcac catcactgtc
661 caagatccag caactacatc ctccatctct ctagtctggt accacactgc tttctcccta
721 gtgatgtgcc tcctgtttgc agtggacacg gcctttatt tctacgtacg gagaaatctt
781 caaaccccga gggagtactg gaggaagtcc ctgtcaatca gaaagcacca ggctcctcaa
841 gacaagtgac accccatcca tcctatggca aaacatacga tgttttggtg gcagcagcaa
901 cttttcagcc acacagcctt cctttgaaag caacttacaa gcaggccggg atgtttggtt
961 cttcaatcac aacgacttag gatcaccagt tcaaggcttg ctgggtcaca cagagagagt
1021 gagtgcaagt ctagcctgga taacccagtg agatcctggg tttaggcggc tcatcaggaa
1081 agagaacctg ttgctaatct cacaaacaag atgcctactg cccatgtggc caaaggagag
1141 aacaaggtcc tggaagttgt cctctgacct ccaccatcca ccatggcagg tgcacacaat
1201 aaattaaaat gtcatgtata tttttaaaca agagacaggg gcaggctaag ggttgatggc
1261 atagctgtta tccagtacac ataatgccct gggtttgacc tcctataata aagc
```

Figure 22E

CD16 alpha chain-B

MWQLLLPTALLLLVSAGMRTEDLPKAVVFLEPQWYSVLEKDSVT
LKCQGAYSPEDNSTQWFHNESLISSQASSYFIDAATVNDSGEYR
CQTNLSTLSDPVQLEVHIGWLLLQAPRWVFKEEDPIHLRCHSWK
NTALHKVTYLQNGKDRKYFHHNSDFHIPKATLKDSGSYFCRGLV
GSKNVSSETVNITITQGLAVSTISSFSPPGYQVSFCLVMVLLFAVD
TGLYFSVKTN

```
  1 tctttggtga cttgtccact ccagtgtggc atcatgtggc agctgctcct cccaactgct
 61 ctgctacttc tagtttcagc tggcatgcgg actgaagatc tcccaaaggc tgtggtgttc
121 ctggagcctc aatggtacag cgtgcttgag aaggacagtg tgactctgaa gtgccaggga
181 gcctactccc ctgaggacaa ttccacacag tggtttcaca atgagagcct catctcaagc
241 caggcctcga gctacttcat tgacgctgcc acagtcaacg acagtggaga gtacaggtgc
301 cagacaaacc tctccaccct cagtgacccg gtgcagctag aagtccatat cggctggctg
361 ttgctccagg cccctcggtg ggtgttcaag gaggaagacc cattcacct gaggtgtcac
421 agctggaaga acactgctct gcataaggtc acatatttac agaatggcaa agacaggaag
481 tattttcatc ataattctga cttccacatt ccaaaagcca cactcaaaga tagcggctcc
541 tacttctgca gggggcttgt tgggagtaaa aatgtgtctt cagagactgt gaacatcacc
601 atcactcaag gtttggcagt gtcaaccatc tcatcattct ctccacctgg gtaccaagtc
661 tctttctgct ggtgatggt actccttttt gcagtggaca caggactata tttctctgtg
721 aagacaaaca tttgaagctc aacaagagac tggaaggacc ataaacttaa atggagaaag
781 gaccctcaag acaaatgacc cccatcccat gggagtaata agagcagtgg cagcagcatc
841 tctgaacatt tctctggatt tgcaacccca tcatcctcag gcctctc
```

Figure 22F

```
   1 aagcttccca tcctgttgca gtcccttact ctcctcctgt gctctctcct cttcttccta
  61 tctagcccac ccttttggta gctaagaatt cctccctcca ttggagagtc acagaccaaa
 121 gaggagtcaa ataagaaaat aagacctcaa agaaggaaaa caaagtgaag gccttgcatc
 181 agaagtcacg tggcagaaag ccacctggat atctgaaaag aagaaagaat tgagggatat
 241 ccgcttttg cctcagagac catccttagc cctgaaggct ttgtttctgc tttaggtttc
 301 ccagatgagc atctgaagtg ctacagcaag gaacttcaag tttccagata cttgtctgga
 361 ttttgcaagg cgtagatgag tcacttgaga aggagaactg gaatggcggc ctgggttcat
 421 ttccgttgtg caatccaagg gcctgtggag aaggggctgc tgcaagactc tgtgtgtggc
 481 aggggaggg gtgggtacgt ggatggcaat gggaggatca attaactcca cccaggagcc
 541 aaatgaaaca cacaaataaa aaacaaaacc tgagtagtgg ttttttaggtc attctggagt
 601 agaaagagca ttcatttata gcaaaggttg gcgggcacct gtgtcagccc ctgcctccac
 661 tccaccccta acaagtatca ggtgcccaca cgggcctgct gctcgcctcc tgggcttttc
 721 taagccaagt gagacctgtc ccagatgtcc acgaatccac tggggagtg gcactatcaa
 781 gcagagtcat ctgattttct gcctgggacc tggaccattg tgagagtaac caacatgggg
 841 ttacggggga gaatctggag agaagagaag aggttaacaa ccctcccact tcctggccac
 901 ccccctccac cttttctggt aaggagccct ggagccctgg agccctggct cctaggctga
 961 cagaccagcc cagatccagt ggcccggagg ggcctgagct aaatccgcag gacctgggta
1021 acacgaggaa ggtaaagagt tcctgtcctc accctcccc accccacct tttctgtgat
1081 cttttcagcc tttcactggt gacttgttct tccagggccc atttctctac cctacctggg
1141 tttcttctaa cctggaaatc taatgatcaa atcacactaa aaagtcagct cctgtggatt
1201 acatatccca ggagcatata gattttgaat tttgaatttt gaaagaaatt ctgcgtggag
1261 ataatattga ggcagagaca ctgctagtgg tcaaagattt gaaaggacaa ctttctgtgt
1321 gcaggcaggg cctcggctgg agatagatgg gtctggacga ggcaggagag tgagaagttc
1381 tgaggtgaaa tgcaggaagc cctcagagaa tgctcctccc accttgaatc tcatccccag
1441 ggtcttgctg tcccattctt ggtgctgggt ggatctaaat ccaggagatg ggggcaagca
1501 tctgggaaag ctgagggcac actctggcag attctgtgtg tgtcctcaga tgtcctcagccg
1561 cagacctttg ggggagtaaa gggggcacac ccacccacct tgcctccagg ctcttttcctt
1621 cctattcctg ttctatggtg gggctccatt gcgagacttc agattgagaa atcagatgaa
1681 gtttcaagaa aaggaaactg gcaggtgaca gagatgggtg gagggactgg ggaaaggctg
1741 tttactccct cctgtctagt cggcttggtc cctttagggc tccggatatc tttggtgact
1801 tgtccactcc agtgtggcat catgtggcag ctgctcctcc caactgctct gctacttcta
1861 ggtaagtcag gatatccctg gttgagggag aagtttgaga tgccttgggt tcatcagaga
1921 ccccttttca ggctacgaat gagactccca caaagggatg ggacccctca ccacatctat
1981 agctgtggat tgagctacca ggacaagcca agatggggct agaaatgagg agaatgctgg
2041 ttccaattgg gtcatagtca tgagtgaggc cagtcacttc acccctctgg gtcccagaat
```

FIGURE 22F
(CONT'D)

```
2101 cactatgtgg aactgaagag cttcgactag atggtccota gggtctgtct ctttcagttt
2161 gacattccag ggttctcctc tatggttttt aatttctacc ctttcttgtg gggatatggg
2221 ttgaggctgt ttctgtggct tggtttaggg aaattcaacc tgtaccctta atttgtgagt
2281 ttgcacaggg agcaaggggt aagggagcag tgttgaaaat agggatttgt gttgacagtg
2341 gcgcaagagg catgaacagt agagaccaga gagcaggtag caaggtttcc accagaaaca
2401 tcctgattct tgggaaaatt gggctcctgg ggcagaggag ggcaggggag ttttaaactc
2461 actctatgtt ctaatcactc tgatctctgc ccccactcaa tatttgattt actcttttt
2521 cttgcagttt cagctggcat gcggactggt gagtcagctt catggtcttg gattgaccca
2581 gtggggcaca tatggggaca atggccataa gatattggga aatgcttgtt gaatgggaaa
2641 atgctgatgt ggggttagca gggatagttc ctccaacaca gcagaacttg gccctgtgct
2701 tctctggcca gctttcctta agatactgaa caggccaaaa atggggccaa gatgctctaa
2761 gactgagcca ccaagcatgg gtttgcaatg agctcattct ggctttgagg ctccctggga
2821 atggcagtgt agagcctgct cctctccctg tcctcacccc acattatctt ggctcctcag
2881 aagatctccc aaaggctgtg gtgttcctgg agcctcaatg gtacagcgtg cttgagaagg
2941 acagtgtgac tctgaagtgc cagggagcct actccoctga ggacaattcc acacagtggt
3001 ttcacaatga gagcctcatc tcaagccagg cctcgag
```

Figure 22G

Murine FcgammaRIII 1 gtagttcatc tcctgaacct catcagactc tgatccagtt cttgaatgac tttggacacc
61 cagatgtttc agaatgcaca ctctggaagc caatggctac ttccaccact gacaattctg
121 ctgctgtttg cttttgcaga caggcagagt gcagctcttc cgaaggctgt ggtgaaactg
181 gacccccat ggatccaggt gctcaaggaa gacatggtga cactgatgtg cgaagggacc
241 cacaaccctg ggaactcttc tacccagtgg ttccacaacg ggaggtccat ccggagccag
301 gtccaagcca gttacacgtt taaggccaca gtcaatgaca gtggagaata tcggtgtcaa
361 atggagcaga cccgcctcag cgaccctgta gatctgggag tgatttctga ctggctgctg
421 ctccagaccc ctcagcgggt gtttctggaa ggggaaacca tcacgctaag gtgccatagc
481 tggaggaaca aactactgaa caggatctca ttcttccata atgaaaaatc cgtgaggtat
541 catcactaca aaagtaattt ctctatccca aaagccaacc acagtcacag tggggactac
601 tactgcaaag gaagtctagg aagtacacag caccagtcca gcctgtcac catcactgtc
661 caagatccag caactacatc ctccatctct ctagtctggt accacactgc tttctcccta
721 gtgatgtgcc tcctgtttgc agtggacacg ggcctttatt tctacgtacg gagaaatctt
781 caaaccccga gggagtactg gaggaagtcc ctgtcaatca gaaagcacca ggctcctcaa
841 gacaagtgac accccatcca tcctatggca aaacatacga tgttttggtg gcagcagcaa
901 cttttcagcc acacagcctt cctttgaaag caacttacaa gcaggccggg atgtttggtt
961 cttcaatcac aacgacttag gatcaccagt tcaaggcttg ctgggtcaca cagagagagt
1021 gagtgcaagt ctagcctgga taacccagtg agatcctggg tttaggcggc tcatcaggaa
1081 agagaacctg ttgctaatct cacaaacaag atgcctactg cccatgtggc caaggagag
1141 aacaaggtcc tggaagttgt cctctgacct ccaccatcca ccatggcagg tgcacacaat
1201 aaattaaaat gtcatgtata tttttaaaca agagacaggg gcaggctaag ggttgatggc
1261 atagctgtta tccagtacac ataatgccct gggtttgacc tcctataata aagc

FIGURE 23A

MTTPRNSVNGTFPAEPMKGPIAMQSGPKPLFRRMSSLVGPTQSF
FMRESKTLGAVQIMNGLFHIALGGLLMIPAGIYAPICVTVWYPLWGGIMYIISGSLLA
ATEKNSRKCLVKGKMIMNSLSLFAAISGMILSIMDILNIKISHFLKMESLNFIRAHTP
YINIYNCEPANPSEKNSPSTQYCYSIQSLFLGILSVMLIFAFFQELVIAGIVENEWKR
TCSRPKSNIVLLSAEEKKEQTIEIKEEVVGLTETSSQPKNEEDIEIIPIQEEEEEETE
TNFPEPPQDQESSPIENDSSP"

FIGURE 23B

```
   1 agtgtgcttg agaaacaaac tgcacccact gaactccgca gctagcatcc aaatcagccc
  61 ttgagatttg aggccttgga gactcaggag ttttgagagc aaaatgacaa cacccagaaa
 121 ttcagtaaat gggactttcc cggcagagcc aatgaaaggc cctattgcta tgcaatctgg
 181 tccaaaacca ctcttcagga ggatgtcttc actggtgggc cccacgcaaa gcttcttcat
 241 gagggaatct aagactttgg gggctgtcca gattatgaat gggctcttcc acattgccct
 301 gggggggtctt ctgatgatcc cagcagggat ctatgcaccc atctgtgtga ctgtgtggta
 361 ccctctctgg ggaggcatta tgtatattat ttccggatca ctcctggcag caacggagaa
 421 aaactccagg aagtgtttgg tcaaaggaaa aatgataatg aattcattga gcctctttgc
 481 tgccatttct ggaatgattc tttcaatcat ggacatactt aatattaaaa tttcccattt
 541 tttaaaaatg gagagtctga attttattag agctcacaca ccatatatta acatatacaa
 601 ctgtgaacca gctaatccct ctgagaaaaa ctccccatct acccaatact gttacagcat
 661 acaatctctg ttcttgggca ttttgtcagt gatgctgatc tttgccttct tccaggaact
 721 tgtaatagct ggcatcgttg agaatgaatg gaaaagaacg tgctccagac ccaaatctaa
 781 catagttctc ctgtcagcag aagaaaaaaa agaacagact attgaaataa aagaagaagt
 841 ggttgggcta actgaaacat cttcccaacc aaagaatgaa gaagacattg aaattattcc
 901 aatccaagaa gaggaagaag aagaaacaga gacgaacttt ccagaacctc cccaagatca
 961 ggaatcctca ccaatagaaa atgacagctc tccttaagtg atttcttctg ttttctgttt
1021 ccttttttaa acattagtgt tcatagcttc caagagacat gctgactttc atttcttgag
1081 gtactctgca catacgcacc acatctctat ctggccttg catggagtga ccatagctcc
1141 ttctctctta cattgaatgt agagaatgta gccattgtag cagcttgtgt tgtcacgctt
1201 cttcttttga gcaactttct tacactgaag aaaggcagaa tgagtgcttc agaatgtgat
1261 ttcctactaa cctgttcctt ggataggctt tttagtatag tatttttttt ttgtcatttt
1321 ctccatcagc aaccagggag actgcacctg atggaaaaga tatatgactg cttcatgaca
1381 ttcctaaact atctttttt tattccacat ttattacgttt ggtggagtcc cttttgcatc
1441 attgttttaa ggatgataaa aaaaaaaaaa aaa
```

FIGURE 23C

```
   1 tgttaaacca aagtaattgg agcgaagccc agggtagcag aagctactga tttcctgtca
  61 cctgatgtct atcagcgatt tcatcttcag gcctggacta caccactcac cctcccagtg
 121 tgcttgagaa acaaactgca cccactgaac tccgcagcta gcatccaaat cagcccttga
 181 gatttgaggc cttggagact caggtaagga atcaatttgc tttctttaaa tgacttaaag
 241 gaggtgatgg ataaggtata gaatggtttt gaagactgga ggttcttgat cttaattcta
 301 gagtttccct agtcagactt cctaatagtt ctatgactta aggaggggtg acgatatcaa
 361 ggcttgctgc ccactcactc ctctaatcag tctccctctc aacaattacc ctatgcagtc
 421 aactgtgaat cattccacaa aagtagtaga ttgcagcata tatattaaat catggtttct
 481 aaaccattgg gttcgaactg gagctctacc actaacaaac aatataacct tgggcaaatt
 541 actaacctct aagcctcagc ttcctcatcg ttaacttatt tatgtcttac atctcagaga
 601 ggggtactgt tctaacttta cagaaggata aaatcgaaac taatgctcag caaagtacaa
 661 agaacaagaa tagcaacaaa aataactatt tattccaaca tgggttcttt gcatacattt
 721 atttcttcaa taatatttat taagaagtaa ctaaatccaa aaattatttt agatcctgaa
 781 caagagagaa caaaatctct acttttgatgg aacttccatt ctgtggggaa gagactgaca
 841 ataagcaatt aaataaataa ggtaatttcc tacagtgatc aatgccgtaa agcaattaag
 901 ataggatttt gtaaaagaca gcaaatagga gtacatgtta tagattgagg gttcaaggta
 961 ggctcctcta ggagctgaca tttgagctac acctgaacaa aaagacacta gccatgcaca
1021 gaccatgagc ccagttaagt gttatagcag cccacgagat aagaattatt attatttcaa
1081 ttttacagtt gaacctgagg cccagagaat ttaaagaact tgcccaacat ctcagaacaa
1141 atggaggaat cactattgaa acctgggcaa tctgactcag gaggccacag tcttatatac
1201 tgacattaga aagccttaga gagccttttc tttttctttg agaccgagtc tcactctgtt
1261 acccaggctg gaatgcagtg gcatgatctc agctcactgc aacctctgcc tcctaggttc
1321 aagcaattct cctgccttag cctcccgagt agctgggatt acaggtgcac accaacatgc
1381 ctggctaatt tttgtatttg tagtagagat ggggttttgc catgttagcc agcccggtct
1441 caaactcctg acctcaggtg atctgcccat cttggcctcc caaagtgctt ggattacagg
1501 catgagccac cgtgcccgac ctagagagcc ttcttgatgt gacttgcaca aggtggcaga
1561 gttagagaca gagagaggcc tggaatcgac ccctcctgct tctacagata gtccttacca
1621 tactctgcaa tgttgcctct ggccatcata atgcacaaag gcagataagc aaaaggacaa
1681 ggacaagtcc attgaaaata cattttcaa tattaaagca aagaaaagc atccaggaat
1741 aagaaacaaa gaggacatgc agtcatatat gcaaggtgtc ctctacaaag ataaagaatg
1801 cccccaaacccc agttgtcaag atcactggca gggactcctg ggcccacatg ctcttcctaa
1861 acaaccccctc catctccttt ctcagaactc agcagtaggc cttgcctcag atccaaggtc
1921 actcggaaga ggccatgtct accctcaatg acactcatgg aggaaatgct gagagaagca
1981 ttcagatgca tgacacaagg taagactgcc aaaaatcttg ttcttgctct cctcattttg
2041 ttatttgttt tatttttagg agttttgaga gcaaaatgac aacacccaga aattcagtaa
```

FIGURE 23C
(CONT'D)

```
2101 atgggacttt cccggcagag ccaatgaaag gccctattgc tatgcaatct ggtccaaaac
2161 cactcttcag gaggatgtct tcactggtgg gccccacgca aagcttcttc atgagggaat
2221 ctaagacttt gggggtaagt cagttgcctt ccatcccatg tcgtagggat tctctggctg
2281 acagaagctg atgcggtata ggtcacatac agaattcaat ccaatttgaa gaattgggat
2341 ccaacctgat gtcttcttta tgtctaacac agtgggccaa atcagggtg catcagagaa
2401 gttatcactt agatcacctc tgggtgatct tatgtcacct tttggttttg gggcttgtat
2461 atgcaggggt tcccccattc ccagttccat ttgccagaat cccaggcata cctgctccct
2521 ggaaatgccc catgtggttg aggaaacaga ttcgaacaag aaaaagacaa aattcttggc
2581 acctccactg cttcctttag gcattcctca cagctccaag tcaggagcca gagcttccaa
2641 ccttgtctttt gcctgctagc agtgatgatt tcagctcatc cactgctgcc tctgttctct
2701 ccccaggctg tccagattat gaatgggctc ttccacattg ccctgggggg tcttctgatc
2761 atyccagcag ggatctatgc acccatctgt gtgactgtgt ggtaccctct ctggggaggc
2821 attatggtga gtaaaagaat agcagccatt tgggaaatgg tgcagacaaa aatgttaaaa
2881 ggctccacag ggatatgcca gattatttct gtgttgaggg aaatatatga gtaggaaata
2941 ttattgggtt aaagtaatta agaagacagg ttgaccaaat tgagtataaa tccatggtt
3001 gagagtcagt ggtcctgttt catgtgaatt cagagaaagg ggccctgcat ggatctcaca
3061 gggactgtcc aaagcaagaa ctctccaaag tcagttctgg tggggagggt ggccctagac
3121 atttagacta gatagcaaga tgttttggaa agcaagaggc agcaggaaca tccacttcca
3181 tctaccccctt cttgcttaca attctgtttg gttactatgg tacctggtga aacctgtccc
3241 atcacaagtc agtctcattt tgcttatcga cagagcagca ctcttttgac gttttatgta
3301 catgttttcc aaatctgtaa ccctgtctgg gtgtgatttg agttctgtct ctttggtctt
3361 actatattcc tgtcacagat ccccagatga ttgagtaaaa ggcatgaatt tagtgtcact
3421 gagcctgaat aaaggaggaa tatgacagct gaaaaatgaa tacaactgat aaaaatgggt
3481 ggatggttgt gtgaaagttg ctgaaagtgt aggcttcttt ctgaccagtt atcaatgtta
3541 aaaagtgatc tcctctctcc tctatctcct gtcttgccca cccctctcc atctccccca
3601 cctctctttt ttacagtata ttatttccgg atcactcctg gcagcaacgg agaaaaactc
3661 caggaagtgt ttggcaagta accatatgtc cttctttccc acatgtcaga gaagtaccta
3721 ttttttttcgg ttaaaaactg agacccttaa aaagccatgg tatcacagcc tctcagccct
3781 aaaaagcaaa gaccctccac aatgttattg tgattttatt tatgaaaaac ttagaagcga
3841 gatcatctga agtatgttca tgggaacaga actaaaagca gatccatgaa aaccataccct
3901 acagtcttaa gaacgttaaa tgctgtgtga aaataataga cctttcngaa gccctatcat
3961 ttctcccaga tcaccatttta ggaaattatc tgatcaatgt catgattgat tcaaaattct
4021 agctaagcca tttttggtc gtaacattga acaagtcagt ttacctctat gttcctgagt
4081 tttcacctgg aaaggaaggg taacagtcct tgctaccatg tgacgtccaa tggagtgaag
4141 gcagtagagt gtgtgatggt gcttcacagg actataggta ctacactgtg gtcttgccca
4201 taaaacccct ggggaactca tatagatcca gaggaaactg gctgcaggcg cgagcgatgg
4261 gtgaaaagag tttagcagca agttcgctcc caaaaaattc ctcccccaac actgttacta
```

FIGURE 23C
(CONT'D)

```
4321 aactgtgtca cttcataatc aatgagggaa tgggtggatt gagatggttc cttgtcttaa
4381 agtgacctga cacactcagt ttgggggaa aacttttat gaacatcaaa ttattctcta
4441 gatacagcca gatttactga cttgccatgt gtaggtcata gagctaggaa tgaaatatgc
4501 gcaacataaa ataataatca ataatcccat atcattatgg tacttgttat ttatattttc
4561 ctgtttcaac cttttatcat ccctgcaagg tagaacattc acactgatat tctcttacct
4621 atgctaccca aagacatcag ccctaattgt attttggaag atagctgact ggggctgatt
4681 gcagcctatg tcagcaggaa tagatgttgt tactgttgtt gcttctgctt tttttatttc
4741 catttatttg atagtacaga tctagagggt tctatctgaa ccttcccaac ctatacttca
4801 taataccatc ccactaaagt gtgatacaag aaacttcttc actctcttcc ctctacctat
4861 ttatgaaggc agataataaa ctggataata tttatcttca cttattcaac aaacatttat
4921 tgagtgccta ctaggatggt ggcagtggca gtgaaggaaa tgcaaggata caagatatag
4981 aatcaagggt tactcttaga atttttgctt tataaaacag atggatggtg aatgagatag
5041 ggaagactga gaaaacaaca ggatagagac atgattttat tttatagtga caaagaggct
5101 aaaaagaact gagagaactt cagtatattt agttgtagtt gctttgtgag tcagggcagt
5161 tgcatttgga attccctccc agattatgtt ttccaaaggg aaatcaaacc caattaataa
5221 atctgtgtct ccatttcagg tcaaaggaaa aatgataatg aattcattga gcctctttgc
5281 tgccatttct ggaatgattc tttcaatcat ggacatactt aatattaaaa tttcccatttt
5341 tttaaaaatg gagagtctga attttattag agctcacaca ccatatatta acatatacaa
5401 ctgtgaacca gctaatccct ctgagaaaaa ctcccatct acccaatact gttacagcat
5461 acaatctctg ttcttggtaa gtgttcttgg taagtgtgag attggatttc tctccaggga
5521 ggaaggatga cttgtttatt atgagccatga actctgaatt ccagaccacc tgtgtttgtc
5581 tgcttcaact gattattcat accttacttt ctatcagcaa tacacattaa ccatctgttg
5641 tgtgccaaaa gttgtgttaa gagttagggt tataaagatg ctgtctcctg tactagcagt
5701 tctcacagct attcattact tgtctaaaga attgatctct taatcgttca attatagtca
5761 acaataactt actgaacacc aacaatgttc tttgtgccat tattacattt tcaccttcat
5821 tcttctgttg tttttcaggg catttgtca gtgatgctga tctttgcctt cttccaggaa
5881 cttgtaatag ctggcatcgt tgagaatgaa tggaaaagaa cgtgctccag acccaaatct
5941 gtaagtagta gcctccagca ccgtggtcaa tgtctgctgc ccttgaagat ttattcagac
6001 ttgagttta ataatgact tgataaggat ataagcacct gcaaaaaat tttggcattt
6061 aaaggcatat aataaatgac ataagtagca taaaaaccag gaggtatttg ataaatgttt
6121 gtggagattg ttgacaaagg tgtcagttgt aaaagtaaag aatggtttgt ttaatttct
6181 gttttagaac atagttctcc tgtcagcaga agaaaaaaaa gaacagacta ttgaaataaa
6241 agaagaagtg gttgggctaa ctgaaacatc ttcccaacca aagaatgaag aagacattga
6301 aattattcca atccaagaag aggaagaaga agaaacagag acgaactttc cagaacctcc
6361 ccaagatcag gaatcctcac caatagaaaa tgacagctct ccttaa
```

FIGURE 23D

Mouse CD20

```
   1 gaattccttt tttttttttt tttttaaaga tttatttatt attatatgta agtacactgt
  61 agctatcttc aagtacttga gatagaagag gccaactgat ctcagctgtg agtggctaat
 121 ttggcccttg agccttggag ccttggagcc ttggagaccc aggcgtttga aaactcaatg
 181 agtggacctt tccagcaga gcctacaaaa ggtcccctcg ccatgcaacc tgctccaaaa
 241 gtgaacctca aaaggacatc ttcactggtg ggcccacac aaagcttctt catgagggaa
 301 tcaaaggctt tggggctgt ccaaatcatg aatggcctct tccatattac cctggggga
 361 ctgctgatga tccccacagg ggtcttcgca cccatctgtt tgagtgtatg gtaccctctc
 421 tggggaggca ttatgtacat tatttcagga tcactcctgg cagctgcagc agaaaaaacc
 481 tccaggaaga gtttggtcaa agcaaaagtg ataatgagct ctctaagcct ctttgctgcc
 541 atttctggaa taattctttc aatcatggac atacttaaca tgacactttc tcatttttta
 601 aaaatgagaa gactggagct tattcaaact tccaagccgt atgttgatat ctacgactgt
 661 gaaccatcta attcctcaga gaaaaactcc ccatctacac agtactgtaa cagcattcag
 721 tctgtgttct tgggcattct gtcggcgatg ctgatctctg ccttcttcca gaaacttgtg
 781 acagctggta ttgtggagaa tgagtggaaa agaatgtgta ccagatccaa atctaatgtg
 841 gttctgctgt cagctggaga aaaaaatgag cagacgatta aatgaaaga agaaatcatt
 901 gagctaagtg gagtatcttc ccaaccaaag aatgaagagg aaattgaaat tattccagtg
 961 caggaggaag aagaagaaga agcagaaata aattttccag cacctcccca agagcaggaa
1021 tccttgccag tggaaaatga gatcgctcct taaactcttt tcttttctaa gcattattgt
1081 ttagagagct tccaagacac atagttaccc tcatctcttg tggccttcca caatctattc
1141 tccatatttt cacagcttaa ctttgcatag agaagccaca tctagctctc cttcacattt
1201 gaagaatgca gtgattataa aagattgtct tttgccttgc ttagggagtc ttacactggc
1261 agaaacgctg aagaatccaa ttctcattca ccttttcctt ggatgtgtgt ctcagtagtg
1321 gtaatggttt ttccgcatt cctccatcag cagttacagc agaaggagtc agagagttca
1381 gggaattc
```

Macrophages and natural killer cells express transgenic human CD16

Figure 25A

Fc Receptor gamma Chain 1 mipavvllll llveqaaalg epqlcyilda ilflygivlt llycrlkiqv rkaaitsyek
61 sdgvytglst rnqetyetlk hekppq

Figure 25B 1 cagaacggcc gatctccagc ccaagatgat tccagcagtg gtcttgctct tactcctttt
61 ggttgaacaa gcagcggccc tgggagagcc tcagctctgc tatatcctgg atgccatcct
121 gtttctgtat ggaattgtcc tcaccctcct ctactgtcga ctgaagatcc aagtgcgaaa
181 ggcagctata accagctatg agaaatcaga tggtgtttac acgggcctga gcaccaggaa
241 ccaggagact tacgagactc tgaagcatga gaaccacca cagtagcttt agaatagatg
301 cggtcatatt cttctttggc ttctggttct tccagccctc atggttggca tcacatatgc
361 ctgcatgcca ttaacaccag ctggccctac ccctataatg atcctgtgtc ctaaattaat
421 atacaccagt ggttcctcct ccctgttaaa gactaatgct cagatgctgt tacggatat
481 ttatattcta gtctcactct cttgtcccac ccttcttctc ttccccattc ccaactccag
541 ctaaaatatg ggaagggaga accccaata aaactgccat ggactggact c

FACS staining of mouse CD16

Expression of mouse CD64 in peripheral blood of CD16-/- mice

Human CD20 expression in peripheral blood

TRANSGENIC MICE EXPRESSING HUMAN CD20 AND/OR CD16

This application is being filed as a PCT International Patent Application in the name of Genentech, Inc., a U.S. national corporation and resident, (Applicant for all countries except U.S.); Andrew Chee-Yuen Chan, a U.S. citizen and resident (Applicant for U.S. only); Qian Gong, a Chinese citizen and U.S. resident (Applicant for U.S. only); and Flavius Martin, a Romanian citizen and U.S. resident (Applicant for U.S. only), on 11 Dec. 2003, designating all countries and claiming priority to U.S. provisional application Ser. No. 60/434,115, filed Dec. 16, 2002, and U.S. provisional application Ser. No. 60/476,481, filed Jun. 5, 2003.

BACKGROUND OF THE INVENTION

T and B cells both comprise cell surface proteins that can be utilized as markers for differentiation and identification. One such human B cell marker is the human B lymphocyte-restricted differentiation antigen Bp35, also known as "CD20". CD20 is expressed during early pre-B cell development and remains until plasma cell differentiation. It is believed that the CD20 molecule regulates a step in the activation process that is required for cell cycle initiation and differentiation and is usually expressed at very high levels on neoplastic B cells.

CD20 is present on both normal B cells as well as malignant B cells, whose unabated proliferation can lead to B cell lymphoma. Thus, the CD20 surface antigen has the potential of serving as a candidate for targeting of B cell lymphomas with antibodies specific to the antigen. These anti-CD20 antibodies specifically bind to the CD20 cell surface antigen of both normal and malignant B cells, leading to the destruction and depletion of B cells. Chemical agents or radioactive labels having the potential to destroy the tumor can be conjugated to the anti-CD20 antibody such that the agent is specifically delivered to the neoplastic B cell.

The use of monoclonal antibodies targeting CD20 has been described (see, for example, Weiner, Semin. Oncol., 26, 43-51 (1999); Gopal and Press, J. Lab. Clin. Med., 134, 445-450 (1999); White et al., Pharm. Sci. Technol. Today, 2, 95-101 (1999). Rituxan™ is a chimeric anti-CD20 monoclonal antibody that has been used widely both as a single agent and together with chemotherapy in patients with newly diagnosed and relapsed lymphomas (Davis et al, J. Clin. Oncol., 17, 1851-1857 (1999); Solal-Celigny et al., Blood, 94, abstract 2802 (1999); Foran et al., J. Clin. Oncol., 18, 317-324 (2000). The use of radiolabeled antibody conjugates has also been described (for example, Bexxar™; Zelenetz et al., Blood, 94, abstract 2806 (1999)).

The interaction of antibody-antigen complex with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc domain of antibodies or immune complexes to specialized cell surface receptors on hematopoietic cells. It is now well established that the diversity of cellular responses triggered by antibodies and immune complexes results from the structural heterogeneity of Fc receptors (FcRs).

One group of these receptors, FcγRs, is found on most cells of the hematopoietic lineage, and mediate both high and low affinity binding to IgG (see, for example, U.S. Pat. No. 5,877,396, incorporated herein by reference). The high affinity receptor, FcγRI, binds monomeric IgG and is expressed exclusively on macrophages and neutrophils. It is capable of mediating antibody-dependent cell-mediated cytotoxicity (ADCC) and phagocytosis in response to crosslinking by antibody. The low affinity receptors for IgG, FcγRII and FcγRIII (CD16), are responsible for effector cell responses to immune complexes and represent the FcγRs primarily involved in the inflammatory response in vivo. FcγRII is widely expressed on haematopoietic cells and functions as an inhibitory receptor on B cells, while on cells of the myeloid lineage and on platelets, FcγRII triggers ADCC, phagocytosis and the release of inflammatory mediators when crosslinked by immune complexes. FcγRIII is expressed on various leucocytes including natural killer (NK) cells, macrophages, neutrophils, eosinophils, basophils and mast cells, and mediates effector responses when crosslinked by immune complexes. It is the sole FcR on NK cells, mediating all the antibody-dependent responses on those cells. Natural killer cells are a subset of spontaneously cytotoxic lymphocytes that lytically destroy tumor cells without apparent antigen specificity or restriction by histocompatibility molecules. In addition to these well-characterized effector cell pathways, FcγRIII has been found on immature thymocytes, where it has been postulated to function in early thymocyte development.

With other receptors of the immunoglobulin Fc portion (eg. FcγRI, FcγRII, FcεRI), CD16 plays an important role in mediating autoimmunity and inflammatory responses. Studies using monoclonal antibodies against CD16 have established this receptor's role in removing immune complexes from circulation and in mediating ADCC (see for example Van de Winkel et al., Immunol. Today, 14, 215-221 (1993)). The binding of IgG with CD16 elicits NK/LGL cell activation and triggers ADCC. ADCC can be halted in the presence of high levels of soluble CD16.

It has been found (see Mathiot et al., J. Clin. Immunol., 13, 41-8 (1993)) that the level of soluble CD16 was significantly decreased in patients with multiple myeloma compared with healthy volunteers. In addition a stage-dependent decrease of soluble CD16 was observed, with a highly significant difference between stage I and stages II+III myeloma patients. Therefore, measurement of soluble CD16 in serum is both a diagnostic and a prognostic marker of myeloma, which can be useful to define and guide novel immunomodulatory therapies of the disease.

It has further been found that CD16 is present in human serum and other body fluids and is elevated at sites of inflammation (see Fleit et al., Blood, 79, 2721-8 (1992)). It appears that there are at least two forms of human CD16, type A and type B. CD16-A is expressed predominantly on the surface of macrophages, natural killer cells and large granular lymphocytes (NK/LGL), whereas CD16-B is expressed predominantly on the surface of neutrophils and monocytes.

In spite of the significant roles of CD20 and CD16 in human lymphoma and in inducement of important immunological responses, animal models are lacking which co-express the human markers. Thus, a need exists for relevant animal models for disease study and pharmaceutical drug development.

SUMMARY OF THE INVENTION

The present invention generally relates to non-naturally occurring non-human transgenic animals expressing human cellular markers, specifically, CD16 and CD20. In one aspect, the transgenic animals provide a system to identify and test novel therapeutic agents for CD20 associated disease or conditions, such as cancer. In an embodiment, the transgenic animals are useful to test efficacy and toxicities of CD20 directed therapies.

The invention provides a non-naturally occurring transgenic animal whose genome comprises a nucleotide sequence encoding a heterologous CD20, preferably, human CD20. The nucleotide sequence is preferably operably linked to a human endogenous promoter whereby the human CD20 is expressed on the surface of B lymphocytes. In one embodiment, the human CD20 trangenic mice are characterized by expression of human CD20 on cells at a level sufficient for anti-human CD20 antibody bound to the expressing cells to affect killing of the cells, resulting in B cell depletion of peripheral and/or circulating B cells of at least about 75% and more preferably, 80%, 85%, 90%, 95%, 99% and even 100%.

In one embodiment of the invention, the genome of the non-naturally occurring non-human transgenic animal further comprises a nucleotide sequence encoding a heterologous FcγIII receptor, preferably, human CD16 and preferably, the α chain of human CD16. The nucleotide sequence is preferably operably linked to a human endogenous promoter, whereby the heterologous receptor is expressed on the surface of leukocytes, including one or more of the following: natural killer (NK) cells, macrophages, neutrophils, eosinophils, basophils, thymocytes, and mast cells.

According to a preferred embodiment, when the genome of the animal comprises a homologous endogenous gene (either CD20 or CD16, or both), the gene is disrupted or knocked out such that endogenous molecule is not expressed on cell surfaces.

The present invention further provides methods of identifying agents capable of treating B cell lymphoma where the method comprises administering an agent to a transgenic animal that expresses human CD20 on B lymphocytes and determining whether there is a reduction in the number of B lymphocytes. The invention also provides methods of identifying agents capable of depleting or killing cells expressing human CD20 comprising administering an agent to transgenic animals that express human CD20 and determining whether there is a reduction in the number of such cells. Further provided are agents identified according to such methods.

The animal models of the present invention may also be used to identify agents capable of inducing effector cell responses such as ADCC or NK cell mediated immune responses. After administration of the agent, the animal can be monitored for an immune response such as by determining increase or decrease in cytokine levels. An increase in levels of cytokines after administration of the agent identifies an agent that induces a Fc-mediated effector cell response. Binding of the putative agent to CD16 can also be assessed using suitable markers or labels. Additionally, agents can be screened for their ability to affect depletion of B cells expressing human CD20 (including malignant cells) via CD16 mediated immune response by comparing B cell depletion in the CD20$^+$ transgenic animal with that in the CD16$^+$CD20$^+$ transgenic animal after administration of an agent. The animals of the present invention are also useful for assessing the toxicity of anti-CD20 therapeutics by administration to the presently described transgenic animals.

Treatment specificity, toxicity and efficacy can also be determined by comparison of the agent's effect with that in a wild-type animal or untreated transgenic animal. A non-human transgenic animal of the present invention can further provide an indication of the safety of a particular agent for administration to a human. For example, a humanized antibody or other agent can be administered to the transgenic animal and any toxic or adverse effects as a result of the administration of the agent to the animal can be monitored as an indication of the safety and tolerability of the humanized antibody or agent for in vivo human use. Adverse events that may occur on a short term basis include headache, infection, fever, chills, pain, nausea, asthenia, pharyngitis, diarrhea, rhinitis, infusion reactions, and myalgia. Short term adverse events are measured in days post treatment. Long term adverse effects include cytoxicity of certain cell types, bleeding events due to thrombocytopenia, release of mediators due to inflammatory and/or allergic reactions, inhibition of the immune system and/or development of an anti-therapeutic agent antibody, end organ toxicity, and increased incidence of infection or malignancy. Long term adverse events are measured in months post treatment.

Another aspect of the invention involves a method for determining efficacy of an anti-CD20 agent. Efficacy can be determined by administering a range of doses of the agent to set of trangenic animals having human CD20 and/or human CD16 alpha chain, determining at least one dose of the agent that results in a decrease in cells bearing human CD20.

| | |
|---|---|
| control mAb: | 200 ug/ip, 3 ip/week, for 1 week |
| PK-136: | 200 ug/ip, 3 ip/week, for 1 week |
| anti-CD20 mAb: | 10 ug/ip, single dose |

NK cells from peripheral blood, liver and spleen were analyzed after treatment with antibodies. Data is expressed as mean+/−standard error, with n=8.

Figure 20:
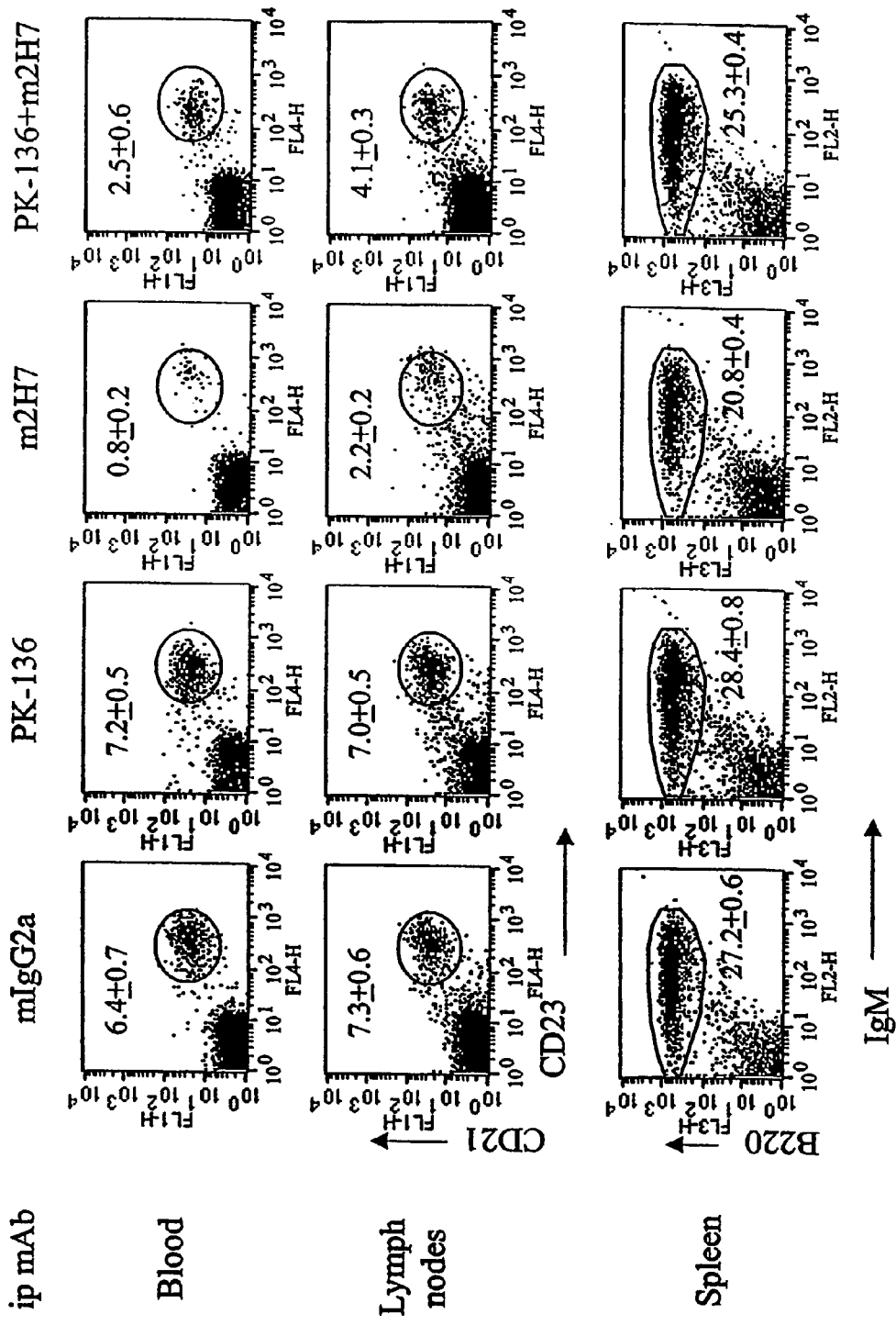

FIG. 20 shows that NK cells play a role in 2H7 mediated B cell depletion in Tg+ mice. Hybridoma clone, which produces PK-136 mAb (specific against mouse NK1.1), was obtained from ATCC. Four groups of human CD20 transgenic mice were injected ip with control mAb, PK-136, anti-CD20 mAb and the combination of PK-136/anti-CD20, respectively. Doses administered ip were as follows:

| | |
|---|---|
| control mAb: | 200 ug/ip, 3 ip/week, for 1 week |
| PK-136: | 200 ug/ip, 3 ip/week, for 1 week |
| anti-CD20 mAb: | 10 ug/ip, single dose |

Lymphocytes from peripheral blood, lymph nodes and spleen were analyzed 3 days after anti-CD20 mAb ip. Data is expressed as mean+/−standard error, with n=8.

Figure 21:
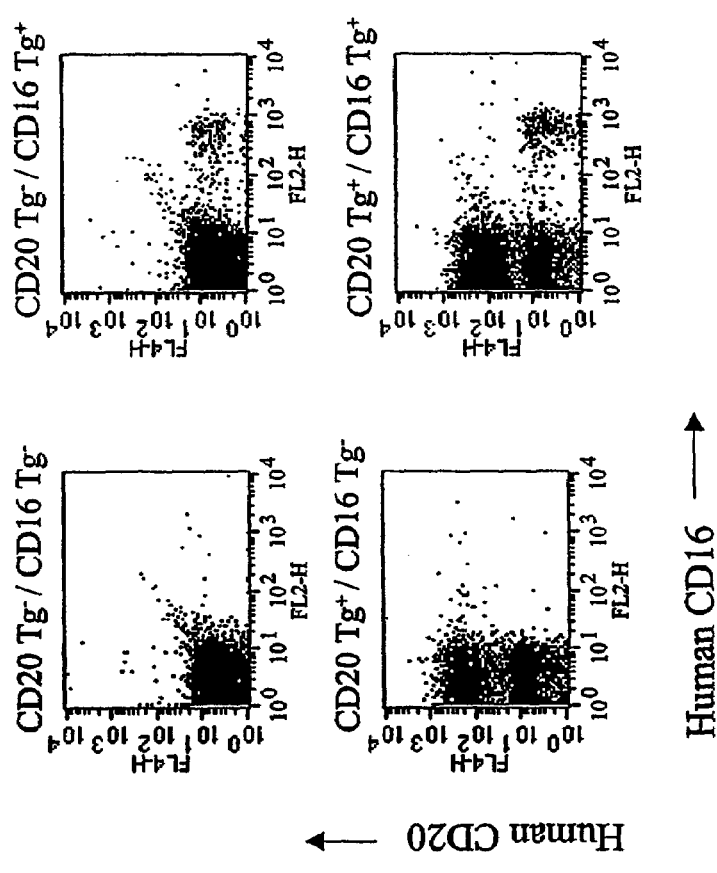

FIG. 21 shows the expression of human CD20 and human CD16 on different populations of cells in transgenic mice. Blood cells from CD20Tg−/Cd16Tg− (control mice), CD20Tg+/CD16Tg−, CD20Tg−/CD16Tg+, and CD20Tg+/CD16+ mice were stained with labeled anti-human CD20 antibodies labeled with FITC, anti-B220 antibody conjugated to PerCP and anti-human CD16 antibodies labeled with PE (BD Pharmingen) and analyzed by FACS. The results show that human CD20 is found on B cells and the human CD16 is found on cells that lack the B220 marker and therefore, are not B cells. Transgenic mice positive for both markers show both populations of cells.

FIG. 22A shows a representative amino acid sequence (SEQ ID NO: 1) (GenBank Accession No. NM000569), cDNA for human CD16 alpha chain isotype A (SEQ ID NO: 2) (GenBank Accession No. NM000569) (FIG. 22B) and a genomic DNA sequence for human CD16 alpha chain isotype A (SEQ ID NO: 3) (GenBank Accession No. Z46222) (FIG. 22C). FIG. 22D shows a representative cDNA sequence for mouse CD16 alpha chain (Gen Bank Accession No. NM010188) (SEQ ID NO: 9). FIG. 22E shows a representative amino acid sequence (SEQ ID NO: 10) and cDNA sequence for human CD16 α chain isotype B (SEQ ID NO: 11) (GenBank Accession No. NM000570). FIG. 22F shows a representative genomic sequence encoding human CD 16 α chain isotype B (SEQ ID NO: 12) (GenBank Accession No. Z46223). FIG. 22G shows a cDNA sequence encoding murine CD16 alpha chain (SEQ ID NO: 13) (GenBank Accession No. NM010188).

FIG. 23A shows an amino acid sequence for human CD20 (SEQ ID NO: 4) (GenBank Accession No. BC002807), cDNA sequence for human CD20 (FIG. 23B) (SEQ ID NO: 5) (GenBank Accession No. BC002807) and a genomic sequence for human CD20 (SEQ ID NO: 6) (GenBank Accession No. AH005353) (FIG. 23C). FIG. 23D shows a representative cDNA sequence for murine CD20 (SEQ. ID NO:14) (GenBank Accession No. M62541).

Figure 24:
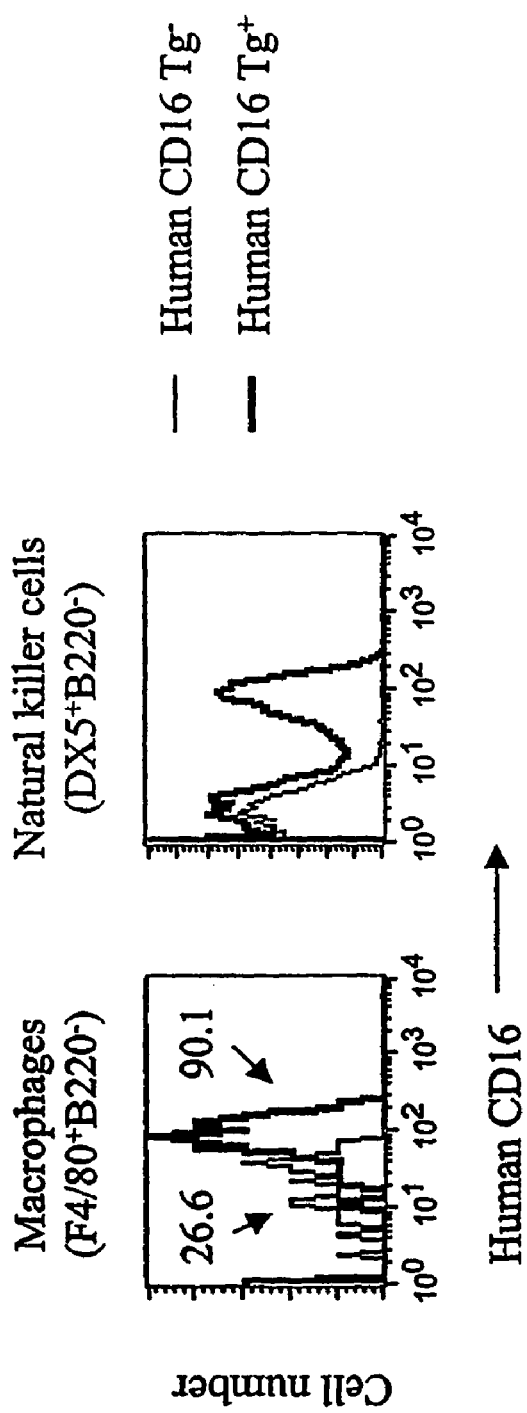

FIG. 24 shows a comparison of expression of human CD16 in human CD16Tg− mice to human CD16Tg+ mice. The cells were stained with anti-human CD16 conjugated to PE (BD Pharmingen) and were also stained with anti-DX5-FITC (BD Pharmingen) to identify NK cells or anti-F4/80 conjugated to APC (Allophycocyanin) to identify macrophages. The results show that both NK and macrophages express the human CD16 transgene in human CD16Tg+ mice.

FIG. 25 shows an amino acid (GenBank Accession No. P30273) (SEQ ID NO: 7) and cDNA sequence (GenBank Accession No. M33915) (SEQ ID NO: 8) for human Fc receptor gamma chain.

Figure 26:
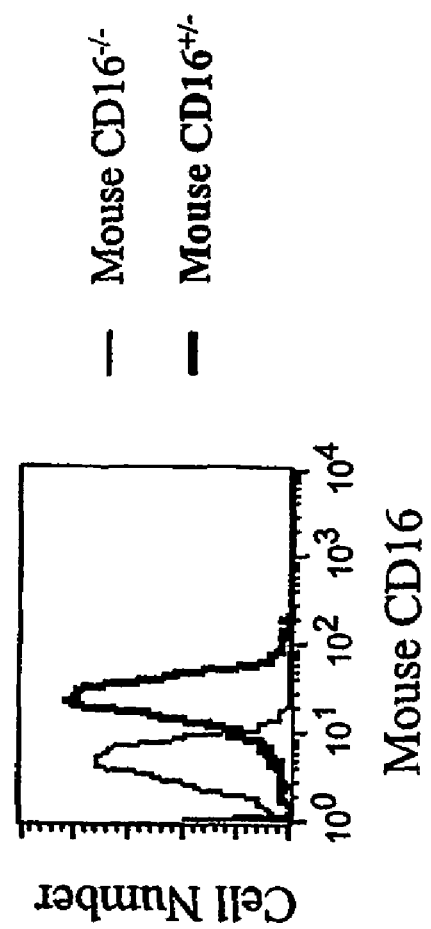

FIG. 26 shows an FACS analysis for the presence or absence of expression mouse CD16 on macrophages. Peripheral blood cells from mice lacking murine CD16 (CD16−/−) and from control mice having murine CD16 (CD16+/−) were stained with anti-mouse CD16 antibody. The cells were gated for expression of a macrophage marker mac-1 using anti-mac 1 antibodies.

Figure 27:
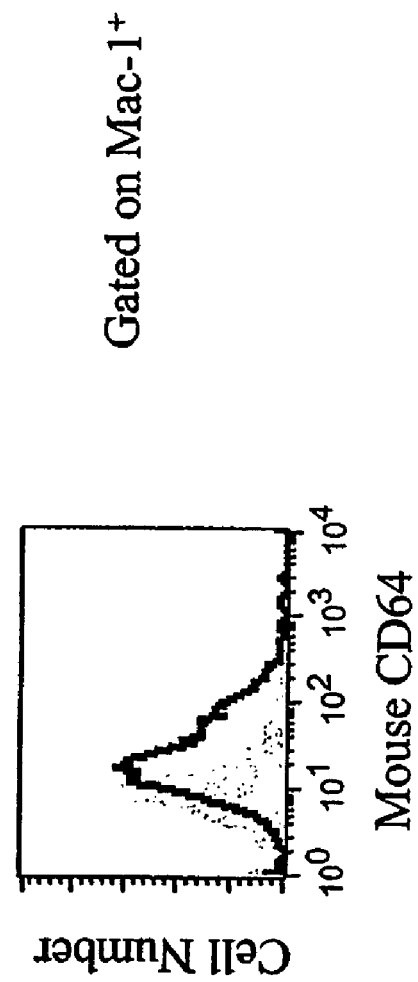

FIG. 27 shows a FACS analysis for the presence or absence of expression of mouse CD64 on peripheral blood cells from CD16−/− mice. CD64 is the Fcgamma RI and expression of this receptor on mouse cells shows that expression of other Fc receptors was not affected by knocking out the Fcgamma RIII (CD16) alpha chain. Peripheral blood cells from mice lacking murine CD16 (CD16−/−) and from isotype control mice were stained with anti-mouse CD64 antibody. The cells were gated for expression of a macrophage marker mac 1 using anti-mac 1 antibodies.

Figure 28:
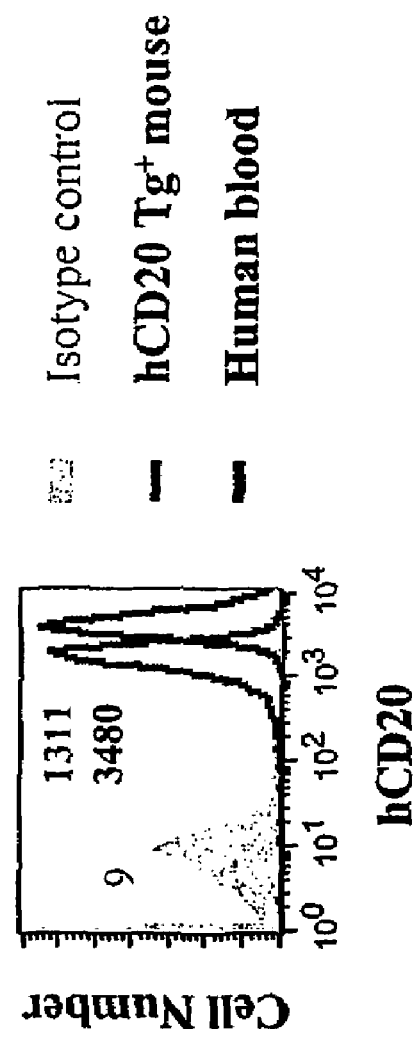

FIG. 28 shows a representative comparison of the expression level of human CD20 expression on peripheral blood cells from a human CD20 transgenic mouse as compared to expression of CD20 on human peripheral blood cells. Peripheral blood cells were obtained from a human donor and from a hCD20Tg+ mouse and stained with labeled anti-human CD20 antibody (mH27). The cells were analyzed by FACS and were gated on human CD19+ and B220+ populations. The numbers on the graph represent mean fluorescence intensity.

DETAILED DESCRIPTION

The following terms have the meanings ascribed to them below unless specified otherwise.

The term "construct" or "targeting construct" refers to a polynucleotide molecule that comprises a targeting region. A targeting region comprises a sequence that is substantially homologous to an endogenous sequence in a target tissue, cell or animal and that provides for integration of the targeting construct into the genome of the target tissue, cell or animal. Typically, the targeting construct will also include a gene or a nucleic acid sequence of particular interest, a marker gene and appropriate control sequences.

The term "CD16" or "FcγRIII" are used interchangeably and refer to a cell surface receptor protein for a Fc portion of an IgG immunoglobulin. This receptor is a low affinity receptor for IgG and preferentially binds IgG in immune complexes. FcγIII receptor is comprised of an α chain which serves as a ligand binding chain and a homodimer or heterodimer. When the FcγRIII is expressed on macrophages, the α chain is associated with a homodimer of the gamma chain. When the FcγRIII is expressed on natural killer cells, the α chain is associated with a heterodimer of the gamma chain with a delta chain. The gamma chain is involved in cell surface expression of the FcγRIII. "Naturally occuffing CD16" has the amino acid sequence of cell surface receptor protein obtained from nature and includes naturally occurring variant forms including allelic variants, isotypes and truncated forms. Human CD16 includes all isotypes of the a chain including both CD16 or FcγRIII-A (GenBank Accession no. Z46222) and CD16 or FcγRIII-B (GenBank Accession no. Z46223). Representative amino acid and nucleotide sequences of the alpha chain of FcγRIII are shown in FIG. 22A/B/C/D/E. Representative sequences for the human gamma chain are shown in FIG. 25 (GenBank Accession No. P30273 and M33195). The invention also contemplates CD16 or FcγRIII variants. The variants are changed as compared to a source sequence by generally known techniques and preferably retain the biological activity of a naturally occurring human CD16 or FcγRIII. Some variants of FcγRIII are known to those of skill in the art.

The term "CD20" refers to a cell surface protein that is expressed on certain cells of the immune system, specifically the B lymphocyte-restricted differentiation antigen Bp35. "Naturally occurring CD20" has an amino acid sequence of a protein obtained from nature and includes naturally occurring variants such as allelic variants, isotypes and truncated forms. More specifically, "CD20" includes human CD20 (AH003353; GenBank Accession nos. M27395, J03574). Representative amino acid sequence, cDNA sequence and a genomic sequence of human and murine CD20 are shown in FIG. 23. The invention also contemplates CD20 variants. The variants are changed as compared to a source sequence using generally known techniques and preferably retain the biological activity of a naturally occurring human CD20. Preferably the variants are not changed at amino acid positions 170 and 172 of a naturally occurring human CD20 as these positions have been shown to be a part of the epitope recognized by several different anti-human CD20 monoclonal antibodies as described in Polyak et al., Blood 99:3256 (2002).

"Disruption" of a gene occurs when a fragment of DNA locates and recombines with an endogenous homologous sequence. These sequence disruptions or modifications may include insertions, missense, frameshift, deletion, or substitutions, or replacements of DNA sequence, or any combination thereof. Insertions include the insertion of entire genes, which may be of animal, plant, fungal, insect, prokaryotic, or viral origin. Disruption, for example, can alter the normal gene product by inhibiting its production partially or completely or by enhancing the normal gene product's activity. In a preferred embodiment, the disruption is a null disruption that has no significant expression of the gene.

By the term "endogenous loci" is meant to include the naturally occurring genetic loci found in the host animal that is to become transgenic.

The term "heterologous" when used in conjunction with polypeptide or gene refers to a polypeptide having an amino acid sequence or a DNA encoding the polypeptide that is not found in transgenic nonhuman host animal. Thus, a transgenic mouse having a human CD20 gene can be described as having a heterologous CD20 gene. The transgene can be detected using a variety of methods including PCR, Western blot, or Southern blot. The term "human endogenous promoter" refers to the promoter that is naturally associated with the polynucleotide sequence that encodes the human protein that is to be introduced into the animal to form a transgenic animal.

The term "non-human animals" is intended to include any vertebrate such as mammals, birds, reptiles, and amphibians. Suitable mammals include rodents, non-human primates, sheep, dogs and cows. Suitable birds include chickens, geese, and turkeys. Preferred non-human animals are selected from the rodent family including rat and mouse, most preferably mouse.

The term "naturally-occurring" or "naturally associated" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

For nucleic acids, the term "substantial homology" indicates that two nucleic acids, or designated sequences thereof, when optimally aligned and compared with appropriate nucleotide insertions or deletions have at least about 80% sequence identity, more preferably about 81% sequence identity, more preferably about 82% sequence identity, more preferably about 83% sequence identity, more preferably about 84% sequence identity, more preferably about 85% sequence identity, more preferably about 86% sequence identity, more preferably about 87% sequence identity, more preferably about 88% sequence identity, more preferably about 89% sequence identity, more preferably about 90% sequence identity, more preferably about 91% sequence identity, more preferably about 92% sequence identity, more preferably about 93% sequence identity, more preferably about 94% sequence identity, more preferably about 95% sequence identity, more preferably about 96% sequence identity, more preferably about 97% sequence identity, more preferably about 98% sequence identity, and more preferably about 99% sequence identity to one another. Alternatively, substantial homology exists when the segments will hybridize under selective hybridization conditions, to the complement of the strand. Methods of aligning two sequences and identifying % identity are known to those of skill in the art. Several computer programs are available for determining % identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

"Transcriptional regulatory sequence" refers to polynucleotide sequences, such as initiation signals, enhancers, and promoters, which induce or control transcription of protein coding sequences with which they are operably linked. In preferred embodiments, transcription of a recombinant transgene is under the control of a promoter sequence (or other transcriptional regulatory sequence), which controls the expression of the recombinant gene in a cell-type in which expression is intended. It will also be understood that the recombinant gene can be under the control of transcriptional regulatory sequences which are the same or which are different from those sequences, which control transcription of a naturally-occurring form of CD20 or CD16.

As used herein, the term "transgene" means a nucleic acid sequence (encoding, e.g., CD20 or CD16) that has been introduced into a cell by way of human intervention such as by way of the described methods herein. A transgene could be partly or entirely heterologous, i.e., foreign, to the transgenic animal or cell into which it is introduced. A transgene can include one or more transcriptional regulatory sequences and any other nucleic acid, such as introns, that may be necessary for optimal expression of a selected nucleic acid.

"Transgenic animal" or "Tg+" are used interchangeably and are intended to include any non-naturally occurring non-human animal in which one or more of the cells of the animal contain heterologous nucleic acid encoding human CD20 and/or preferably, human CD16, that has been introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, but rather is directed to the introduction of a recombinant DNA molecule. This molecule may be integrated within a chromosome, or it may be extrachromosomally replicating DNA. The term "Tg+" includes animals that are heterozygous and/or homozygous for either human CD20 and/or human CD16.

"CD20 associated disease" refers to diseases or disorders that have been associated with the expression of CD20 on cells, aberrant proliferation or activation of B cells, or have been treated with anti-CD20 antibodies. For example, a chimeric anti-CD20 antibody has been used to treat patients with lymphoma. Other diseases or conditions that have been treated with anti-CD20 therapy include autoimmune conditions or diseases such as rheumatoid arthritis, systemic lupus erythromatosis, and ankylosing spondylitis. Other conditions include Epstein Barr virus associated disease following blood or bone marrow transplant, Karposi Sarcoma associated herpes virus related multicentric Castlemen disease, Hepatitis C associated Cryoglobulinemia Vasculitis, lymphoproliferative disorders with autoimmune hemolytic anemia, and ANCA associated vasculitis.

A. Modes of the Invention

The present invention provides transgenic animals expressing a heterologous CD20 marker, a heterologous CD16 marker or both. In one embodiment, the human CD20 transgenic animals of the invention express CD20 on the same types of B cells. Administration of anti-human CD20 antibodies to the presently described transgenic animals results in depletion of B lymphocytes expressing human CD20. Previous attempts to prepare transgenic mice expressing human CD20 may not have achieved expression of human CD20 in the appropriate B cell compartments due to lack of incorporation of effective transcriptional control regions into the transgene. In another embodiment, transgenic mice of the invention express human CD20 and human CD16.

The present invention provides a transgenic animal that has cells that react in a way that is similar to a human subject. Administration of anti-human CD20 antibodies to the presently described transgenic animals results in depletion of B lymphocytes expressing human CD20. In one embodiment, the human CD20 trangenic mice are characterized by expression of human CD20 on cells at a level sufficient for anti-human CD20 antibody bound to the expressing cells to affect killing of the cells, resulting in B cell depletion of peripheral and/or circulating B cells of at least about 75% and more preferably, 80%, 85%, 90%, 95%, 99% and even 100%. A similar response is observed in humans. These animal models can be used for screening of agents including but not limited to monoclonal antibodies against the CD20 marker. In addition, transgenic mice expressing human CD16 provide models for determining an agent's ability to induce an effector cell response (such as, for example, an NK cell mediated response) or the agent's ability to further deplete B lymphocytes expressing CD20 (including malignant B cells). Additionally, the transgenic animals may be used to test the efficacy and toxicity of anti-CD20 directed therapies.

B. DNA Constructs

Typically, a polynucleotide molecule encoding a heterologous protein of the invention is inserted into a vector, preferably a DNA vector, in order to replicate the polynucleotide molecule in a suitable host cell. It will be understood that the CD20 and/or CD16 transgenes may be generated and inserted separately, or generated together in a single construct for insertion. DNA constructs may also be useful to prepare targeting vectors for knockout animals.

In order to isolate, clone and transfer the CD16 and/or CD20 locus, a yeast artificial chromosome (YAC) may be employed. The entire locus can be cloned and contained within one or a few YAC clones. If multiple YAC clones are employed and contain regions of overlapping homology, they can be recombined within yeast host strains to produce a single construct representing the entire locus. YAC arms can be additionally modified with mammalian selection cassettes by retrofitting to assist in the introduction of the constructs into embryonic stems cells or embryos by the previously outlined methods.

Due to the high stability and relatively large inserts, ease of manipulation and shotgun sequencing, bacterial artificial chromosome (BAC) libraries can provide human sequences for genes of interest. BAC libraries contain an average insert size of 100-150 kb. BAC clones are capable of harboring inserts as large as 300,000 base pairs. Shizuya, et al., (1992) Proc. Natl. Acad. Sci., USA 89:8794-8797; Kim, et al., (1996) Genomics 34 213-218; Swiatek, et al., (1993) Genes and Development 7:2071-2084. Genomic BAC libraries of the human and mouse have been constructed and are commercially available (Invitrogen, Carlsbad Calif.). Genomic BAC libraries can also serve as a source of human and murine CD20 and/or CD16 gene sequences as well as transcriptional control regions.

Nucleic acids encoding human CD20 are known to those of skill in the art. Representative cDNA (SEQ ID NO: 5), genomic (SEQ ID NO: 6) and amino acid sequences (SEQ ID NO: 4) of human and murine CD20 are shown in FIG. 23. Other sequences can also be found in GenBank, such as Accession No. AH003353.

Nucleic acids encoding the isotypes of the a chain of human CD16 are known to those of skill in the art. Representative cDNA (SEQ ID NO: 2), genomic (SEQ ID NO: 3) and amino acid sequences (SEQ ID NO: 1) of human α chain subtype A are shown in FIGS. 22A, B and C (GenBank Accession Nos. NM000569 and Z46222). Representative amino acid (SEQ ID NO: 10) and cDNA sequences (SEQ ID NO: 11) for human CD16 α chain isotype B are shown in FIG. 22E. (GenBank Accession No. NM000570). A genomic sequence encoding human CD16 α chain isotype B is shown in FIG. 22F (GenBank Accession NO. Z46223). A nucleic acid sequence encoding a human Fc receptor gamma chain is also known to those of skill in the art. Representative amino acid (SEQ ID NO: 7) (GenBank Accession No. P30273) and cDNA sequences (GenBank Accession No. M33 195) (SEQ ID NO: 8) are shown in FIG. 25.

The heterologous transgenes preferably comprise germ-line regulatory DNA sequences operably linked to the gene of interest that is to be expressed in a transgenic non-human animal. By the term "operably linked" is meant a genetic sequence operationally (i.e., functionally) linked to a nucleic acid segment, or sequences upstream (5') or downstream (3') from a given segment or sequence. Those nearby sequences often impact processing and/or expression of the nucleic acid segment or sequence in a desired cell type.

Preferably, these regulatory sequences are genomic in origin, and include one or more introns. For example, the transgenic construct can include regulatory regions located in the 5'-flanking regions of a gene encoding CD20 and/or CD16, operably linked to the coding sequences in a manner capable of replicating and expressing the gene in a host cell. In one embodiment, the regulatory sequences comprise the endogenous promoter sequence naturally associated with either the CD20 and/or CD16. In some embodiments, the promoters provide for tissue specific expression at a level similar to that level of expression in the animal from which the sequence is derived. If additional flanking sequences are useful in optimizing expression, such sequences can be cloned using the existing sequences as probes. Additional sequences necessary for maximizing processing or expression of the transgene can be derived from genomic sequences.

Alternatively, the promoters can be those promoters associated with the corresponding endogenous gene in the transgenic host animal. For example, if the murine genes CD20 and/or CD16 genes are disrupted by integration with the corresponding human genes, the corresponding human genes are preferably integrated so as to be operably linked to murine transcriptional control regions for the endogenous murine CD20 and/or CD16 respectively.

Preferably, the regulatory sequences provide for expression of the transgene in the appropriate cells and at a level so that expression can be detected using standard methodologies such as detection with antibodies. In one embodiment, the regulatory sequences provide for expression of the human CD20 transgene at a level at least 40% of the expression of CD20 on human cells.

An expression system or construct encoding a transgene can be expressed from a construct that includes transcriptional regulatory sequences specific for the CD20 marker and/or CD16 receptor, e.g., a human endogenous promoter (see, for example, U.S. Pat. No. 5,877,396, incorporated herein by reference).

An expression system or construct encoding a transgene as described herein can also include a 3' untranslated region downstream of the DNA sequence. Such regions can stabilize the RNA transcript of the expression system and thus increases the yield of desired protein from the expression system. Among the 3' untranslated regions useful in the constructs of this invention are sequences that provide a poly A signal. Such sequences may be derived, e.g., from the SV40 small t antigen, the CD20 and/or CD16 untranslated region or other 3' untranslated sequences well known in the art.

Optionally, the expression system or construct includes a 5' untranslated region between the promoter and the DNA sequence encoding the signal sequence. Such untranslated regions can be from the same control region from which promoter is taken or can be from a different gene, e.g., they may be derived from other synthetic, semi-synthetic or natural sources.

In addition, other promoters or other transcriptional regulatory sequences not naturally associated with the transgene may be utilized. For example, heterologous promoters may provide for enhanced levels of expression or tissue specific expression. Various promoters having different strengths may be utilized as long the promoter functions in the non-human animal or in the desired tissue type. Many promoters are known to those of skill in the art.

Expression systems can be prepared using methods known in the art. For example, an expression system can be prepared as part of a larger plasmid. Such preparation allows the cloning and selection of the correct constructions in an efficient manner as is known in the art. Expression systems can be located between convenient restriction sites on the plasmid so that they can be easily isolated from the remaining plasmid sequences for incorporation into the desired mammal. Preferably, the DNA construct encoding the human CD20 and/or CD16 comprises a bacterial artificial chromosome including the naturally associated transcriptional regulatory sequences to provide for tissue specific expression.

The various methods employed in the preparation of the plasmids and transformation of host organisms are known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

C. Production of Transgenic Animals

Methods for generating transgenic animals of the present invention, including knock-outs and knock-ins, are well known in the art (see, generally, Gene Targeting: A Practical Approach, Joyner, ed., Oxford University Press, Inc. (2000)). Generation of the transgenic mice may optionally involve disruption of the genetic loci of the murine marker and introduction of the gene encoding the human marker into the murine genome, preferably at the same location as the endogenous gene.

According to the invention, a transgenic mouse model is generated where the human CD20 has been introduced into the murine genome (huCD20$^+$; alternatively referenced as huCD20Tg$^+$). An endogenous murine CD20 polypeptide is present on murine lymphocytes, but the known anti-human CD20 monoclonal antibodies do not bind to murine B cells. The endogenous murine CD20 gene, therefore, does not have to be but can be disrupted, if desired. When the endogenous murine CD20 is not disrupted then the gene encoding human CD20 is preferably inserted at a location other than that of the gene encoding murine CD20.

In a preferred embodiment, the genome of the transgenic animal further comprises a sequence encoding human CD16, preferably, the a chain, and more preferably the subtype A alpha chain. When mice are used, knock-out lines are preferably generated wherein the murine CD16 gene, preferably the a chain, has been disrupted (mCD16$^{-/-}$). Separately, a transgenic murine line is generated where the human CD16 alpha chain gene has been introduced into the genome (huCD16$^+$; alternatively referenced as huCD16Tg$^+$). The mCD16$^{-/-}$ and huCD16$^+$ mouse lines are then cross bred to generate a mouse line expressing human CD16 alpha chain but not expressing endogenous CD16 (huCD16$^+$mCD16$^{-/-}$). Alternatively, the human gene can be introduced into an ES cell derived from the mCD16$^{-/-}$ line or can be used to disrupt the murine CD16 gene.

Inactivation of Endogenous Loci

In a preferred embodiment, inactivation of the endogenous loci is achieved by targeted disruption through homologous recombination in embryonic stem cells. In one embodiment, DNA is introduced into a host cell and recombines at the endogenous loci to disrupt the production of endogenous CD16. Similarly, in another embodiment, DNA is introduced into a host cell and recombines at endogenous CD20 loci to disrupt production of endogenous CD20.

The targeting construct may be produced using standard methods known in the art (see, e.g., Sambrook et al., 1989, Molecular Cloning: A Laboratory Manual, Second Edition, Cold Spring Harbor Laboratory Press, Cold Spring Harbor, N.Y.; E. N. Glover (eds.), 1985, DNA Cloning: A Practical Approach, Volumes I and II; M. J. Gait (ed.), 1984, Oligonucleotide Synthesis; B. D. Hames & S. J. Higgins (eds.), 1985, Nucleic Acid Hybridization; B. D. Hames & S. J. Higgins (eds.), 1984, Transcription and Translation; R. I. Freshney (ed.), 1986, Animal Cell Culture; Immobilized Cells and Enzymes, IRL Press, 1986; B. Perbal, 1984, A Practical Guide To Molecular Cloning; F. M. Ausubel et al., 1994, Current Protocols in Molecular Biology, John Wiley & Sons, Inc.). For example, the targeting construct may be prepared in accordance with conventional ways, where sequences may be synthesized, isolated from natural sources, manipulated, cloned, ligated, subjected to in vitro mutagenesis, primer repair, or the like. At various stages, the joined sequences may be cloned, and analyzed by restriction analysis, sequencing, or the like.

The targeting DNA can be obtained using techniques well known in the art. For example, the targeting DNA may be produced by chemical synthesis of oligonucleotides, nick-translation of a double-stranded DNA template, polymerase chain-reaction amplification of a sequence (or ligase chain reaction amplification), purification of prokaryotic or target cloning vectors harboring a sequence of interest (e.g., a cloned cDNA or genomic DNA, synthetic DNA or from any of the aforementioned combination) such as plasmids, phagemids, YACs, cosmids, BACs, bacteriophage DNA, other viral DNA or replication intermediates, or purified restriction fragments thereof, as well as other sources of single and double-stranded polynucleotides having a desired nucleotide sequence. Moreover, the length of homology may be selected using known methods in the art. For example, selection may be based on the sequence composition and complexity of the predetermined endogenous target DNA sequence(s).

In one embodiment, the targeting construct of the present invention comprises a targeting region, which comprises a first sequence (or arm) homologous to a portion or region of the CD16 gene and/or CD20 to be disrupted and a second sequence homologous to a second portion or region of the gene. The targeting construct may further comprise a positive selection marker, which is preferably positioned between the first and the second DNA sequences. The positive selection marker may be operatively linked to a promoter and a polyadenylation signal.

In another embodiment, the targeting construct may contain more than one selectable maker gene, including a negative selectable marker, such as the herpes simplex virus tk (HSV-tk) gene, which is preferably positioned outside one or both of the homologous arms of the targeting construct. The negative selectable marker may be operatively linked to a promoter and a polyadenylation signal (see, e.g., U.S. Pat. Nos. 5,464,764; 5,487,992; 5,627,059 and 5,631,153).

Once an appropriate targeting construct has been prepared, the targeting construct may be introduced into an appropriate host cell using any method known in the art. Various techniques may be employed in the present invention, including, for example: pronuclear microinjection; retrovirus mediated gene transfer into germ lines; gene targeting in embryonic stem cells; electroporation of embryos; sperm-mediated gene transfer; and calcium phosphate/DNA co-precipitates, microinjection of DNA into the nucleus, bacterial protoplast fusion with intact cells, transfection, polycations, e.g., polybrene, polyornithine, etc., or the like (see, e.g., U.S. Pat. No. 4,873, 191; Van der Putten et al., 1985, Proc. Natl. Acad. Sci., USA 82:6148-6152; Thompson et al., 1989, Cell 56:313-321; Lo, 1983, Mol Cell. Biol. 3:1803-1814; Lavitrano et al., 1989, Cell, 57:717-723). Various techniques for transforming mammalian cells are known in the art. (see, e.g., Gordon, 1989, Intl. Rev. Cytol., 115:171-229; Keown et al., 1989, Methods in Enzymology; Keown et al., 1990, Methods and Enzymology, Vol. 185, pp. 527-537; Mansour et al., 1988, Nature, 336:348-352).

Any cell type capable of homologous recombination may be used in the practice of the present invention. Examples of such target cells include cells derived from vertebrates including mammals such as humans, bovine species, ovine species, murine species, simian species, and ether eukaryotic organisms such as filamentous fungi, and higher multicellular organisms such as plants.

Preferred cell types include embryonic stem (ES) cells, which are typically obtained from pre-implantation embryos cultured in vitro (see, e.g., Evans, M. J. et al., 1981, Nature 292:154-156; Bradley, M. O. et al., 1984, Nature 309:255-258; Gossler et al., 1986, Proc. Natl. Acad. Sci. USA 83:9065-9069; and Robertson et al., 1986, Nature 322:445-448). The ES cells are cultured and prepared for introduction of the targeting construct using methods well known to the skilled artisan. (see, e.g., Robertson, E. J. ed. "Teratocarcinomas and Embryonic Stem Cells, a Practical Approach", IRL Press, Washington D.C., 1987; Bradley et al., 1986, Current Topics in Devel. Biol. 20:357-371; by Hogan et al., in "Manipulating the Mouse Embryo": A Laboratory Manual, Cold Spring Harbor Laboratory Press, Cold Spring Harbor N.Y., 1986; Thomas et al., 1987, Cell 51:503; Koller et al., 1991, Proc. Natl. Acad. Sci. USA, 88:10730; Dorin et al., 1992, Transgenic Res. 1:101; and Veis et al., 1993, Cell 75:229). The ES cells that will be inserted with the targeting construct are derived from an embryo or blastocyst of the same species as the developing embryo into which they are to be introduced. ES cells are typically selected for their ability to integrate into the inner cell mass and contribute to the germ line of an individual when introduced into the mammal in an embryo at the blastocyst stage of development. Thus, any ES cell line having this capability is suitable for use in the practice of the present invention.

After the targeting construct has been introduced into cells, the cells in which successful gene targeting has occurred are identified. Insertion of the targeting construct into the targeted gene is typically detected by identifying cells for expression of the marker gene. In a preferred embodiment, the cells transformed with the targeting construct of the present invention are subjected to treatment with an appropriate agent that selects against cells not expressing the selectable marker. Only those cells expressing the selectable marker gene survive and/or grow under certain conditions. For example, cells that express the introduced neomycin resistance gene are resistant to the compound G418, while cells that do not express the neo gene marker are killed by G418. If the targeting construct also comprises a screening marker such as GFP, homologous recombination can be identified through screening cell colonies under a fluorescent light. Cells that have undergone homologous recombination will have deleted the GFP gene and will not fluoresce.

Alternatively, a positive-negative selection technique may be used to select homologous recombinants. This technique involves a process in which a first drug is added to the cell population, for example, a neomycin-like drug to select for growth of transfected cells, i.e. positive selection. A second drug, such as FIAU, is subsequently added to kill cells that express the negative selection marker, i.e. negative selection. Cells that contain and express the negative selection marker are killed by a selecting agent, whereas cells that do not contain and express the negative selection marker survive. For example, cells with non-homologous insertion of the construct express HSV thymidine kinase and therefore are sensitive to the herpes drugs such as gancyclovir (GANC) or FIAU (1-(2-deoxy 2-fluoro-B-D-arabinofluranosyl)-5-iodouracil). (see, e.g., Mansour et al., Nature 336:348-352: (1988); Capecchi, Science 244:1288-1292, (1989); Capecchi, Trends in Genet. 5:70-76 (1989)). Other methods include regulated positive selection (see U.S. 20030032175A1), which requires the addition of a single selective agent.

Successful recombination may be identified by analyzing the DNA of the selected cells to confirm homologous recombination. Various techniques known in the art, such as PCR and/or Southern analysis may be used to confirm homologous recombination events.

Selected cells are then injected into a blastocyst (or other stage of development suitable for the purposes of creating a viable animal, such as, for example, a morula) of an animal (e.g., a mouse) to form chimeras (see e.g., Bradley, A. in Teratocarcinomas and Embryonic Stem Cells: A Practical Approach, E. J. Robertson, ed., IRL, Oxford, pp. 113-152 (1987)). Alternatively, selected ES cells can be allowed to aggregate with dissociated mouse embryo cells to form the aggregation chimera. A chimeric embryo can then be implanted into a suitable pseudopregnant female foster animal and the embryo brought to term. Chimeric progeny harboring the homologously recombined DNA in their germ cells can be used to breed animals in which all cells of the animal contain the homologously recombined DNA. In one embodiment, chimeric progeny mice are used to generate a mouse with a heterozygous disruption in the CD16 or CD20 gene. Heterozygous transgenic mice can then be mated. It is well known in the art that typically ¼ of the offspring of such matings will have a homozygous disruption in the CD16 or CD20 gene.

In addition to the above described methods of inactivation of endogenous loci, additional preferred methods of inactivation are available and may include for example, use of the tet transcription system to utilize temporal control of specific genes of interest (Proc. Natl. Acad. Sci. 91:9302-9306 (1994)) or introduction of deoxycycline transcriptional regulatory controls for tissue specific control (Proc. Natl. Acad. Sci. 93:10933-10938 (1996)).

An additionally preferred method for functional inactivation includes employment of the cre-lox deletion, site specific recombination system for targeted knock-out of genetic loci, wherein loxP sites are inserted to flank genes of interest and cre recombinase activated to delete genes (Curr. Opin. Biotechnol., 5:521-527 (1994)).

Alternatively, antisense or RNAi methods may be utilized in order to inhibit transcription of the desired loci, thus resulting in functional disruption of endogenous loci (knock-down methods). In such a situation, oligonucleotides are generated which target specific sequences of the designated locus of interest, wherein successful targeting results in inhibited production of the functional protein.

Strains of knockout mice lacking murine FcγRIII receptor are commercially available from Taconic. These mice lack the murine FcγRIII gamma chain, which also results in loss of expression of FcγRI and FcγRIII. In addition, knockout mice lacking a functional murine γ chain and, therefore, lacking a murine FcγRIII receptor can be prepared as described in U.S. Pat. No. 5,877,396 which is hereby incorporated by reference.

Mice lacking a functional murine FcγRIII α chain can be generated using similar methods. Briefly, in one embodiment, a targeting vector can be prepared using a cDNA sequence for murine CD16 α chain as shown in FIG. 22G (GenBank Accession No. NM010188). The targeting vector preferably includes 5' sequences upstream from the coding sequence as well as at least 300 nucleotides of the coding sequence. This construct can be cloned into a vector encoding the neomycin resistance gene such as pMC1 neo (Stratagene). The resulting vector can then be introduced into ES cells using electroporation. The ES cells are plated on neo resistant embryonic fibroblast feeder layers and then selected in the presence of G418. Selected ES cells are injected into blastocysts. Appropriate targeting of murine CD16 α chain can be determined using RT-PCR or by loss of expression of murine CD16 alpha chain on cells. PCR primers can be designed using the cDNA sequence for murine CD16 α chain.

Knock-out mice homozygous for the loss of endogenous CD20 can be prepared as described in WO 02/062946. Briefly, in one embodiment, CD20-deficient mice can be generated by targeted disruption of the murine CD20 gene in embryonic stem (ES) cells using homologous recombination. A targeting vector can be generated that replaces exons encoding part of the second extracellular loop, the $4^{th}$ transmembrane domain, and the large carboxyl-terminal cytoplasmic domain of murine CD20 with a neomycin resistance gene. The nucleotide sequence of murine CD20 is known to those of skill in the art. (GenBank Accession No. M62541). In one embodiment, appropriate gene targeting generates an aberrant CD20 protein truncated at amino acid position 157 and fused with an 88 amino acid protein encoded by the Neo gene sequence.

After DNA transfection, neo-resistant ES cell clones carrying the targeted allele can be determined by Southern blot analysis. Cells of one ES cell clone can be injected into blastocysts that can be transferred into foster mothers. Highly chimeric male offspring (80-100% according to coat color) can be bred with C57BL/6 (B6) females for transmitting the mutation to their progeny. Mice homozygous for disruption of the CD20 gene can be obtained at the expected Menedelian frequency by crossing heterozygous offspring.

Appropriate targeting of the CD20 can be further verified by PCR analysis of genomic DNA from homozygous offspring. Presence or absence of wild type CD20 mRNA in $CD20^{-/-}$ mice can be confirmed by PCR amplification of cDNA generated from splenocytes of $CD20^{-/-}$ mice. Absence of cell surface CD20 protein expression in $CD20^{-/-}$ mice can be further verified by staining $B220^+$ splenocytes with murine anti-CD20 monoclonal antibodies. Targeted mutation of the CD20 gene abrogates cell surface CD20 protein expression.

Introducing Transgenes into Non-Human Animal

The transgenic non-human animals of the invention are preferably produced by introducing transgenes into the germline of the animal. Embryonic target cells at various developmental stages can be used to introduce transgenes. Different methods are used depending on the stage of development of the embryonic target cell. The specific line(s) of any animal used to practice this invention are selected for general good health, good embryo yields, good pronuclear visibility in the embryo, and good reproductive fitness. When transgenic mice are to be produced, strains such as C57BL/6 or C57BL/6×DBA/2 $F_1$, or FVB lines are often used (obtained commercially from Charles River Labs, Boston, Mass., The Jackson Laboratory, Bar Harbor, Me., or Taconic Labs.). Preferred strains are those with $H-2^b$, $H-2^d$ or $H-2^q$ haplotypes such as C57BL/6 or DBA/1. Nude mice may be utilized in order to allow for the introduction of human tumor cells. Breeding and maintenance of nude mice are more difficult because of their susceptibility to infection and disease. The line(s) used to practice this invention may themselves be transgenics, and/or may be knockouts. Preferably the same line will be used for preparation of both the initial knockout mammals and the transgenic mammals. This will make subsequent breeding and backcrossing more efficient.

Introduction of the transgene into the embryo can be accomplished by any means known in the art such as, for example, microinjection, electroporation, or lipofection. For example, the transgene can be introduced into a mammal by microinjection of the construct into the pronuclei of the fertilized mammalian egg(s) to cause one or more copies of the construct to be retained in the cells of the developing mammal (s). Following introduction of the transgene construct into the fertilized egg, the egg may be incubated in vitro for varying amounts of time, or reimplanted into the surrogate host, or both. In vitro incubation to maturity is within the scope of this invention. One common method is to incubate the embryos in vitro for about 1-7 days, depending on the species, and then reimplant them into the surrogate host.

Reimplantation is accomplished using standard methods. Usually, the surrogate host is anesthetized, and the embryos are inserted into the oviduct. The number of embryos implanted into a particular host will vary by species, but will usually be comparable to the number of offspring the species naturally produces.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van der Putten, supra; Stewart et al. (1987) EMBO J. 6:383-388). Alternatively, infection can be performed at a later stage. Virus or virus-producing cells can be injected into the blastocoele (Jahner et al. (1982) Nature 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonic stem cell. Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal.

In one embodiment, a cDNA or genomic clone encoding human CD20 such as shown in FIG. 23 can be introduced into FVB mice fertilized eggs or ES cells using microinjection or transfection. The embryos are incubated in vitro from about 1-7 days and then implanted into a surrogate host. The ES cells are combined with blastocysts from naturally mated host animals and the blastocysts are reimplanted into surrogate mothers.

In another embodiment, a cDNA or genomic clone encoding human CD 16 α chain subtype A such as shown in FIG. 22, can be introduced into ES cells or fertilized embryos used transfection or microinjection. In alternative embodiment, a cDNA or genomic clone encoding human Fc receptor gamma chain can be also introduced along with human CD16 alpha chain into ES or fertilized embryos. The fertilized eggs are incubated in vitro for 1-7 days and then reimplanted in a surrogate host. The ES cells are combined with blastocysts from naturally mated host animals and the blastocysts are reimplanted into surrogate mothers. Expression of human CD16 alpha chain (FcγRIII α chain) in mouse cells will occur in the presence of mouse gamma chain as the mouse and human gamma chains are similar in sequence.

In one embodiment of the invention, an endogenous CD20 or CD16 gene in a nonhuman host is functionally disrupted by homologous integration of a heterologous CD20 or CD16 alpha chain gene, such that the heterologous CD20 or CD16 gene substantially replaces the endogenous CD20 or CD16 gene, respectively, and preferably completely replaces the coding sequences of the endogenous CD20 or CD16 gene. Preferably, the heterologous CD20 or CD16 gene is linked, as a consequence of homologous integration, to regulatory sequences (e.g., an enhancer promoter) of the endogenous CD20 or CD16 gene, respectively, so that the heterologous gene is expressed under the transcriptional control of regulatory elements from the endogenous CD20 or CD16 gene locus. Nonhuman hosts which are homozygous for such replacement alleles may be produced according to methods described herein. Such homozygous nonhuman hosts generally will express a heterologous CD20 or CD16, or both, but do not express the endogenous CD20 or CD16 protein. Usually, the expression pattern of the heterologous CD20 or CD16 gene will substantially mimic the expression pattern of the endogenous CD20 or CD16 gene, respectively, in the naturally-occurring (non-transgenic) nonhuman host.

For example, a transgenic mouse can be generated that has human CD20 gene sequences in place of endogenous murine CD20 gene sequences and which are transcriptionally controlled by endogenous murine regulatory sequences. The human CD20 generally will be expressed similarly to the murine CD20 in naturally occurring non-transgenic mice.

For example, a transgenic mouse can be generated that has the human CD16 α chain sequences and which are transcriptionally controlled by endogenous murine regulatory sequences. Alternatively, the human CD16 α chain can be introduced into a mouse and can then be crossed with a mouse lacking expression of a murine CD16 α chain. Expression of human CD16 α chain is expected to occur in the presence of the murine gamma chain.

Generally, a replacement-type targeting construct is employed for homologous gene replacement. Double-crossover homologous recombination between endogenous CD20 or CD16 alpha gene sequences of the targeting construct result in targeted integration of the heterologous CD20 or CD16 gene segments. Usually, the homology targeting regions of the transgene comprise sequences which flank the endogenous CD20 and/or CD16 alpha gene segments, so that homologous recombination results in concomitant deletion of the endogenous CD20 and/or CD16 gene segments, respectively, and homologous integration of the heterologous gene segments. Substantially an entire endogenous CD20 and/or CD16 gene may be replaced with a heterologous CD20 and/or CD16 gene by a single targeting event or by multiple targeting events (e.g., sequential replacement of individual exons). One or more selectable markers, usually in the form of positive or negative selection expression cassettes, may be positioned in the targeting construct. It is usually preferred that selectable markers are located in intron regions of the heterologous replacement region.

Crossing of Transgenic Mice

Transgenic mice comprising transgene human CD20 can be crossed with transgenic mice comprising transgene human CD16 and lacking the murine CD16. Preferably, the transgenic mouse comprises the human CD16 α chain and lacks the murine CD16 α chain. A manner of preparation is to generate a series of mammals, each containing one of the desired knockout constructs or transgenes. Such mammals are bred together through a series of crosses, backcrosses and selections, to ultimately generate a single mammal containing all desired knockout constructs and/or transgenes, where the mammal is otherwise congenic (genetically identical) to the wild type except for the presence of the knockout(s) constructs and/or transgene(s).

Typically, crossing and backcrossing is accomplished by mating siblings or a parental strain with an offspring, depending on the goal of each particular step in the breeding process. In certain cases, it may be necessary to generate a large number of offspring in order to generate a single offspring that contains each of the knockout constructs and/or transgenes in the proper chromosomal location. In addition, it may be necessary to cross or backcross over several generations to ultimately obtain the desired genotype.

Once the human loci have been introduced into the host genome, either by homologous recombination or random integration, and host animals have been produced with the endogenous CD16 loci inactivated by appropriate breeding of the various transgenic or mutated animals, one can produce a host which lacks the native capability to produce endogenous CD16 α chain, but has the capacity to produce human CD16 α chain and/or CD20.

In one embodiment, transgenic mice expressing human CD16 α chain are mated to murine CD16 α chain deficient mice, thereby reconstituting expression of a specific human CD16 thereof in a mouse deficient for that CD16 polypeptide. In another embodiment, these transgenic mice can then be bred with mice expressing human CD20 to create a line of mice expressing both human CD16 and human CD20 but not endogenous CD16.

D. Verification of the Presence of Transgenes

Transgenic offspring of the surrogate host may be screened for the presence and/or expression of the transgene in the desired tissue, cell or animal by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents. In one embodiment, expression of human CD20 or CD16 or both can be detected on immune cells from spleen, bone marrow, peripheral blood, lymph nodes, and Peyer's Patches using a detectably labeled antibody to human CD20 or CD16 or both and analyzing the labeled cells using FACS.

Examination of expression patterns in the transgenic mice of the present invention reveals a mirroring of normal human CD20 expression found in human B lineage cells. Other immunological parameters examined in terms of percentage of cells and phenotypic characteristics, including those of T cells, B cells, NK cells, macrophages, dendritic cells and neutrophils, revealed a similarity between transgenic negative and positive littermates. Examination of the expression patterns in CD20Tg+/CD16Tg+ shows expression of both human CD20 and CD16 markers.

E. Uses of Transgenic Animals

Transgenic animals of the present invention represent models of CD16 and/or CD20 expression and function in humans. Accordingly, these animals are useful in studying the mechanisms behind their function and related events, and to generate and test products (e.g., antibodies, bispecifics, multispecifics etc.) useful in treating and diagnosing CD20 associated human diseases, including cancer and autoimmune conditions.

In preferred embodiments, transgenically expressed human CD20 and/or CD16 retain similar functional properties as are exhibited in human cells. For example, B lymphocytes expressing human CD20 are recognized by anti-human CD20 antibodies and as in the human, are similarly depleted from the transgenic animal in response to administration of human CD20 antibody. As described in further detail in the Examples, B lymphocytes in the transgenic mice of the present invention are depleted in response to treatment with anti-human CD20 antibodies such as Rituxan. In one embodiment, the human CD20 trangenic mice are characterized by expression of human CD20 on cells at a level sufficient for anti-human CD20 antibody bound to the expressing cells to affect killing of the cells, resulting in B cell depletion of peripheral and/or circulating B cells of at least about 75% and more preferably, 80%, 85%, 90%, 95%, 99% and even 100%.

In addition, human CD20 is found on the same type of B cells as that of human CD20. Cells expressing human CD16 are also recognized by anti-human CD16 antibodies.

The transgenic CD16 animal is preferably capable of mediating at least one Fc-receptor mediated effector cell function or response. The term "Fc-receptor mediated effector cell function" is intended to include any effector function, which is triggered by binding of immunoglobulin, e.g., IgG, to an Fc receptor on an effector cell. For example, binding of an immunoglobulin, e.g., IgG, to cells bearing transgenically expressed human CD16 can induce a variety of effector functions, such as antibody dependent cellular cytotoxicity (ADCC), NK cell mediated response and lysozyme production.

Accordingly, in one embodiment the transgenic animals of the invention are used to test agents such as antibodies, multior bispecific molecules, immunoadhesins (e.g., for human safety and efficacy) for binding to target epitopes, such as a region of a human CD20, human CD16 or both. Other agents can include antigen binding fragments of antibodies with or without Fc regions, single chain antibodies, minibodies (heavy chain only antibodies), heteromultimeric immunoadhesins with one of the multimers anti-human CD20 and/or anti-human CD16 antigen binding region. Other agents may include small molecules that inhibit or result in CD20-B cell depletion that may include variants of ligands of CD20 that bind to, but do not activate CD20. For example, the effectiveness of such agents to deplete CD20 expressing cells such as malignant B cells can be determined by measuring B lymphocyte levels in the transgenic animals before and after administration of the test agent.

Accordingly, the present invention provides methods of identifying agents capable of treating a B cell lymphoma, as well as agents capable of depleting or killing B lymphocytes expressing human CD20, by administering an agent to a transgenic animal that expresses human CD20 and determining whether there is a reduction in the number of B lymphocytes. As used herein, "B cell depletion" refers to a reduction in B cell levels in an animal or human after drug or antibody treatment as compared to the level before such treatment. B cell levels are measurable using well known assays as described herein. B cell depletion can be partial or complete. Preferably, the level of B cell depletion induced by the agent is an amount that correlates with a decrease or amelioration of the symptoms of the disease or disorder. The effectiveness of the putative agent (i.e., its ability to deplete B lymphocytes expressing CD20) can be assessed by measuring baseline levels of circulating B lymphocytes in a transgenic animal expressing CD20 and comparing with levels after administration in the same animal. A comparison of efficacy for B cell depletion can be made to known therapeutic agents such as anti-human CD20 antibodies (e.g. Rituxan) to gauge effectiveness of the putative agent for treatment for CD20 associated condition. Alternatively, baseline levels of B lymphocytes can be measured in the various tissues (e.g., spleen, bone marrow, peripheral blood, lymph nodes, Peyer's Patches) of a first transgenic animal expressing human CD20. The putative agent can then be administered to a second transgenic animal expressing human CD20. The animal is then sacrificed and the level of B lymphocytes analyzed. A reduction in the number of B lymphocytes in a transgenic animal expressing human CD20 is an indication of the agents' effectiveness in reducing cancerous cells associated with a B cell lymphoma, and/or treating a B cell lymphoma in a human subject. Combination therapies may also be tested to determine the effectiveness of depleting the desired cell types. For example, an anti-human CD20 antibody can be combined with another agent such as Br3-Fc to cause depletion of any CD20 bearing B cells that may be resistant to killing by anti-human CD20.

B lymphocyte recovery can also be assessed by measuring cell levels over time in a series of transgenic animals. The specificity of the agent for human CD20 can be assessed by comparing the agents' effect on transgenic mice expressing human CD20 with the effect on wild type mice (which do not express a CD20 marker). The effectiveness of the agent can also be compared with the effect of a placebo or control substance such as a non-specific Ab or other control agent. Preferably, the agent targets most or all cells bearing human CD20 and but does not affect cells providing immune responsiveness to antigens that stimulate a T independent immune response.

In addition, the animals are useful models for assessing the potential immune response in a human as the initiation of an immune response in the transgenic animal upon administration of such agents is indicative that the agents will produce the same effect in humans. An effect on the immune response in such a transgenic animal can be detected for example by a change in cytokine levels, production of an antibody or a T cell response. In addition, the transgenic animal can be engineered to contain target cells (e.g. tumor, virus) prior to administration of the multi- or bispecific molecule.

The present invention thus provides methods for identifying agents capable of inducing effector cell responses such as ADCC or NK cell mediated immune responses. In particular, the invention provides methods of identifying agents capable of inducing Fc-mediated effector cell responses, specifically FcγIII-mediated effector cell responses. A putative agents' ability to induce such responses can be assessed by, for example, analyzing cytokines levels. For example, the effectiveness of the putative agent can be assessed by measuring baseline levels of one or more cytokines associated with FcγIII-mediated effector cell responses in a first transgenic animal expressing human CD16 and comparing with levels after administration in the animal. Alternatively, a comparison can be made between a first transgenic animal expressing human CD16 to which the agent has been administered and a second transgenic animal to which either no agent has been administered or a placebo or control substance has been administered. The specificity of the agent can be assessed by comparing the agents' effect on a transgenic animal expressing human CD16 with that on a transgenic animal having a disrupted endogenous CD16 gene (i.e., a CD16 knockout) and/or with the wild-type animal (i.e., having a functional endogenous CD16). An increase in cytokine levels associated with human FcγIII-mediated effector cell responses in a transgenic animal expressing human CD16 is an indication of the agents' effectiveness in inducing such a response in a human subject.

One aspect of the invention comprises administering a putative agent to each of the human CD20 and human CD20/CD16 transgenic animals and comparing the effectiveness of the agent, for example, for killing or depletion of human CD20 B cells. One embodiment is a method of identifying an agent capable of inducing an Fc-mediated effector cell response against B lymphocytes expressing human CD20 comprising administering an agent to the CD20 transgenic animal; measuring the level of B lymphocytes expressing human CD20 in the CD20 transgenic animal; determining the percent reduction in the level of B lymphocytes; administering the agent to the $CD20^+/CD16^+$ transgenic animal; measuring the level of B lymphocytes expressing human CD20 in the $CD20^+/CD16^+$ transgenic animal; and determining the percent reduction in the level of B lymphocytes in the $CD20^+/CD16^+$ animal; wherein if the percent reduction of B lymphocytes determined in the $CD20^+/CD16^+$ animal is greater than the percent reduction determined in the CD20 animal, the agent is identified as capable of inducing an Fc-mediated effector cell response against B lymphocytes expressing human CD20.

To detect antibody binding following administration of an anti-CD16 and/or anti-CD20 antibody, or bi- or multispecific molecule to a transgenic animal, any suitable assay can be used. For example, a sample of the animal's blood can be taken and assayed for the presence of anti-CD antibody-CD complexes using screening assays known in the art, such as an enzyme-linked immunosorbent assay (ELISA), a radioimmunoassay (RIA), or a Western Blot Assay. Each of these assays generally detects the presence of protein-antibody complexes of particular interest by employing a labeled reagent (e.g., an antibody) specific for the complex of interest. Accordingly, in the present invention, these assays are used to detect CD-antibody complexes formed between immunoglobulins (e.g., IgG, IgA etc.) contained in the animal's blood serum and human CD markers contained on the surface of particular cells in the animal.

The CD marker-antibody complexes can be detected using e.g., an enzyme-linked antibody or antibody fragment that recognizes and specifically binds to the antibody-CD marker complexes. Alternatively, the complexes can be detected using any of a variety of other immunoassays. For example, the antibody can be radioactively labeled and used in a radioimmunoassay (RIA). The radioactive isotope can be detected by such means as the use of a gamma counter or a scintillation counter or by autoradiography.

To detect an immune response following administration of an antibody, or bi- or multispecific molecule or other agent to a transgenic animal, any suitable procedure for measuring a change in the concentration of e.g., a cytokine, antibody or T cell population in the plasma or serum of the animal can be used. For example, a change in a cytokine concentration in vivo can be detected via a variety of immunoassays, such as enzyme immunoassay (EIA), radioimmunoassay (RIA) or ELISPOT assay. Exemplary cytokines that can be assayed include: granulocyte/macrophage colony stimulating factor (GM-CSF), granulocyte colony-stimulating factor (G-CSF), macrophage colony-stimulating factor (M-CSF), interleukins 1-12 (IL-1 to IL-12).

For example, plasma can be obtained from a transgenic animal to which an antibody, bispecific, or multi specific molecule or other agent has been administered. The concentration of a cytokine can be measured using an EIA by detecting the interaction of the cytokine with an antibody, which is in turn conjugated to an enzyme. The activity of the enzyme is detected by the reaction with an appropriate substrate, preferably a chromogenic substrate, in such a manner as to produce a chemical moiety which can be detected, for example, by spectrophotometric, fluorimetric or by visual means (Voller, "The Enzyme Linked Immunosorbent Assay (ELISA)", Diagnostic Horizons 2:1-7, 1978, Microbiological Associates Quarterly Publication, Walkersville, Md.; Voller, et al., J. Clin. Pathol. 31:507-520 (1978); Butler, Meth. Enzymol. 73:482-523 (1981); Maggio, (ed.) Enzyme Immunoassay, CRC Press, Boca Raton, Fla., 1980; Ishikawa, et al., (eds.) Enzyme Immunoassay, Kgaku Shoin, Tokyo, 1981). Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards or using RIA.

It is also possible to label the anti-cytokine antibody or anti CD20 agent with a fluorescent compound. When the fluorescently labeled antibody is exposed to light of the proper wave length, its presence can then be detected. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. The presence of the chemiluminescent-tagged antibody is then determined by detecting luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the antibody. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

A non-human transgenic animal of the present invention can further provide an indication of the safety of a particular agent for administration to a human. For example, a humanized antibody or other agent can be administered to the transgenic animal and any toxic or adverse effects as a result of the administration of the agent to the animal can be monitored as an indication of the safety and tolerability of the humanized antibody or agent for in vivo human use. Adverse events that may occur on a short term basis include headache, infection, fever, chills, pain, nausea, asthenia, pharyngitis, diarrhea, rhinitis, infusion reactions, and myalgia. Short term adverse events are measured in days post treatment. Long term adverse effects include cytoxicity of certain cell types, bleeding events due to thrombocytopenia, release of mediators due to inflammatory and/or allergic reactions, inhibition of the immune system and/or development of an anti-therapeutic agent antibody, end organ toxicity, and increased incidence of infection or malignancy. Long term adverse events are measured in months post treatment.

Another aspect of the invention involves a method for determining efficacy of an anti-CD20 agent. Efficacy can be determined by administering a range of doses of the agent to set of trangenic animals having human CD20 and/or human CD16 alpha chain, determining at least one dose that results in a decrease in cells bearing human CD20.

The transgenic animals of the present invention, including cells, tissues, or other materials derived therefrom, can be utilized as models for diseases, especially diseases associated or mediated by CD20 bearing cells. Animals of any species, including, but not limited to, mice, rats, rabbits, guinea pigs, pigs, micro-pigs, goats, and non-human primates, e.g., baboons, monkeys, and chimpanzees may be used to generate disease animal models. These systems may be used in a variety of applications. Such assays may be utilized as part of screening strategies designed to identify agents, such as compounds that are capable of ameliorating disease symptoms. Thus, the animal- and cell-based models may be used to identify drugs, pharmaceuticals, therapies and interventions that may be effective in treating disease.

Cell-based systems may be used to identify compounds that may act to ameliorate disease symptoms. For example, such cell systems may be exposed to a compound suspected of exhibiting an ability to ameliorate disease symptoms, at a sufficient concentration and for a time sufficient to elicit such an amelioration of disease symptoms in the exposed cells. After exposure, the cells are examined to determine whether one or more of the disease cellular phenotypes has been altered to resemble a more normal or more wild-type, non-disease phenotype.

Other uses will be readily apparent to one of skill in the art.

The following non-limiting examples are illustrative of the present invention. All documents cited herein are hereby expressly incorporated by reference.

EXAMPLES

Example 1

This example describes generation of human CD20 BAC transgenic (Tg+) mice and a study of the effects of anti-human CD20 antibody treatment in the hCD20+ mice.

Figure 1:
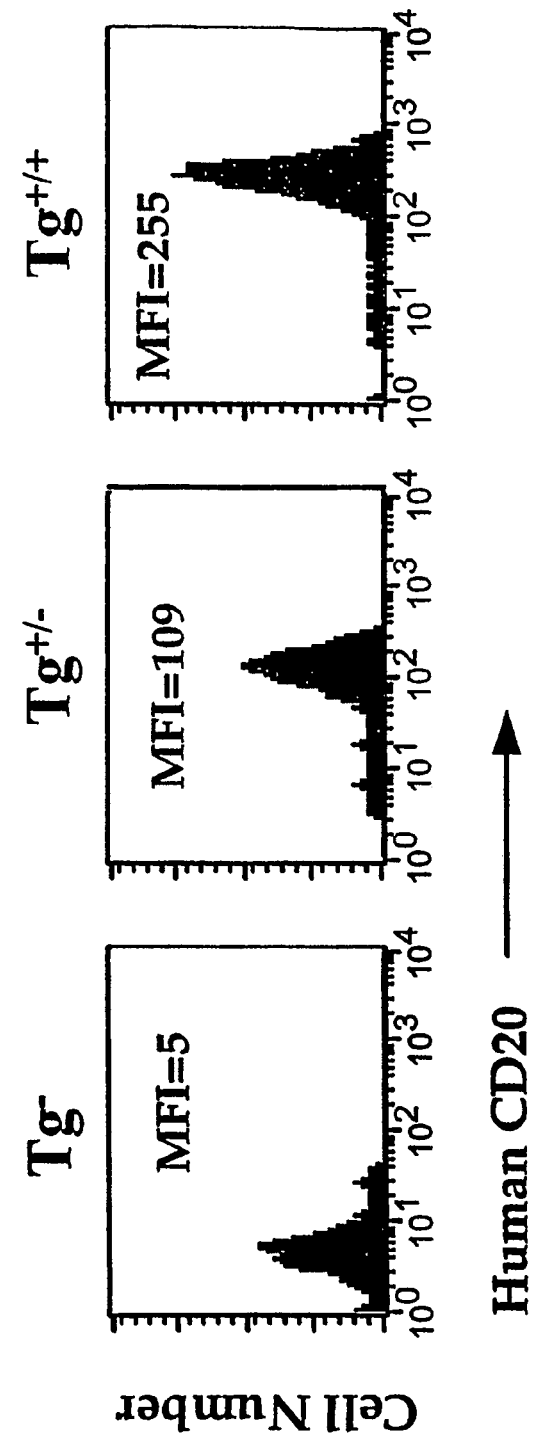
FIG. 1 shows the expression of human CD20 in mouse B220$^+$ cells derived from mice without the transgene (Tg−), heterozygous (Tg+/−) and homozygous (Tg+/+) for the transgene.

Human CD20 transgenic mice were generated using human CD20 CITB Human BAC-D-Clone No. 117H19 from Invitrogen. (Invitrogen, Carlsbad, Calif.) DNA encoding human CD20 was isolated from human lymphocytes and was sent to Invitrogen. Invitrogen tested the DNA against the filters with the clones from the human BAC library and identified clone 117H19. Previous attempts to generate transgenic mice expressing human CD20 were not successful, possibly due in part to the failure to include sufficient transcriptional control regions in the transgene construct. Transgenic mice were generated by micro injecting a human CD20 BAC construct prepared with clone 117H19 into a fertilized egg of FVB inbred strain of mice. The fertilized eggs were incubated for 1-7 days and then were implanted into surrogate mice. Mice were screened based on the FACS analysis of human CD20 expression. As can be seen from the FACS plots in FIG. 1, mice heterozygous (Tg+/−) and homozygous (Tg+/+) for the transgene express human CD20 on their B220+ B cells. The murine CD20 gene was not intentionally disrupted.

Figure 2:
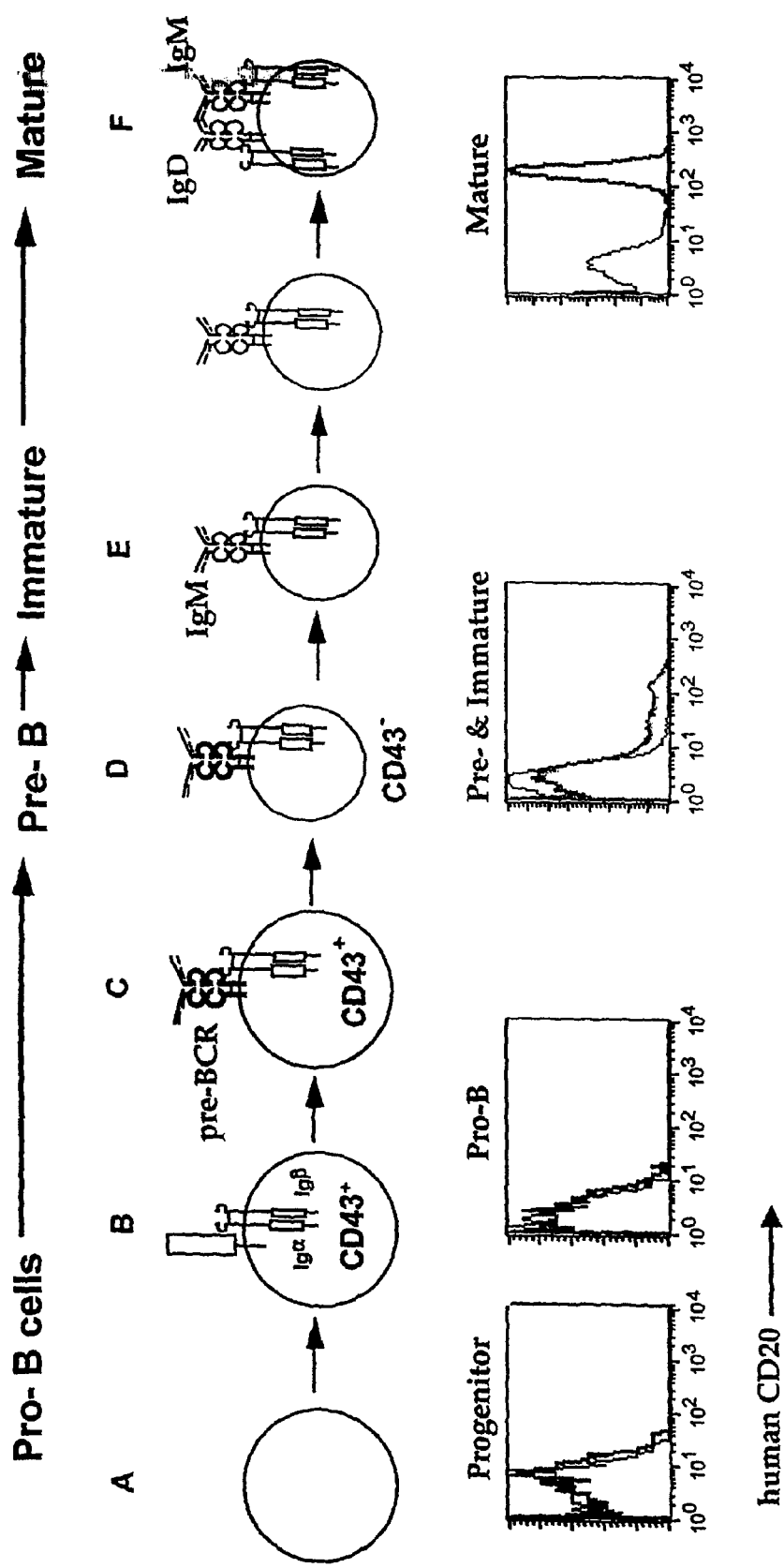
FIG. 2 provides a schematic diagram of expression of various cell surface markers (CD43, IgM, IgD) during B cell differentiation and maturation. In the Tg+ mice, hCD20 is expressed on pre-B, immature B cells and mature B cells.
Figure 3:
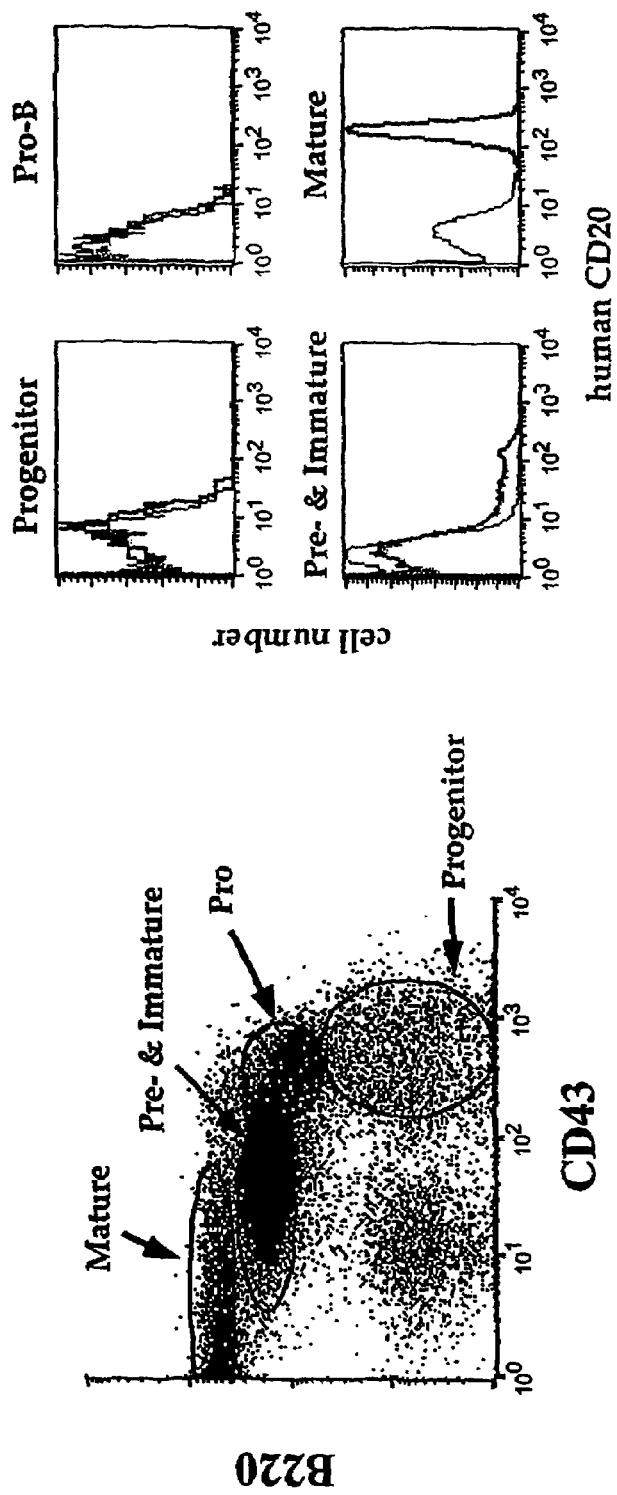
FIG. 3 shows the result of screening Tg+ mice for human CD20 expression in the B cells of the bone marrow. Cells were stained with anti-human CD20 conjugated to FITC (BD Pharmingen). Gating the cells for presence of B220 and CD43 allows delineation into the various populations of B cells. For gating, cells were stained with anti-B220 Ab conjugated to PerCP (BD Pharmingen) and with anti-CD43 Ab conjugated to PE (fluorescence, BD Pharmingen).
Figure 4:
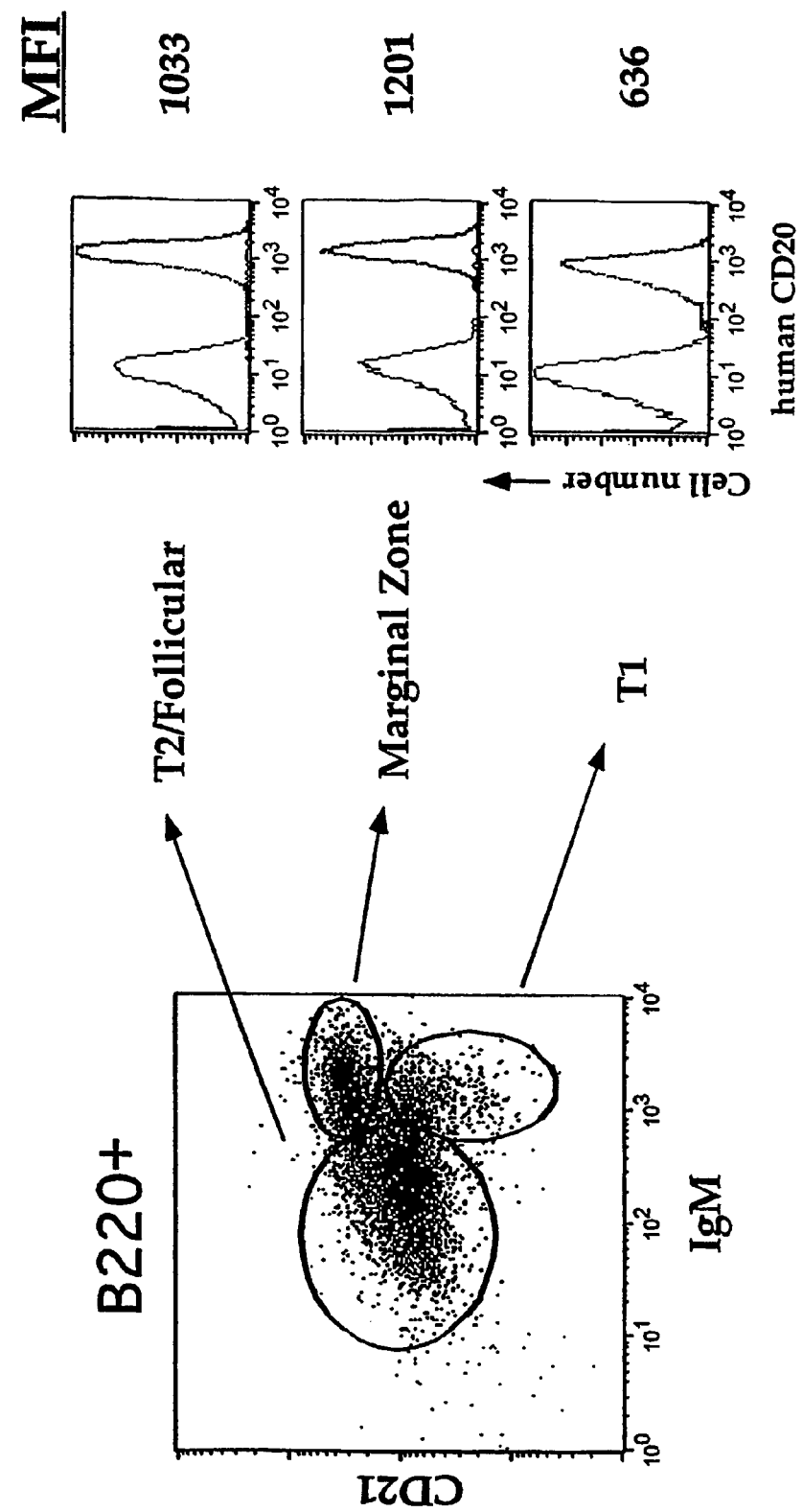
FIG. 4 shows the result of screening Tg+ mice for human CD20 expression in the B cells of the spleen. Cells were stained with anti-human CD20 conjugated to FIT C (BD Pharmingen). Gating the cells for B220 and CD21 allows delineation into the various populations of B cells. For gating, cells were stained with anti-B220 Ab conjugated to PerCP (BD Pharmingen) and with anti-CD21 Ab conjugated to PE (fluorescence, BD Pharmingen). B cells with human CD20 are found in the T1 zone, marginal zone and T2/Follicular zone.
Figure 5:
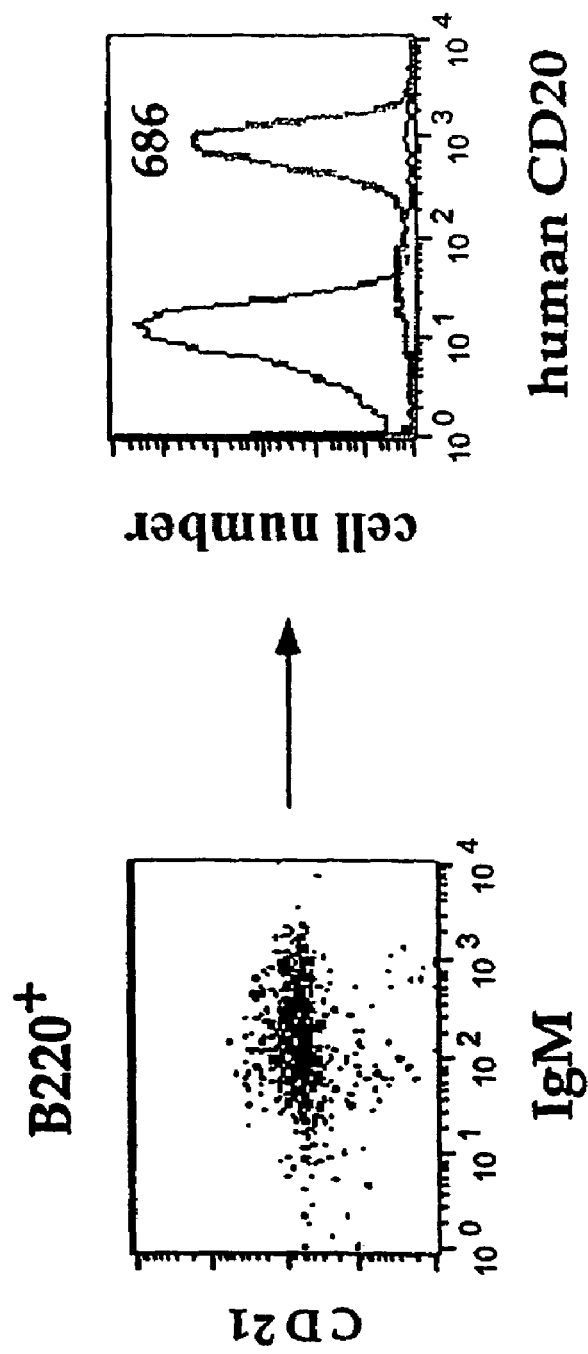
FIG. 5 shows the result of screening Tg+ mice for human CD20 expression in the B cells of the mesenteric lymph nodes. Cells were stained with anti-human CD20 conjugated to FITC (BD Pharmingen). Gating the cells for B220 and CD21 allows delineation into the various populations of B cells. For gating, cells were stained with anti-B220 Ab conjugated to PerCP (BD Pharmingen) and with anti-CD21 Ab conjugated to PE (fluorescence, BD Pharmingen).
Figure 6:
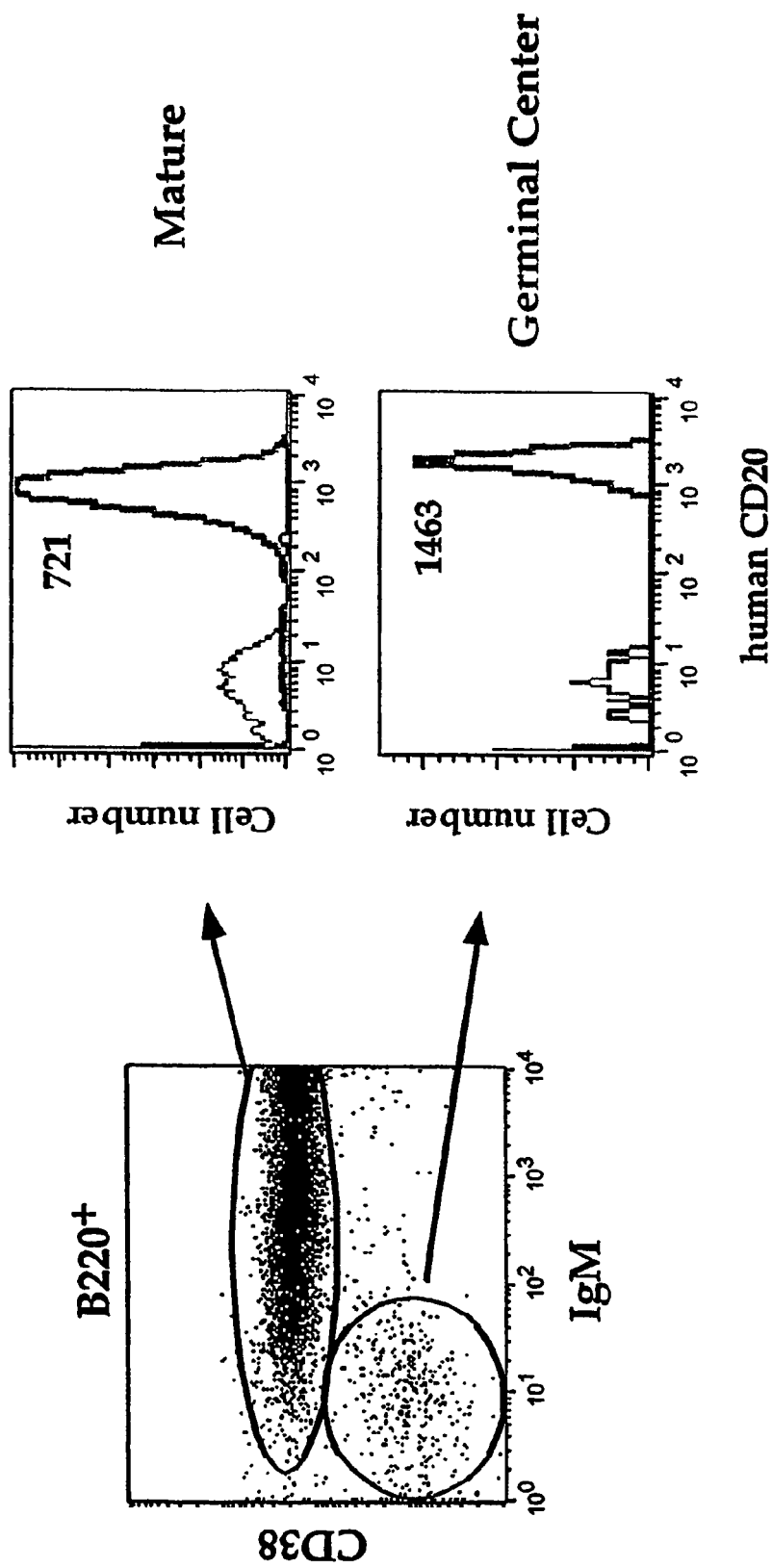
FIG. 6 shows the result of screening Tg+ mice for human CD20 expression in the B cells of the Peyer's Patches. Cells were stained with anti-human CD20 conjugated to FITC (BD Pharmingen). Gating the cells for B220 and CD38 allows delineation into the various populations of B cells. For gating, cells were stained with anti-B220 Ab conjugated to PerCP (BD Pharmingen) and with anti-CD38 Ab conjugated to PE (fluorescence, BD Pharmingen). B cells with human CD20 are mature B cells and cells in the germinal centers.

FIG. 2 provides a schematic diagram of expression of various cell surface markers (CD43, IgM, IgD) during B cell differentiation and maturation. In the Tg+ mice, hCD20 is expressed on pre-B, immature B cells and mature B cells. Human CD20 is found on the same cell types as that of humans and is expressed on these cell types at a comparable to slightly lower level as on human B cells.

The Tg+ mice were screened for human CD20 expression in the B cells of the bone marrow, spleen, mesenteric LN and Peyer's patches using anti-human CD20 antibodies conjugated to FITC (BD Pharmingen) (results are shown in FIGS. 3-6). Gating the cells on B220 and CD43, CD21, or CD38 allows delineation into the various populations of B cells from the different tissues. For gating, cells were stained with anti-B220 Ab conjugated to PerCP (BD Biosciences) and with anti-CD43 Ab, anti-CD21 Ab or anti-CD38 Ab conjugated to PE (fluorescence, Becton Dickinson).

The level of expression of human CD20 on transgenic mice peripheral blood cells was compared to that of human CD20 on human peripheral blood cells using FACS analysis and calculating mean fluorescent intensity. Peripheral blood cells were obtained from human donos and from a hCD20Tg+ mice and stained with labeled anti-human CD20 antibody (mH27). The cells were analyzed by FACS and were gated on human CD19+ and B220+ populations. FIG. 28 shows a representative comparison of the expression level of human CD20 expression on peripheral blood cells from a human CD20 transgenic mouse as compared to expression of CD20 on human peripheral blood cells. The numbers on the graph represent mean fluorescence intensity. The results show that the human CD20 on transgenic cells was expressed at a level about 40% of human CD20 on human cells.

These results show that B cells obtained from many different tissues in the transgenic mice express human CD20 marker. The human CD20 marker is found predominantly on mature B cells but also can be found on pre-B and immature B cells similar to the profile observed in humans.

The transgenic mice were then treated with anti-human CD20 mAb m2H7 in order to determine if the antibody treatment would result in B cell depletion. The antibody m2H7 can be obtained from BD PharMingen (San Diego, Calif.), eBioscience, or Calbiochem. The anti-human CD20 activity of m2H7 was compared to that of Rituxan in vitro assays and had comparable activity. A humanized antibody, such as Rituxan, could also be utilized in the cell killing studies because cell killing in vivo occurs over a short enough period of time that an immune response to the humanized antibody is not a concern.

Figure 7:
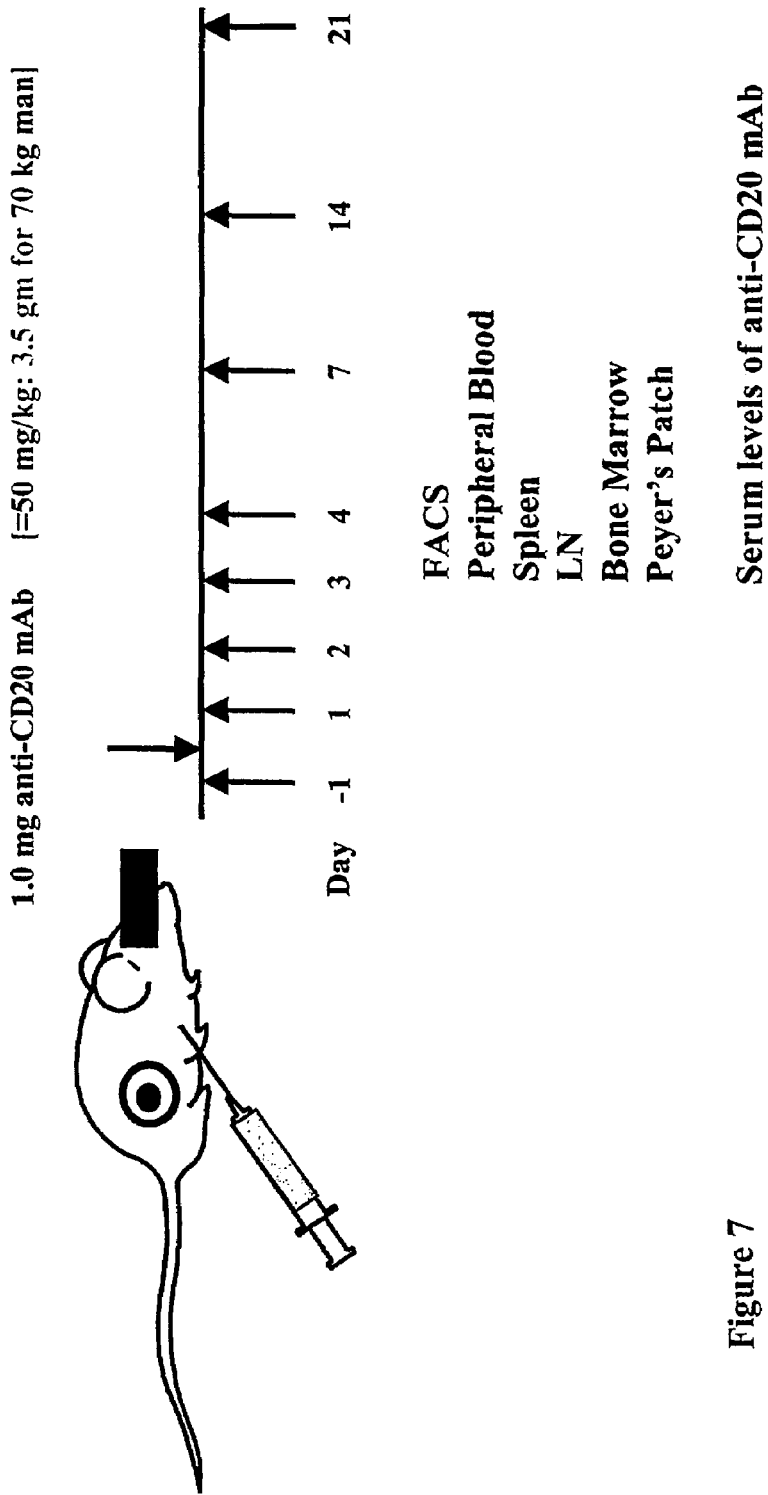
FIG. 7 is a schematic diagram of administration of anti-human CD20 mAb into Tg+ mice and analysis of presence or absence of cells having human CD20. A single dose of 1 mg of anti-human CD20 monoclonal antibody was administered at day 0. Samples were taken from various tissues at day −1, day 1, 2, 3, 4, 7, 14 and 21. Samples from different tissues such as peripheral blood spleen, lymph nodes, bone marrow, and Peyer's Patches were analyzed by FACs as described previously. Serum levels of anti-CD20 monoclonal antibody were also monitored.
Figure 8:
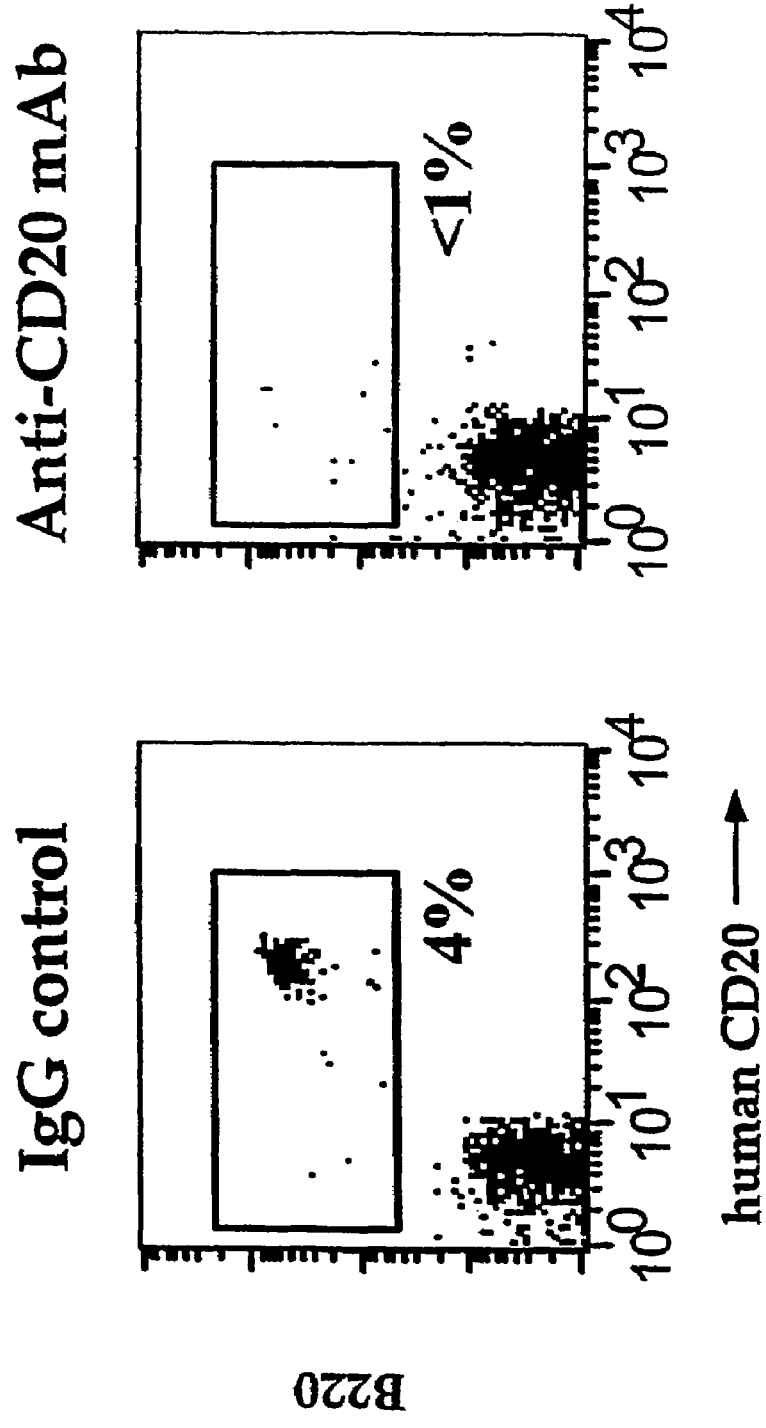
FIG. 8 shows depletion of peripheral B cells in transgenic mice treated with anti-human CD20 mAb m2H7 (BD Pharmingen). The antibodies were administered to the transgenic mice as outlined in the schematic in FIG. 7 at a dose of 1 mg total. FACS analyses were done on peripheral blood, spleen, lymph node, bone marrow, and Peyer's Patches with gating as described previously.
Figure 9:
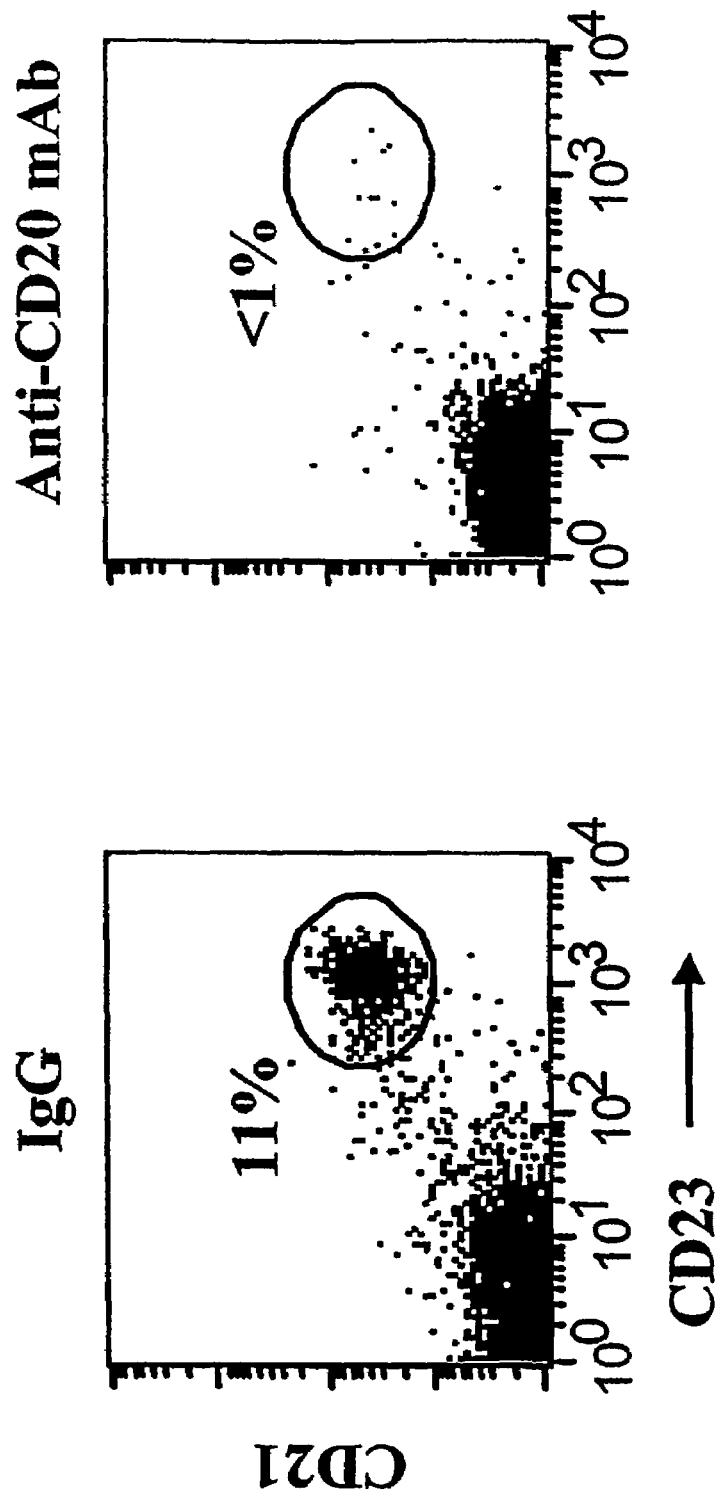
FIG. 9 shows depletion of mature peripheral lymph node B cells in transgenic mice treated with anti-human CD20 mAb m2H7. The antibodies were administered to the transgenic mice as outlined in the schematic in FIG. 7 at a dose of 1 mg total. FACS analyses were done on peripheral blood, spleen, lymph node, bone marrow, and Peyer's Patches with gating as described previously.
Figure 10:
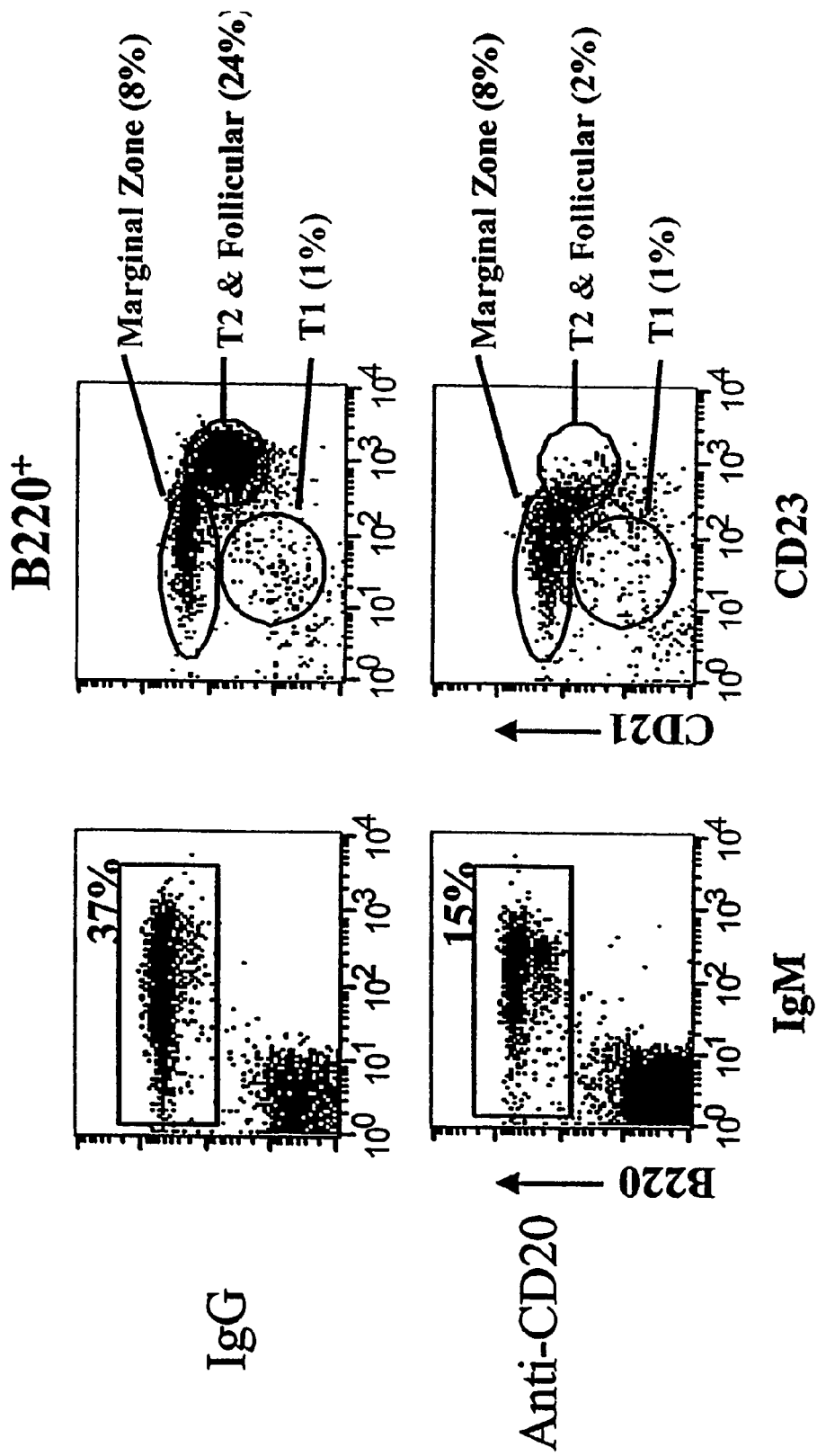
FIG. 10 shows depletion of splenic T2 and follicular B cells in transgenic mice treated with anti-human CD20 mAb m2H7. The antibodies were administered to the transgenic mice as outlined in the schematic in FIG. 7 at a dose of 1 mg total. FACS analyses were done on peripheral blood, spleen, lymph node, bone marrow, and Peyer's Patches with gating as described previously.
Figure 11:
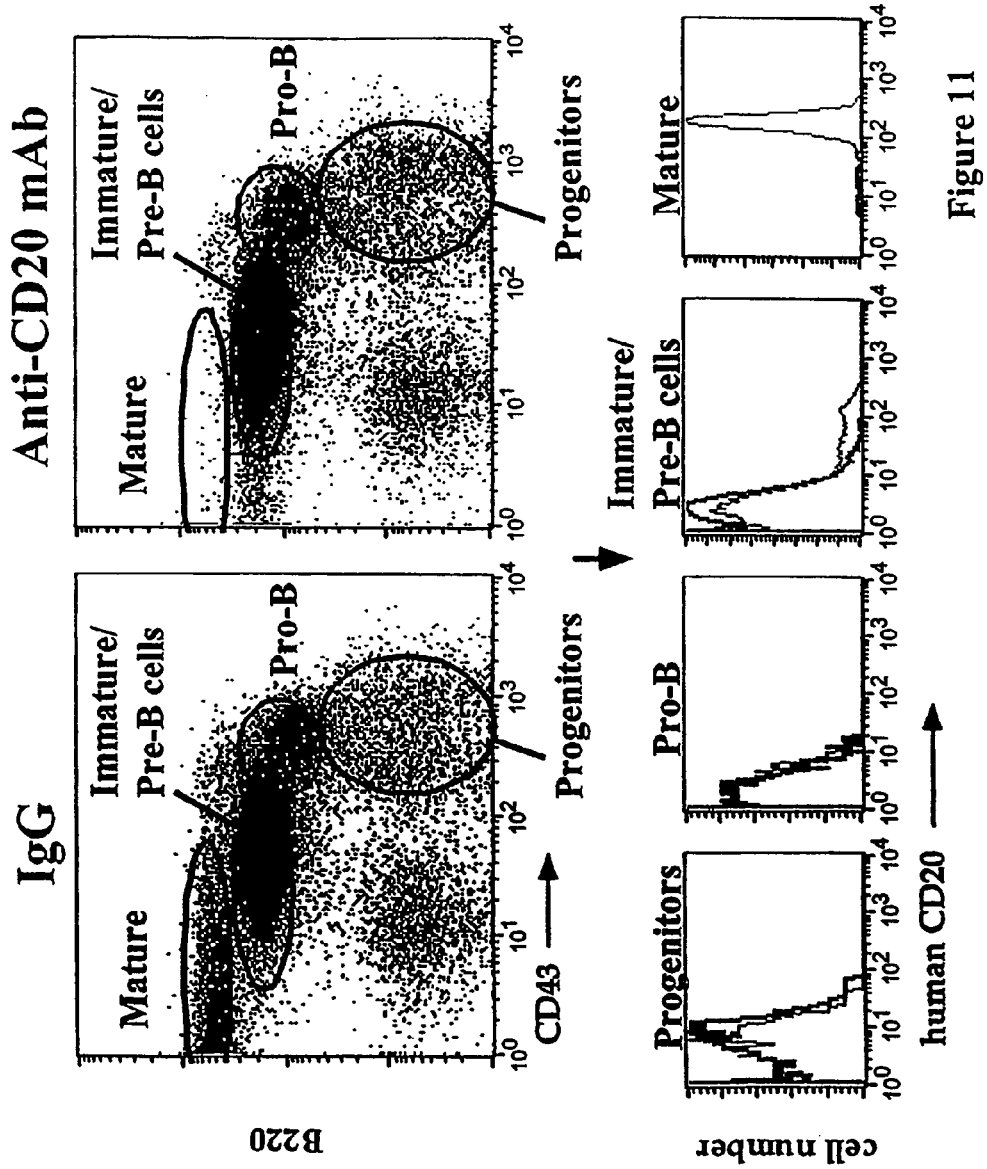
FIG. 11 shows depletion of re-circulating mature B cells in transgenic mice treated with anti-human CD20 mAb m2H7. The antibodies were administered to the transgenic mice as outlined in the schematic in FIG. 7 at a dose of 1 mg total. FACS analyses were done on peripheral blood, spleen, lymph node, bone marrow, and Peyer's Patches with gating as described previously.

The antibody m2H7 was administered to the transgenic mice as outlined in the schematic in FIG. 7 at a dose of 1 mg total which is equivalent to 3.5 mg for a 70 kg person. FACS analyses were done on peripheral blood, spleen, lymph node, bone marrow, and Peyer's Patches at the days indicated by the arrows. Serum levels of anti-CD20 mAb were monitored.

Figure 12:
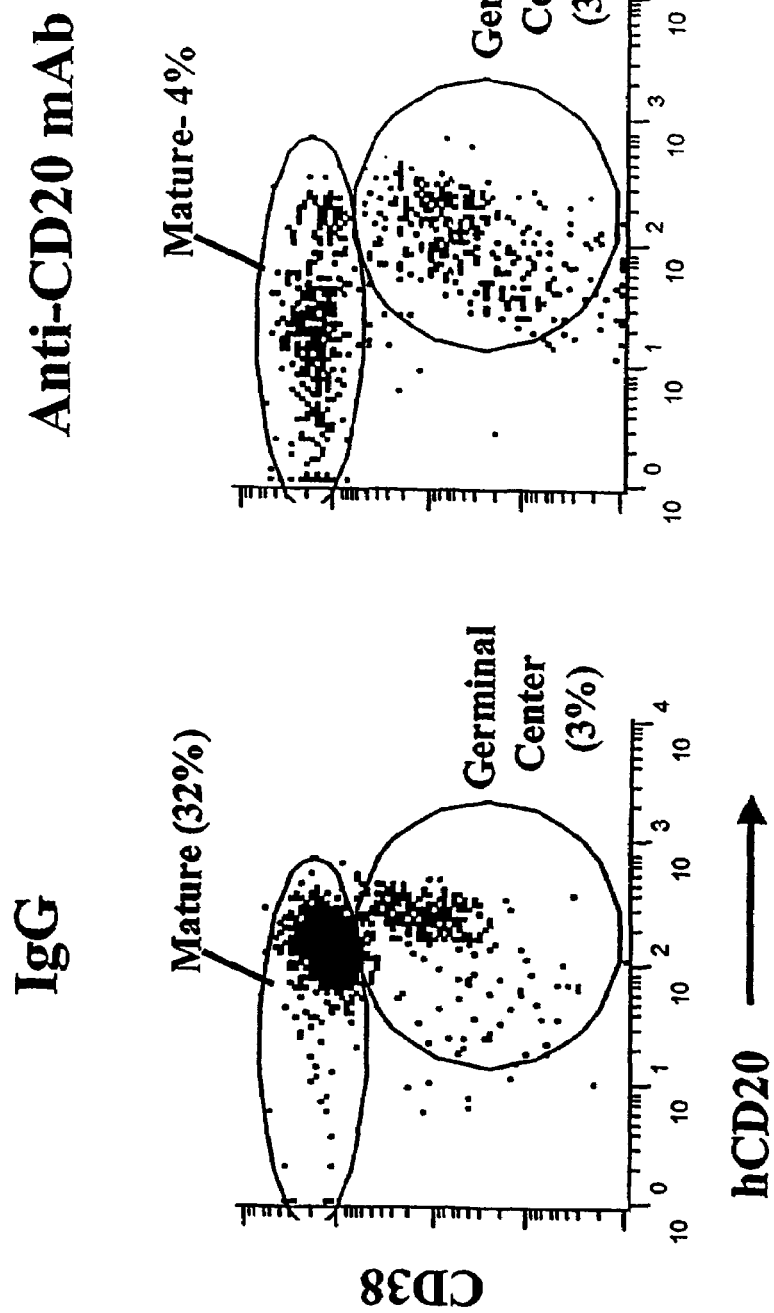
FIG. 12 shows depletion of mature B cells and resistance of Peyer's Patches germinal center B cells to depletion in transgenic mice treated with anti-human CD20 mAb m2H7. The antibodies were administered to the transgenic mice as outlined in the schematic in FIG. 7 at a dose of 1 mg total. FACS analyses were done on peripheral blood, spleen, lymph node, bone marrow, and Peyer's Patches with gating as described previously.
Figure 14:
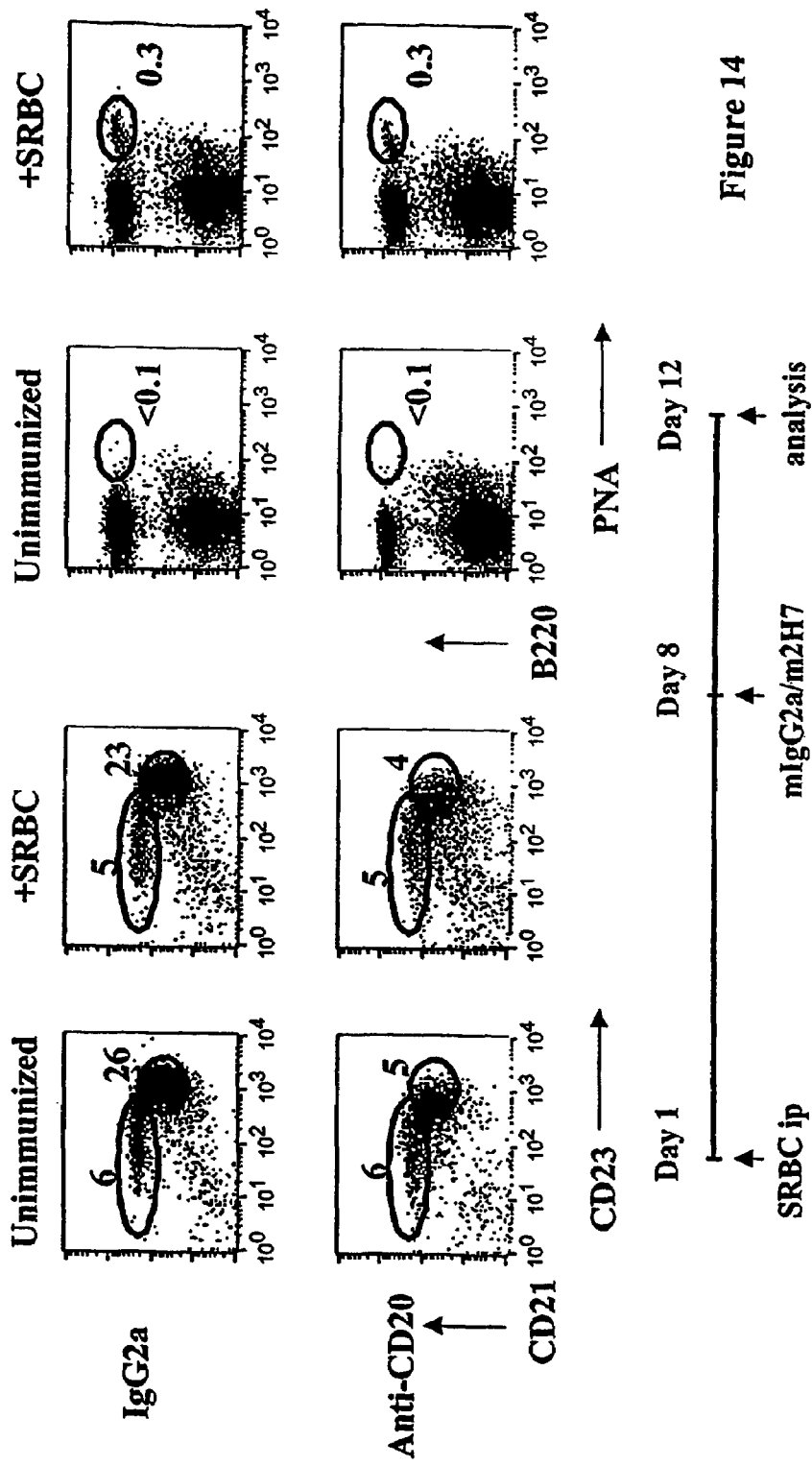
FIG. 14 shows FACS plot indicating resistance of splenic germinal center B cells to short-term anti-CD20 mAb therapy. Mice were unimmunized or immunized with sheep red blood cells (SRBC) by intraperitoneal injection at day 1 to induce germinal centers in the spleen. The germinal centers appear by day 7. At day 8, one group of mice was treated with anti-CD20 antibody m2H7. The control set of mice was treated with mIgG2a isotype control antibody. Spleen cells from the mice were analyzed at day 12. PNA (peanut agglutinin), which stains for germinal center, was utilized. No detectable germinal center cells were seen in the spleens of mice not immunized with SRBC whereas the spleens of immunized mice show 0.3% PNA staining cells. While T2/Follicular B cells are depleted with anti-CD20 antibody treatment, marginal center B cells in the spleen are resistant to the antibody.

Treatment of Tg+ mice with anti-CD20 mAb (m2H7) alone results in depletion of B cells in peripheral blood, mature peripheral lymph node B cells, T2 and follicular B cells in the spleen (see FIGS. 8-11). However, it was also observed that certain B cell subsets are resistant to killing by anti-CD20 antibody despite very high, likely saturating levels, of antibody on the cell surface. These resistant B cells are the marginal zone B cells in the spleen (FIG. 10), and the germinal center B cells in both the Peyer's patches (FIG. 12) and spleen (FIG. 14). In FIG. 14, mice were injected with a first dose of anti-CD20 mAb at 100 ug on day 1, followed by a second, 100 ug dose on day 3 (it is likely that a single dose at 50 ug was sufficient to saturate the B cells). T2/follicular B cells were depleted but the germinal center B cells from the Peyer's patches were shown to be bound with anti-CD20 mAb but were resistant to killing.

Figure 13:
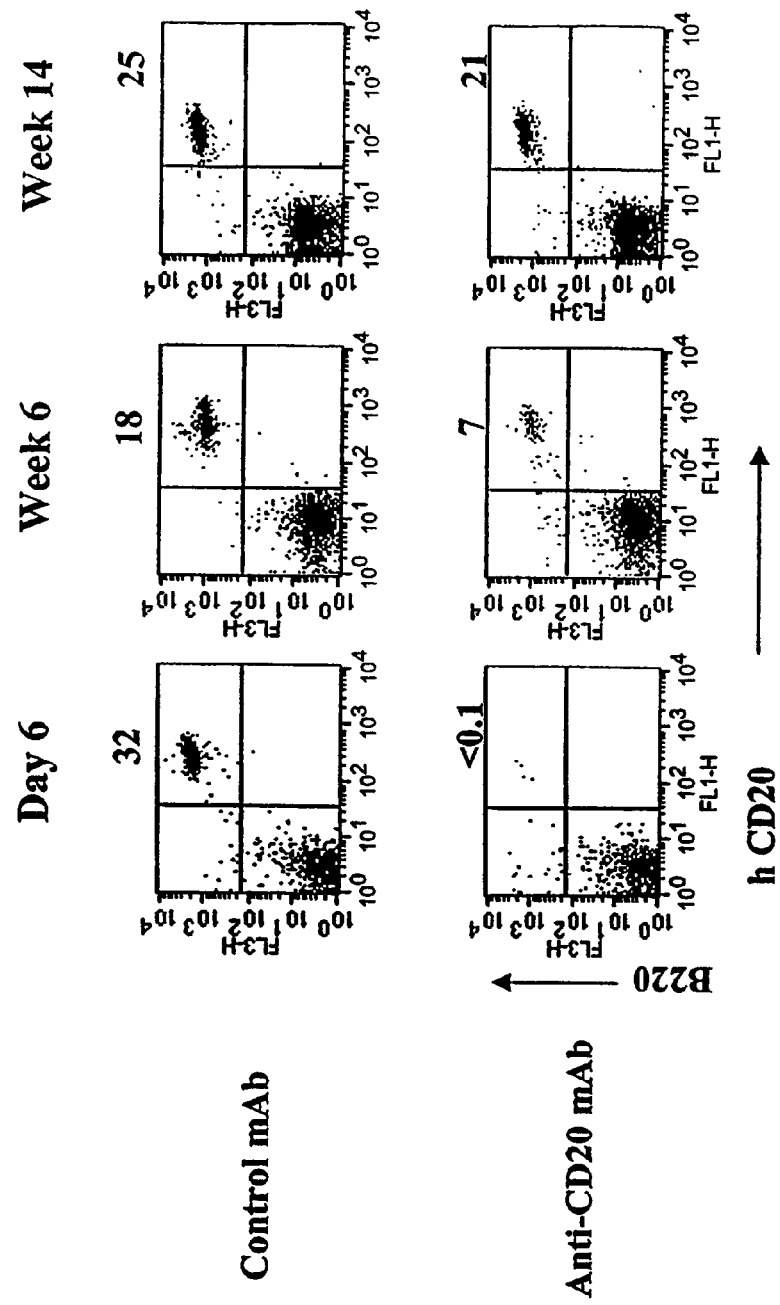
FIG. 13 shows depletion and recovery of B cells following administration of anti-CD20 mAb. Antibody was administered to the mice at day 1. At day 6 post antibody treatment, B cells expressing human CD20 in the peripheral blood were not detectable. At week 6, upon clearance of the antibody, hCD20+ cells begin to be detected. By week 14, B cells appeared to have recovered to normal levels. Recovery results from precursor B cells which do not express CD20 and that then subsequently develop into mature B cells with human CD20+.

The recovery of B cells following anti-human CD20 antibody treatment was studied. Antibody was administered to the mice at day 1. FIG. 13 shows that at day 6 post antibody treatment, B cells in the peripheral blood were not detectable. At week 6, upon clearance of the antibody, hCD20+ cells begin to be detected and by week 14, B cells appeared to have recovered to normal levels. Recovery results from precursor B cells which do not express CD20, which then subsequently develop into mature B cells with human CD20+.

FIG. 14 shows FACS plots demonstrating resistance of splenic germinal center B cells to short-term (single injection) anti-CD20 mAb treatment. Mice were unimmunized or immunized with sheep red blood cells (SRBC) by intraperitoneal injection at day 1 to induce germinal centers in the spleen. The germinal centers appear by day 7. At day 8, one group of mice was treated with m2H7. The control set of mice was treated with mIgG2a isotype control antibody. Spleen cells from the mice were analyzed at day 12. PNA (peanut agglutinin), which stains for germinal center, was utilized. No detectable germinal center cells were seen in the spleens of mice not immunized with SRBC whereas the spleens of immunized mice show 0.3% PNA staining cells. While T2/Follicular B cells are depleted with anti-CD20 antibody treatment, marginal center B cells in the spleen are resistant to the antibody.

Figure 15:
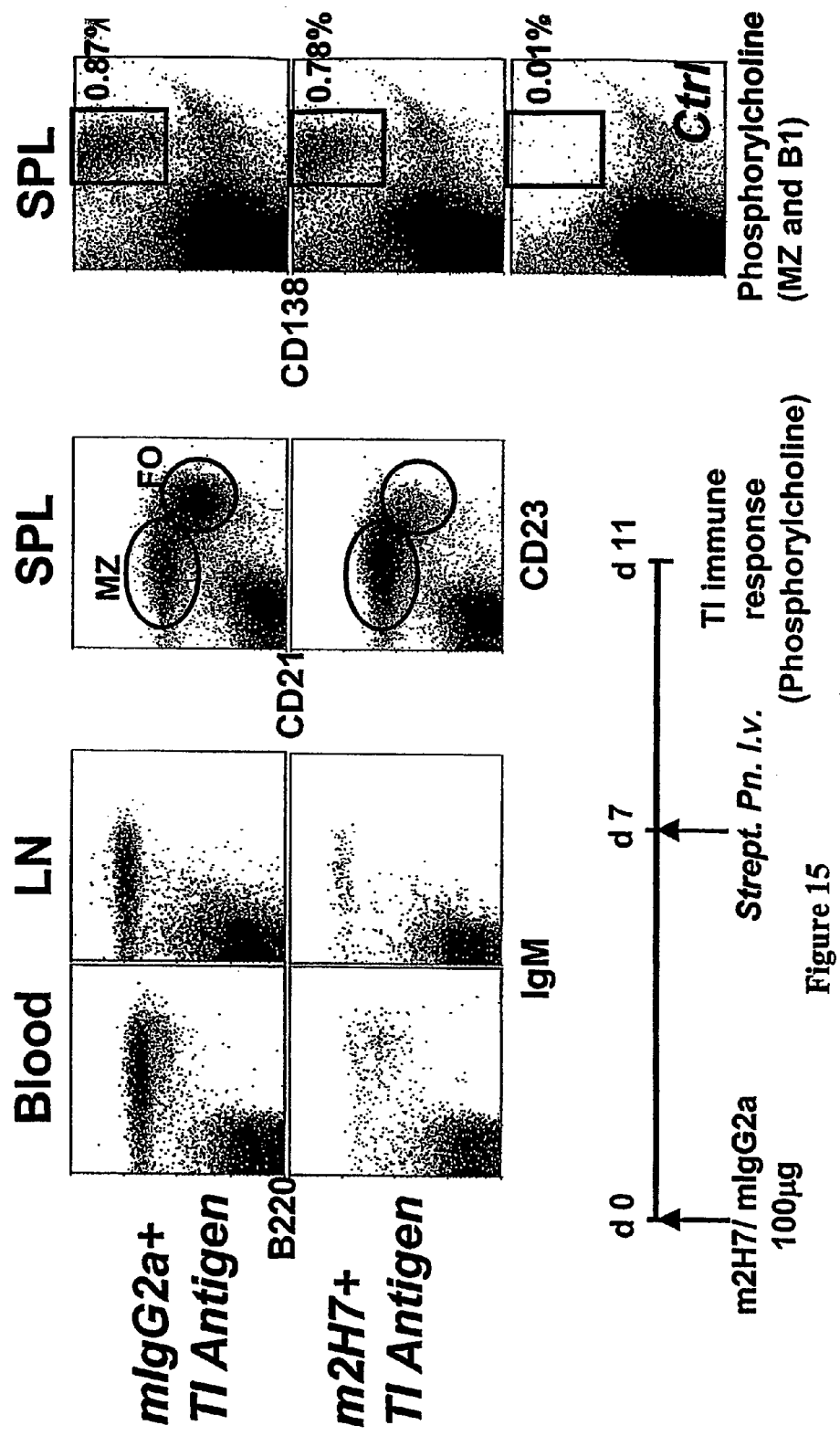
FIG. 15 shows a T cell independent response in anti-CD20 mAb treated mice and controls. Mice were treated with m2H7 or isotype control antibody mIgG2a at day 0. At days 3-7, B cell depletion has occurred. At day 7, the mice were injected i.v. with *Streptococcus Pneumoniae* IV to induce a response to the polysaccharide. A T cell independent response was mounted on day 11. The results demonstrate that treatment with anti-human CD20 m2H7 did not affect the B cell response from the marginal zone and B 1 cells, i.e., the non-depleted MZ and B1 B cells confer protection to T-independent antigens.

Next, it was determined whether upon B cell depletion, the mice were able to develop a T independent immune response. Mice were treated with m2H7 or isotype control antibody mIgG2a at day 0. At days 3-7, B cell depletion has occurred. At day 7, the mice were injected i.v. with *Streptococcus Pneumoniae* IV to induce a response to the polysaccharide. A T cell independent response was mounted on day 11. The results shown in FIG. 15 demonstrated that treatment with anti-human CD20 did not affect the B cell response from the marginal zone and B 1 cells, i.e., the non-depleted MZ and B1 B cells confer protection to T-independent antigens. This data demonstrates that some aspects of humoral immunity, specifically T-independent B cell responses (in this case), are preserved despite treatment with anti-CD20 mAb.

In summary, the human CD20 transgenic animals expressed human CD20 on mature, pre-B and immature B cells in blood, bone marrow, spleen, lymph nodes and Peyer's patches. Human CD20 was expressed on transgenic cells at a level about 40% of that of CD20 expressed on human cells. Treatment of the mice with anti-human CD20 antibodies resulted in significant depletion of B cells within 3-4 days of treatment except for the marginal zone B cells in the spleen (FIG. 10), and the germinal center B cells in both the Peyer's patches (FIG. 12) and spleen (FIG. 14). Not to be bound by any theory, B cell death appears to be mediated by ADCC, complement dependent cytotoxicity (CDC) or apoptosis or a combination of the three. Responses to a T independent antigen were observed in anti-human CD20 treated mice which is consistent with the resistance of splenic marginal zone B cells to depletion by the anti-human CD20 antibody. The B cells that are resistant to killing with anti-human CD20 antibodies provide for retention of T-independent immune response and/or an indication that combination therapy may be required to deplete all of the B cells, if desired. Recovery of B cells expressing human CD20 was observed by 14 weeks after treatment with anti-human CD20 antibodies, most likely due to the maturation of precursor B cells. These results are similar to those seen in humans treated with Rituxan.

Example 2

This example demonstrates the synergy between anti-CD20 mAb and BR3 antagonist treatments for B cell modulation/depletion. BR3-Fc is an immunoadhesin having the extracellular domain of human BR3 fused to constant domain of an immunoglobulin sequence in this case, human IgG1.

Human CD20 transgenic mice expressing (designated as hCD20+ mice) were treated with intraperitoneal injections of anti-CD20 mAb (single injection of 100 micrograms on day 9), BR3-Fc (100 micrograms every other day from days 1 through 12), or the combination of anti-CD20 mAb and BR3-Fc. Each group consisted of 4 mice. Two days following the last injection, the mice were sacrificed and analyzed for hCD20+ B cells. FACS analysis of spleen, blood, lymph node and Peyer's Patches were analyzed for B cell markers (CD21+ CD23+).

Figure 16:
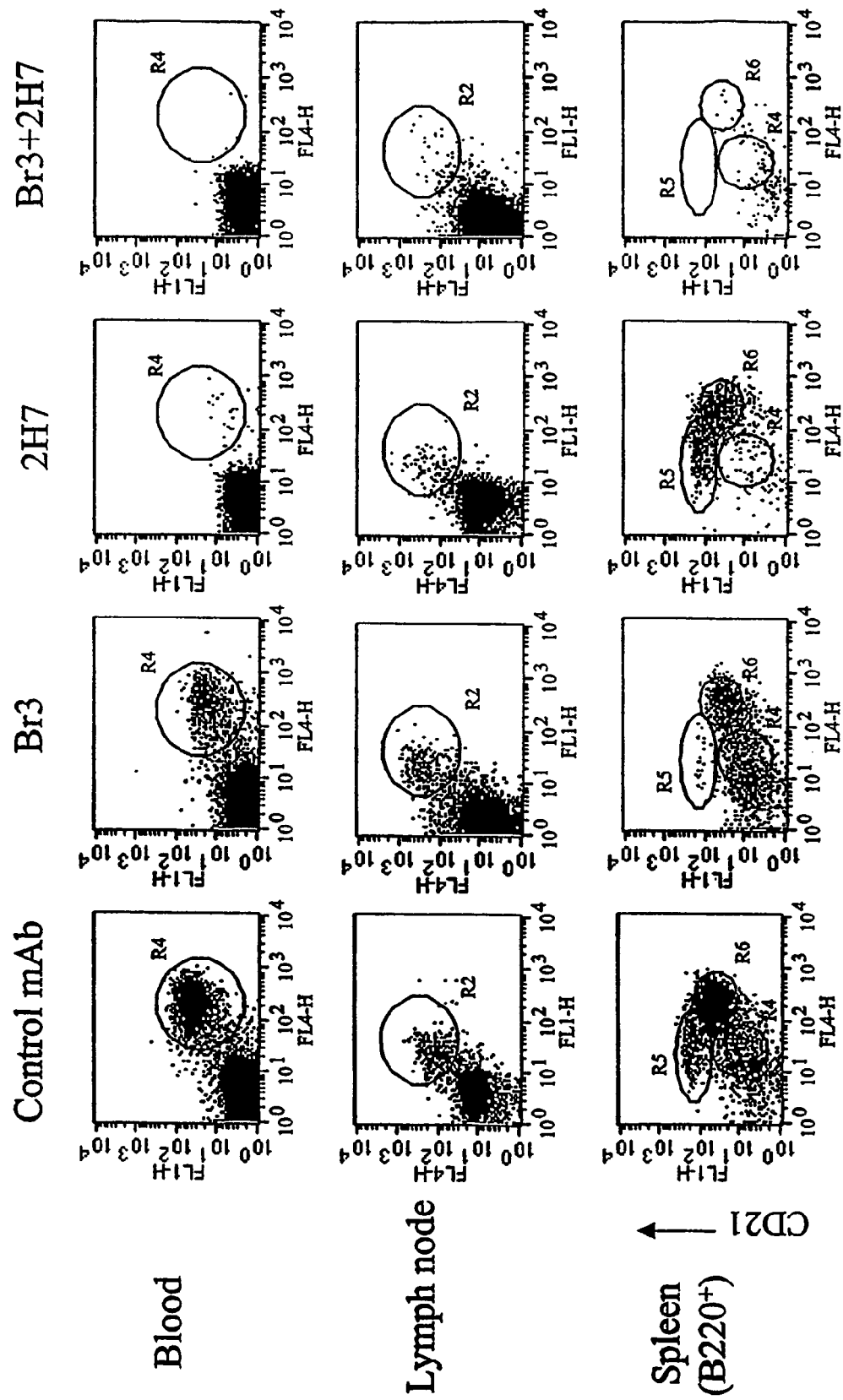
FIG. 16 shows a comparison of the effect of BR3 and 2H7 antibody treatment in Tg+ mice. Human CD20 transgenic mice expressing a bacterial artificial chromosome encoding human CD20 (designated as hCD20+ mice) were treated with intraperitoneal injections of anti-CD20 mAb (single injection of 100 micrograms on day 9), BR3-Fc (100 micrograms every other day from days 1 through 12), or the combination of anti-CD20 mAb and BR3-Fc. Each group consisted of 4 mice. Two days following the last injection, the mice were sacrificed and analyzed for hCD20+ B cells. FACS analysis of spleen, blood, lymph node and Peyer's Patches were analyzed for B cell markers (CD21+CD23+). Anti-CD20 mAb therapy depleted T2 and follicular B cells, but not marginal zone B cells in the spleen, whereas BR3-Fc treatment decreased T2/follicular and marginal zone B cells in the spleen.

The results indicate that anti-CD20 mAb therapy depleted >99% of the mature circulating B cells in the blood and lymph nodes and BR3-Fc treatment decreased mature circulating B cells in the blood and lymph nodes (FIG. 16). Anti-CD20 mAb therapy depleted T2 and follicular B cells, but not marginal zone B cells in the spleen, whereas BR3-Fc treatment decreased T2/follicular and marginal zone B cells in the spleen.

Figure 17:
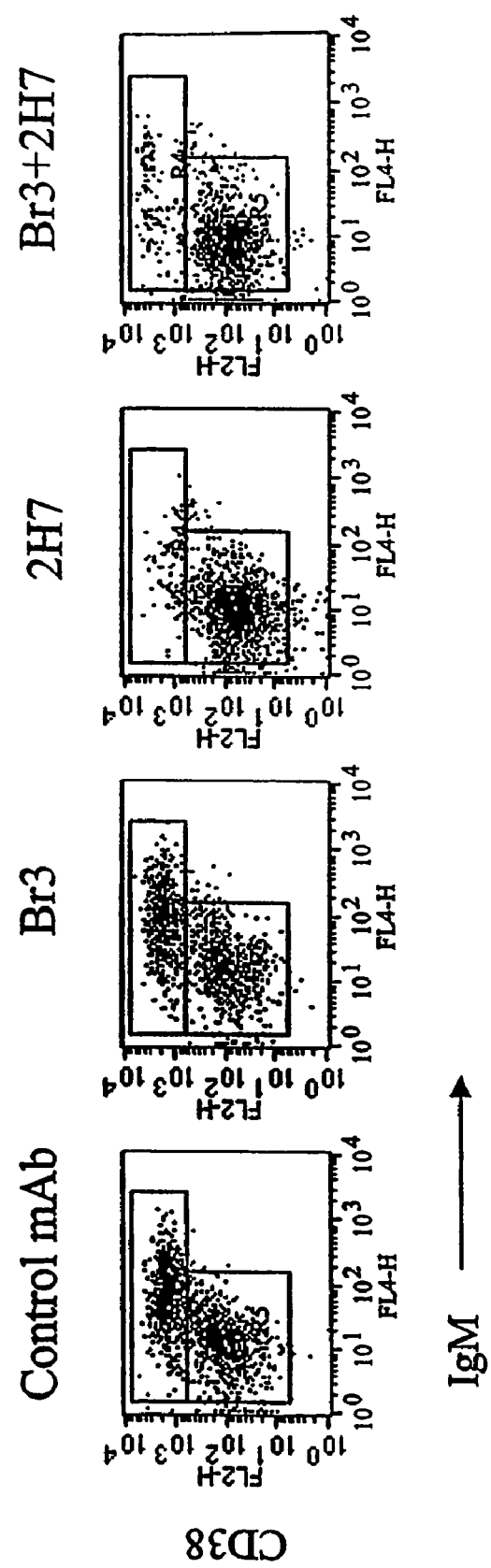
FIG. 17 shows the lack of effect of anti-CD20 mAb treatment on Peyer's Patches. Human CD20 transgenic mice expressing a bacterial artificial chromosome encoding human CD20 (designated as hCD20+ mice) were treated with intraperitoneal injections of anti-CD20 mAb (single injection of 100 micrograms on day 9), BR3-Fc (100 micrograms every other day from days 1 through 12), or the combination of anti-CD20 mAb and BR3-Fc. Each group consisted of 4 mice. Two days following the last injection, the mice were sacrificed and analyzed for hCD20+ B cells. FACS analysis of spleen, blood, lymph node and Peyer's Patches were analyzed for B cell markers (CD21+CD23+). Neither BR3-Fc nor 2H7 nor the combination of the two had an effect on germinal center B cells in Peyer's Patches
Figure 18:
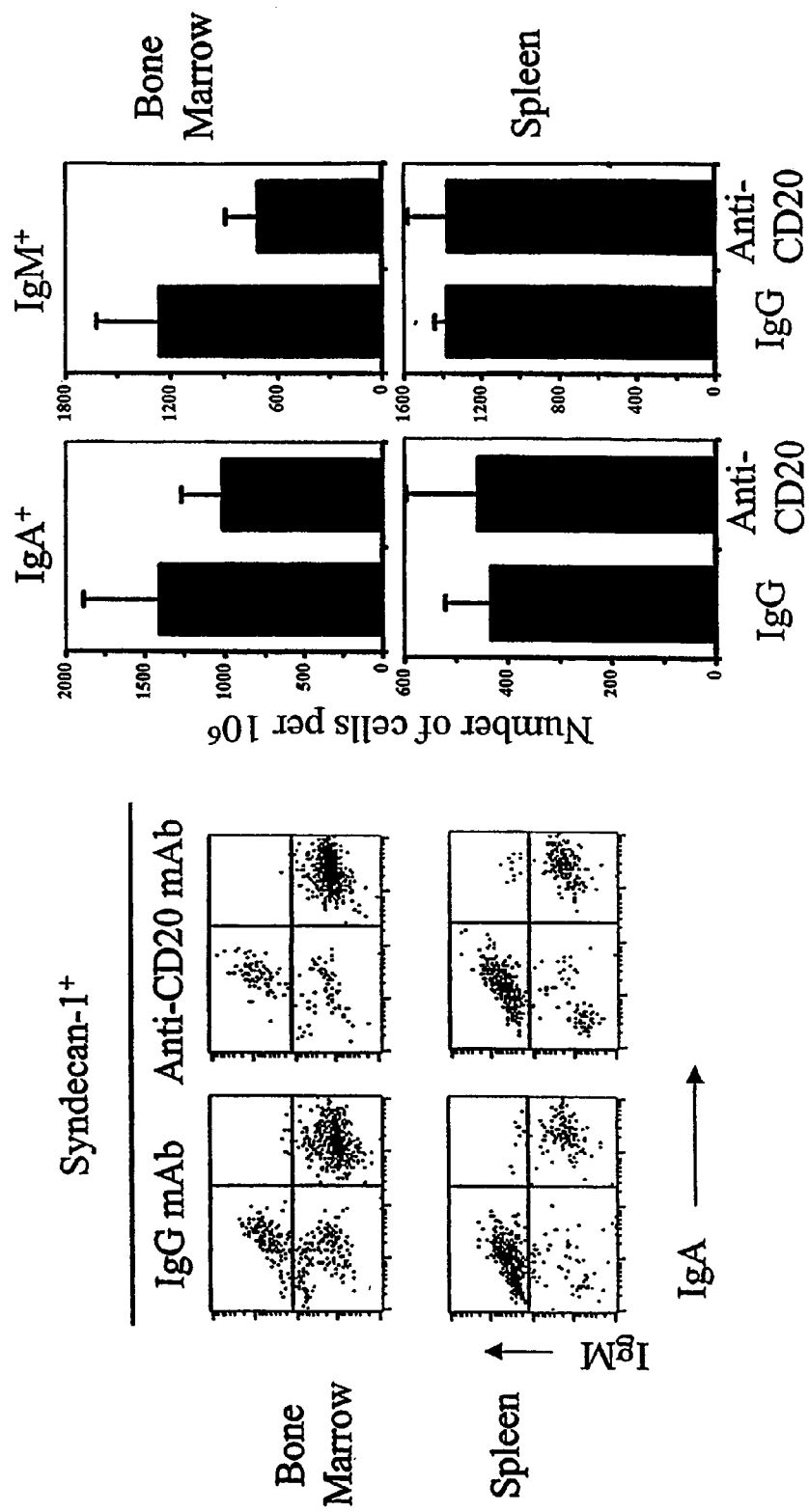
FIG. 18 shows that plasma cells are not depleted following long-term anti-CD20 mAb treatment. Transgenic Tg+ mice positive for human CD20 were treated with anti-human CD20 mH27 antibody as described previously. The mice were analyzed for presence or absence of plasma cells by detecting cells in bone marrow and spleen that were positive for syndican (CD-138 plasma cell marker). The number of IgA or IgM positive plasma cells was also monitored after anti-human CD20 treatment. The results show that plasma cells in Tg+ mice were not affected by the anti-human CD20 antibody treatment, indicating that the Tg+ mice still have the capacity to generate antibodies.

The combination of anti-CD20 mAb and BR3-Fc synergized to deplete all populations of B cells in the spleen. Anti-CD20 mAb depletion spared most of the marginal zone and some follicular/T2 splenic B cells, while BR3-Fc depletion occurred predominantly in the marginal zone and some follicular/T2 B cells (FIG. 16). Thus, the combination of both reagents completely depletes B lineage cells in the spleen. Neither BR3-Fc nor 2H7 nor the combination of the two had an effect on germinal center B cells in Peyer's Patches (FIG. 17). Plasma cells were not significantly affected following anti-CD20 mAb treatment FIG. 18), indicating that some aspects of immune responsiveness were maintained in mice treated with anti-CD20 antibody.

These results show that the combination therapy was effective to deplete most of the B cells. Similar to humans, some B cells in transgenic mice are resistant to killing with anti-CD20 antibodies. The combination therapy provide for depletion of the B cells in the spleen resistant to anti-CD20 antibodies. This shows the transgenic mice are also useful to identify combinations of agents that may be more effective in situations that have anti-CD20 resistant cells or very aggressive tumors.

Example 3

In this experiment, it was demonstrated that natural killer cells play a role in anti-CD20 mAb mediated B cell depletion.

Hybridoma clone, which produces PK-136 mAb (specific against mouse NK1.1), was obtained from ATCC. Four groups of human CD20 transgenic mice were injected ip with control mAb, PK-136, anti-CD20 mAb and the combination of PK-136/anti-CD20, respectively. Doses of ip were as follows:

| control mAb: | 200 ug/ip, 3 ip/week, for 1 week |
| PK-136: | 200 ug/ip, 3 ip/week, for 1 week |
| anti-CD20 mAb: | 10 ug/ip, single dose |

Lymphocytes from peripheral blood, lymph nodes and spleen were analyzed 3 days after anti-CD20 mAb ip. Data is expressed as mean+/−standard error, with n=8.

Figure 19:
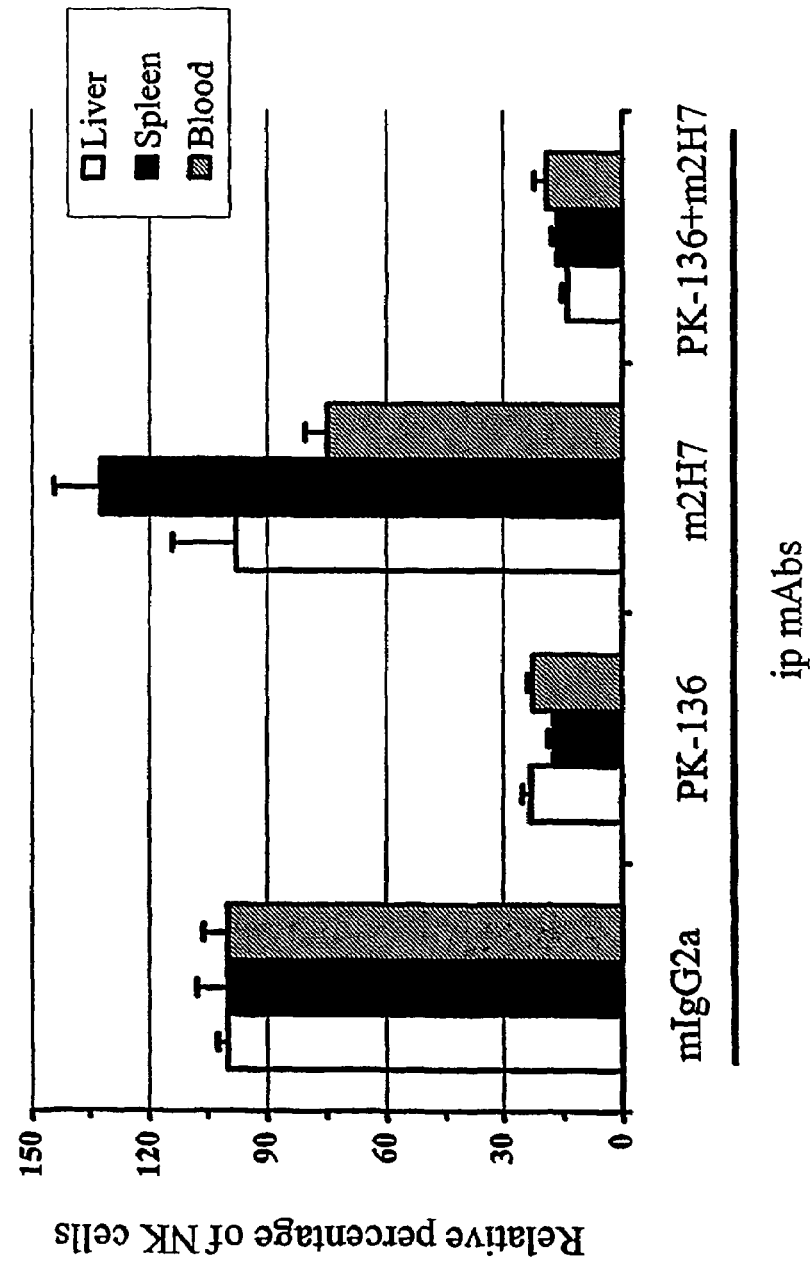
FIG. 19 shows depletion of NK cells by PK-136 mAb in Tg+ mice. Hybridoma clone, which produces PK-136 mAb (specific against mouse NK1.1), was obtained from ATCC. Four groups of human CD20 transgenic mice were injected ip with control mAb, PK-136, anti-CD20 mAb and the combination of PK-136/anti-CD20, respectively. Doses administered ip were as follows.

The results indicated that treatment with PK-136 resulted in an approximately 80% to 90% reduction in NK cell population among the tissues examined (liver, spleen and blood) (FIG. 19). In the absence of majority of NK cells, 2H7 mediated B cell depletion is less efficient(FIG. 20). Thus, NK cells play a role in anti-CD20 mAb mediated B cell depletion.

Example 4

Transgenic animals expressing human CD20/CD16 were generated and evaluated for expression of the human markers.

Human CD20 transgenic mice were generated from human CD20 BAC DNA (Invitrogen, Carlsbad, Calif.) as described in Example 1. Mice were screened based on the FACS analysis of human CD20 expression. Nude mice with human transgene for human CD16 alpha chain subtype A and lacking murine CD16 alpha chain were obtained from Dr. Ravetch. (Rockefeller University) These mice were then mated successively with C57B16, FVB, and 129 mice to obtain mice that were positive for human transgene encoding CD16 alpha chain and were lacking murine CD16 alpha chains in a 129/nude/FVB/B6 background. The FVB mice with human CD20 were then crossed with the 129/nude/FVB/B6 mice having human CD16 alpha chain and lacking mouse CD16 alpha chain.

Expression of human markers in the huCD20Tg+ huCD16Tg+mCD16−/− mice were evaluated by isolating leukocytes from peripheral blood cells and staining them with labeled anti-human CD20 antibodies (m2H7), anti-B220 antibodies (obtained from BD PharMingen), and anti-human CD16 antibodies (obtained from BD PharMingen). Analysis of the stained cell population was conducted using FACS. The huCD20Tg+huCD16Tg+ mCD16−/− were compared with CD20Tg−/Cd16Tg− (control mice), CD20Tg+/CD16Tg−, CD20Tg−/CD16Tg+ mice. The results are shown in FIG. 21.

The results show that CD20Tg+/CD16Tg− mice had cells expressing human CD20 and that these cells were B cells based on their reactivity with anti-B220 antibodies. The CD20Tg−/CD16Tg+ mice had cells that expressed human CD16 based on staining with anti-human CD16 but were not B cells because these cells were not reactive with anti-B220 antibodies. The huCD20Tg+huCD16Tg+mCD16−/− had both CD20 and CD16 positive cells that appeared to be different cell populations. The results demonstrate that the CD20Tg+/CD16Tg+ mouse was successfully generated. These results are also consistent with the view that human CD20 is found on B cells and human CD16 is mainly expressed on natural killer cells, macrophages and granulocytes.

Cells expressing the human CD16 transgene were analyzed to determine which cell types expressed the transgene. Peripheral blood cells were obtained from huCD20+ huCD16+ mCD16−/− transgenic mice and stained with anti-human CD16 antibodies labeled with PE (BD Pharmingen), and were gated with anti-F4/80 antibodies conjugated to APC to detect macrophages or anti-DX5+ antibodies to detect natural killer cells. The results are shown in FIG. 24. The results show that the cells expressing the huCD16+ transgene are natural killer cells and macrophages.

Cells from mice lacking murine CD16 alpha chain were analyzed to determine whether the murine CD16 alpha chain was not present on the cells. Peripheral blood cells from mice lacking murine CD16 alpha chain and wild type mice were stained with anti-mouse CD16 antibodies and analyzed by FACS. The blood cells were gated for macrophages by staining with anti-mac-1. The results are shown in FIG. 26. The results show that there was no detectable murine CD16 alpha chain on cells from mice lacking CD16 alpha chain due to knockout of that gene.

Cells from mice lacking murine CD16 alpha chain were analyzed to determine whether other Fc receptors were expressed. The cells were analyzed for the presence or absence of mouse FcgammaRI (CD64). Peripheral blood cells from mice lacking murine CD16 alpha chain and wild type mice were stained with anti-mouse CD64 monoclonal antibody (prepared by Genentech) and analyzed by FACS. The blood cells were gated for macrophages by staining with anti-mac-1. The results are shown in FIG. 27. The shaded portion is the isotype control. The results show that there was expression of Fcgamma RI (CD64) on macrophages from mice lacking CD16 alpha chain due to knockout of that gene. The weak shift in the staining may be due to the low affinity of the antibody. These results suggest that murine CD16 alpha chain –/– knockout mice expressed other mouse Fc receptors and the mouse gamma chain homodimer.

What is claimed is:

1. A transgenic mouse whose genome comprises a first nucleotide sequence encoding human CD20 and a second nucleotide sequence encoding a subunit of a heterologous FcγIII receptor (CD16), wherein the first nucleotide sequence is operably linked to a CD20 promoter, and wherein the second nucleotide sequence is operably linked to a FcγIII receptor promoter.

2. The transgenic mouse of claim 1, wherein said CD20 promoter is a human promoter.

3. The transgenic mouse of claim 2, whose cells express human CD20.

4. The transgenic mouse of claim 3, wherein human CD20 is expressed on the surface of B lymphocytes.

5. The transgenic mouse of claim 2, wherein said FcγIII receptor promoter is a human promoter.

6. The transgenic mouse of claim 1, wherein said second nucleotide sequence encodes human CD16 alpha chain subtype A.

7. The transgenic mouse of claim 6, wherein said receptor is expressed on the surface of leucocytes.

8. The transgenic mouse of claim 1, wherein said receptor is expressed on the surface of one or more cells selected from the group consisting of NK cells, macrophages, neutrophils, eosinophils, basophils, mast cells, and thymocyte cells.

9. The transgenic mouse of claim 1, wherein the genome of said mouse further comprises a disruption in an endogenous gene encoding a subunit of a receptor substantially homologous to the heterologous FcγIII receptor (CD16).

10. The transgenic mouse of claim 9, wherein the endogenous gene encodes a mouse CD16 alpha chain.

11. A method of identifying an agent capable of treating a B cell lymphoma said method comprising:
 a) measuring the level of B lymphocytes expressing human CD20 in a mouse of claim 1;
 b) administering said agent to the mouse of claim 1; and
 c) measuring the level of B lymphocytes expressing human CD20 in the mouse; wherein a decrease in the number of B lymphocytes expressing human CD20 in the mouse after treatment with the agent identifies the agent capable of treating a B cell lymphoma.

12. A method of identifying an agent capable of depleting or killing cells expressing human CD20 said method comprising:
 a) measuring the level of B lymphocytes expressing human CD20 in a mouse of claim 1;
 b) administering said agent to the mouse of claim 1; and
 c) measuring the level of B lymphocytes expressing human CD20 in the mouse;
  wherein a decrease in the number of B lymphocytes expressing human CD20 in the mouse identifies the agent as capable of depleting or killing cells expressing CD20.

13. The method of claim 12 wherein said cells are cancer cells.

14. A cell or tissue derived from the transgenic mouse of claim 1.

15. A method of identifying an agent capable of inducing an Fc-mediated effector cell response said method comprising
 a) measuring the baseline level of one or more cytokines associated with an Fc-mediated effector cell response in a transgenic mouse of claim 1;
 b) administering said agent to the transgenic mouse;
 c) measuring the level of the cytokines in the mouse; wherein an increase in the level of cytokines after administration identifies the agent as capable of inducing an Fc-mediated effector cell response.

16. A method of identifying an agent capable of inducing an Fc-mediated effector cell response against B lymphocytes expressing human CD20, said method comprising:
 a) measuring the level of B lymphocytes expressing human CD20 in a first transgenic mouse whose genome comprises a nucleotide sequence encoding human CD20 and operably linked to a CD20 promoter;
 b) administering said agent to the first transgenic mouse;
 c) measuring the level of B lymphocytes expressing human CD20 in the first transgenic mouse;
 d) determining the percent reduction in the level of B lymphocytes between step (a) and step (c);
 e) measuring the level of B lymphocytes expressing human CD20 in a second transgenic mouse of claim 1;
 f) administering said agent to the second transgenic mouse of claim 1;
 g) measuring the level of B lymphocytes expressing human CD20 in the second transgenic mouse; and
 h) determining the percent reduction in the level of B lymphocytes between step (e) and step (g);
 wherein if the percent reduction determined in step (h) is greater than the percent reduction determined in step (d), the agent is identified as capable of inducing an Fc-mediated effector cell response against B lymphocytes expressing human CD20.

17. A method of testing safety of anti-human CD20 therapy, said method comprising:
 a) measuring the level of B lymphocytes expressing human CD20 in a mouse of claim 1;
 b) administering said agent to the mouse of claim 1; and
 c) measuring the level of B lymphocytes expressing human CD20 in the mouse; wherein a decrease in the number of B lymphocytes expressing human CD20 in the mouse identifies the agent as capable of depleting or killing cells expressing CD20;
 d) monitoring the mouse for short or long term adverse effects.

18. A method of testing efficacy of anti-human CD20 therapy, said method comprising:
- a) measuring the level of B lymphocytes expressing human CD20 in a set of mice of claim 1;
- b) administering to each mouse of the set a different dose of an agent; and
- c) measuring the level of B lymphocytes expressing human CD20 in the mouse after each dose; and
- d) determining at least one dose of the agent that results in the most B cell depletion.

19. The transgenic mouse of claim 1, wherein the first nucleotide sequence is operably linked to a mouse promoter.

20. The transgenic mouse of claim 1, wherein the second nucleotide sequence is operably linked to a mouse promoter.

21. The cell or tissue of claim 14, wherein the cell or tissue expresses human CD20.

22. The cell or tissue of claim 14, wherein the cell or tissue expresses a subunit of human FcγIII receptor (CD16).

23. The transgenic mouse of claim 6, wherein the human CD20 is expressed on the surface of B lymphocytes and human CD16 alpha chain subtype A is expressed on the surface of leucocytes in the transgenic mouse.

* * * * *